(12) United States Patent
Hidaka et al.

(10) Patent No.: US 10,756,384 B2
(45) Date of Patent: Aug. 25, 2020

(54) ELECTROLYTIC SOLUTION, ELECTROCHEMICAL DEVICE, LITHIUM-ION SECONDARY CELL, AND MODULE

(71) Applicant: DAIKIN INDUSTRIES, LTD., Osaka-shi, Osaka (JP)

(72) Inventors: Tomoya Hidaka, Osaka (JP); Hideo Sakata, Osaka (JP); Kenzou Takahashi, Osaka (JP); Hiroyuki Arima, Osaka (JP); Shigeaki Yamazaki, Osaka (JP); Yoshiko Kuwajima, Osaka (JP); Shinichi Kinoshita, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 0 days.

(21) Appl. No.: 15/768,137

(22) PCT Filed: Oct. 14, 2016

(86) PCT No.: PCT/JP2016/080552
§ 371 (c)(1),
(2) Date: Apr. 13, 2018

(87) PCT Pub. No.: WO2017/069058
PCT Pub. Date: Apr. 27, 2017

(65) Prior Publication Data
US 2018/0294515 A1 Oct. 11, 2018

(30) Foreign Application Priority Data
Oct. 22, 2015 (JP) ................................. 2015-208234

(51) Int. Cl.
| | |
|---|---|
| *H01M 10/0525* | (2010.01) |
| *H01M 10/0568* | (2010.01) |
| *H01M 10/0569* | (2010.01) |
| *C07C 31/36* | (2006.01) |
| *C07F 5/04* | (2006.01) |
| *C07C 43/12* | (2006.01) |
| *H01G 11/64* | (2013.01) |
| *C07C 255/46* | (2006.01) |
| *C07C 69/96* | (2006.01) |
| *C07C 31/42* | (2006.01) |
| *H01G 9/20* | (2006.01) |
| *C07F 9/09* | (2006.01) |
| *H01G 11/62* | (2013.01) |
| *C07C 255/04* | (2006.01) |
| *H01M 10/0567* | (2010.01) |

(Continued)

(52) U.S. Cl.
CPC ......... *H01M 10/0525* (2013.01); *C07C 31/36* (2013.01); *C07C 31/42* (2013.01); *C07C 43/12* (2013.01); *C07C 69/96* (2013.01); *C07C 255/04* (2013.01); *C07C 255/46* (2013.01); *C07C 305/04* (2013.01); *C07F 5/04* (2013.01); *C07F 9/09* (2013.01); *H01G 9/20* (2013.01); *H01G 11/62* (2013.01); *H01G 11/64* (2013.01); *H01M 4/382* (2013.01); *H01M 4/622* (2013.01); *H01M 4/661* (2013.01); *H01M 10/0567* (2013.01); *H01M 10/0568* (2013.01); *H01M 10/0569* (2013.01); *H01M 2004/027* (2013.01); *H01M 2004/028* (2013.01); *Y02E 60/13* (2013.01)

(58) Field of Classification Search
CPC ......... H01M 10/0525; H01M 10/0568; H01M 10/0569; H01M 4/38; H01M 4/62; H01M 4/66; H01M 4/382; H01M 4/622; H01M 4/661; H01M 2004/028; H01M 2004/027; C07C 255/46; C07C 31/42; C07C 69/96; C07C 43/12; C07C 305/04; C07C 255/04; C07C 5/04; C07C 9/09; C07C 31/36; H01G 9/20; H01G 11/62; H01G 11/64; H01G 10/0567; H01G 10/0568; H01G 10/0569; Y02E 60/13
See application file for complete search history.

(56) References Cited

U.S. PATENT DOCUMENTS

2009/0325065 A1* 12/2009 Fujii ..................... H01M 4/133
429/199
2010/0062344 A1 3/2010 Koh et al.
(Continued)

FOREIGN PATENT DOCUMENTS

| | | | |
|---|---|---|---|
| CN | 102479977 | * | 5/2012 |
| EP | 2 597 717 A1 | | 5/2013 |

(Continued)

OTHER PUBLICATIONS

JP2012216388MT (Year: 2012).*
(Continued)

*Primary Examiner* — Alexander Usyatinsky
(74) *Attorney, Agent, or Firm* — Sughrue Mion, PLLC

(57) ABSTRACT

The present invention provides an electrolytic solution capable of providing an electrochemical device (e.g., a lithium ion secondary battery) or a module that is less likely to generate gas even in high-temperature storage and has high capacity retention even after high-temperature storage. The present invention relates to an electrolytic solution which may contain a compound represented by $Y^{21}R^{21}C\!=\!CY^{22}R^{22}$ wherein $R^{21}$ and $R^{22}$ may be the same as or different from each other, and are each H, an alkyl group, or a halogenated alkyl group; $Y^{21}$ and $Y^{22}$ may be the same as or different from each other, and are each $-OR^{23}$ or a halogen atom; and $R^{23}$ is H, an alkyl group, or a halogenated alkyl group.

12 Claims, No Drawings

(51) Int. Cl.
  *C07C 305/04* (2006.01)
  *H01M 4/38* (2006.01)
  *H01M 4/62* (2006.01)
  *H01M 4/66* (2006.01)
  *H01M 4/02* (2006.01)

(56) References Cited

U.S. PATENT DOCUMENTS

| | | | |
|---|---|---|---|
| 2011/0008681 A1 | 1/2011 | Koh et al. | |
| 2013/0164603 A1* | 6/2013 | Suguro | H01M 4/622 429/163 |
| 2013/0330609 A1 | 12/2013 | Sawa et al. | |
| 2013/0330610 A1 | 12/2013 | Shigematsu et al. | |
| 2015/0340679 A1* | 11/2015 | Shimura | H01G 11/52 429/144 |
| 2016/0027592 A1 | 1/2016 | Shimamoto et al. | |
| 2016/0164143 A1 | 6/2016 | Sawa et al. | |

FOREIGN PATENT DOCUMENTS

| | | | | |
|---|---|---|---|---|
| JP | 08037024 | * | 2/1996 | |
| JP | 11-067270 A | | 3/1999 | |
| JP | 2008-027837 A | | 2/2008 | |
| JP | 2008-230970 A | | 10/2008 | |
| JP | 2010-073367 A | | 4/2010 | |
| JP | 2012-216388 A | | 11/2012 | |
| JP | 2012216388 | * | 11/2012 | |
| JP | 2013-033663 A | | 2/2013 | |
| JP | 2015-159120 A | | 9/2015 | |
| WO | 2008/096729 A1 | | 8/2008 | |
| WO | 2009/035085 A1 | | 3/2009 | |
| WO | 2012/029625 A1 | | 3/2012 | |
| WO | WO/2014/091857 | * | 6/2014 | |
| WO | WO-2014091857 A1 | * | 6/2014 | ............ H01G 11/52 |

OTHER PUBLICATIONS

2017546528,Decision_to_Grant_a_Patent (Translated),dated Aug. 6, 2019 (Year: 2019).*
JP08037024MT (Year: 1996).*
Communication dated Apr. 8, 2019, from the European Patent Office in counterpart European Application No. 16857373.1.
International Search Report of PCT/JP2016/080552 dated Nov. 15, 2016.
International Preliminary Report on Patentability with the translation of Written Opinion dated Apr. 24, 2018 issued by the International Bureau in No. PCT/JP2016/080552.

* cited by examiner

ELECTROLYTIC SOLUTION, ELECTROCHEMICAL DEVICE, LITHIUM-ION SECONDARY CELL, AND MODULE

CROSS REFERENCE TO RELATED APPLICATIONS

This application is a National Stage of International Application No. PCT/JP2016/080552 filed Oct. 14, 2016, claiming priority based on Japanese Patent Application No. 2015-208234 filed Oct. 22, 2015.

TECHNICAL FIELD

The present invention relates to electrolytic solutions, electrochemical devices, lithium ion secondary batteries, and modules.

BACKGROUND ART

Current electric appliances demonstrate a tendency to have a reduced weight and a smaller size, which leads to development of lithium ion secondary batteries having a high energy density. Further, lithium ion secondary batteries are used in more various fields, and thus are desired to have improved battery characteristics. In particular, the battery characteristics of lithium ion secondary batteries will become more and more important factors when the batteries are put in use for automobiles.

Patent Literature 1 discloses a non-aqueous electrolyte secondary battery including a positive electrode, a negative electrode that contains lithium or a negative electrode active material capable of occluding and releasing lithium ions, and a non-aqueous electrolytic solution containing an organic solvent and a solute, wherein the organic solvent contains an additive of lithium monofluorophosphate and/or lithium difluorophosphate.

CITATION LIST

Patent Literature

Patent Literature 1: JP H11-67270 A

SUMMARY OF INVENTION

Technical Problem

The present invention aims to provide an electrolytic solution capable of providing an electrochemical device (e.g., a lithium ion secondary battery) or a module that is less likely to generate gas even in high-temperature storage and has high capacity retention even after high-temperature storage.

Solution to Problem

The present invention relates to an electrolytic solution containing at least one compound selected from the group consisting of: a compound (1) represented by formula (1):

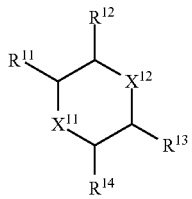

wherein $R^{11}$ to $R^{14}$ may be the same as or different from each other, and are each H, an alkyl group, or a halogenated alkyl group; and $X^{11}$ and $X^{12}$ may be the same as or different from each other, and are each an element in Group 16; and
a compound (2) represented by formula (2):

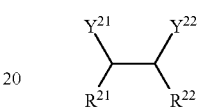

wherein $R^{21}$ and $R^{22}$ may be the same as or different from each other, and are each H, an alkyl group, or a halogenated alkyl group; $Y^{21}$ and $Y^{22}$ may be the same as or different from each other, and are each $-OR^{23}$ or a halogen atom; and $R^{23}$ is H, an alkyl group, or a halogenated alkyl group.

The electrolytic solution preferably contains the compound selected from compounds (1) and (2) in an amount of 0.001 to 10000 mass ppm relative to the electrolytic solution.

The electrolytic solution preferably further contains a solvent. The solvent preferably contains a carbonate. The solvent also preferably contains an acyclic ether.

The electrolytic solution preferably further contains at least one lithium salt (X) selected from the group consisting of:
a compound (3) represented by formula (3):

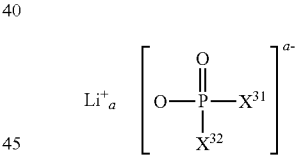

wherein $X^{31}$ and $X^{32}$ may be the same as or different from each other, and are each $-H$, $-F$, $-O$, $-OCN$, an alkyl group which may optionally have an ether bond, a fluorinated alkyl group which may optionally have an ether bond, an alkoxy group which may optionally have an ether bond, or a fluorinated alkoxy group which may optionally have an ether bond; $X^{31}$ and $X^{32}$ may be bonded to each other to form a ring; and a is an integer of 1 to 3;
a compound (4) represented by formula (4):

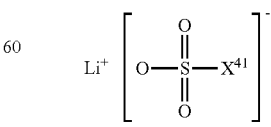

wherein $X^{41}$ is $-H$, $-F$, $-Cl$, an alkyl group which may optionally have an ether bond, a fluorinated alkyl group which may optionally have an ether bond, an alkoxy group which may optionally have an ether bond, or a fluorinated alkoxy group which may optionally have an ether bond;

a compound (5) represented by formula (5):

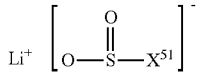

wherein $X^{51}$ is —H, —F, —Cl, an alkyl group which may optionally have an ether bond, a fluorinated alkyl group which may optionally have an ether bond, an alkoxy group which may optionally have an ether bond, or a fluorinated alkoxy group which may optionally have an ether bond; and a compound (6) represented by formula (6):

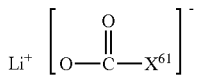

wherein $X^{61}$ is —H, —F, —Cl, an alkyl group which may optionally have an ether bond, a fluorinated alkyl group which may optionally have an ether bond, an alkoxy group which may optionally have an ether bond, or a fluorinated alkoxy group which may optionally have an ether bond.

The electrolytic solution preferably further contains at least one cyclic dicarbonyl compound selected from the group consisting of:

a compound represented by formula (7):

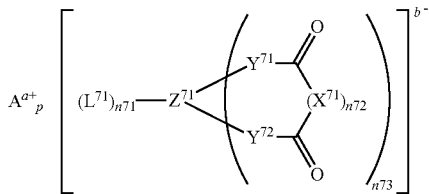

wherein $A^{a+}$ is a metal ion, a hydrogen ion, or an onium ion;

a is an integer of 1 to 3;

b is an integer of 1 to 3;

p is b/a;

$n^{73}$ is an integer of 1 to 4;

$n^{71}$ is an integer of 0 to 8;

$n^{72}$ is 0 or 1;

$Z^{71}$ is a transition metal or an element in Group III, IV, or V of the periodic table;

$X^{71}$ is O, S, a C1-C10 alkylene group, a C1-C10 halogenated alkylene group, a C6-C20 arylene group, or a C6-C20 halogenated arylene group, where the alkylene group, the halogenated alkylene group, the arylene group, and the halogenated arylene group each may have a substituent or a hetero atom in the structure, and $n^{73}$ $X^{71}$s may be bonded to each other when $n^{72}$ is 1 and $n^{73}$ is 2 to 4;

$L^{71}$ is a halogen atom, a cyano group, a C1-C10 alkyl group, a C1-C10 halogenated alkyl group, a C6-C20 aryl group, a C6-C20 halogenated aryl group, or —$Z^{73}Y^{73}$, where the arylene group, the halogenated alkylene group, the arylene group, and the halogenated arylene group each may have a substituent or a hetero atom in the structure, and $n^{71}$ $L^{71}$s may be bonded to each other to form a ring when $n^{71}$ is 2 to 8;

$Y^{71}$, $Y^{72}$, and $Z^{73}$ are each individually O, S, $NY^{74}$, a hydrocarbon group, or a fluorinated hydrocarbon group; and $Y^{73}$ and $Y^{74}$ are each individually H, F, a C1-C10 alkyl group, a C1-C10 halogenated alkyl group, a C6-C20 aryl group, or a C6-C20 halogenated aryl group, where the alkyl group, the halogenated alkyl group, the aryl group, and the halogenated aryl group each may have a substituent or a hetero atom in the structure, and when there are multiple $Y^{73}$s or $Y^{74}$s, the $Y^{73}$s and $Y^{74}$s may be bonded to each other to form a ring; and a compound (8) represented by (8):

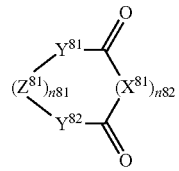

wherein $n^{81}$ is 0 or 1;

$n^{82}$ is 0 or 1;

$Z^{81}$ is a transition metal or an element in Group III, IV, or V in the periodic table;

$X^{81}$ is O, S, a C1-C10 alkylene group, a C1-C10 halogenated alkylene group, a C6-C20 arylene group, or a C6-C20 halogenated arylene group, where the alkylene group, the halogenated alkylene group, the arylene group, and the halogenated arylene group each may have a substituent or a hetero atom in the structure;

$Y^{81}$ and $Y^{82}$ are each individually O, S, $NY^{84}$, a hydrocarbon group, or a fluorinated hydrocarbon group; and $Y^{84}$ is H, a C1-C10 alkyl group, a C1-C10 halogenated alkyl group, a C6-C20 aryl group, or a C6-C20 halogenated aryl group, where the alkyl group, the halogenated alkyl group, the aryl group, and the halogenated aryl group each may have a substituent or a hetero atom in the structure, and when there is multiple $Y^{84}$s, the $Y^{84}$s may be bonded to each other to form a ring.

Preferably, the electrolytic solution further contains a compound (9) containing a multiple bond between a heteroatom other than an oxygen atom and an adjacent atom in a molecule, wherein the compound (9) is at least one selected from the group consisting of compounds represented by formula (9-1) to formula (9-3):

formula (9-1)

formula (9-2)

formula (9-3)

wherein $X^{91}$ is O or N, $M^{91}$ is C, P, S, or N, and $Z^{91}$ is N or may be absent, but $L^{91}$-C=O, where N is absent, $M^{91}$ is C, and $X^{91}$ is O, is excluded;

$L^{91}$ is a halogen atom or an oxygen atom, or R, OR, ORR', ORR'O, SR, NR, SiR, or OSiR that may contain a halogen atom;

R and R' are each a C1-C10 alkyl group, a C1-C10 alkylene group, a C1-C10 alkene group, a C1-C10 alkyne group, a C1-C10 haloalkyl group, a C1-C10 haloalkylene group, a C1-C10 haloalkene group, a C1-C10 haloalkyne group, or a C1-C10 cycloalkyl group;

R and R' may form a ring together;

$n^{91}$ is an integer of 1 to 3; and $m^{91}$ is 1 or 2.

Preferably, the electrolytic solution further contains a compound (9) containing a multiple bond between a hetero atom other than an oxygen atom and an adjacent atom in a molecule, wherein the compound (9) preferably contains a structure represented by any of —C≡N, —N=C=O,

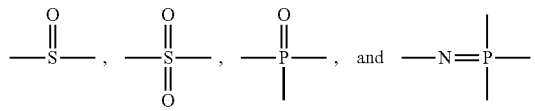

in the electrolytic solution.

Preferably, the electrolytic solution further contains a compound (9) containing a multiple bond between a hetero atom other than an oxygen atom and an adjacent atom in a molecule, wherein the compound (9) is at least one selected from the group consisting of:

a compound (10) represented by formula (10):

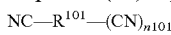

wherein $R^{101}$ is a monovalent to trivalent hydrocarbon group or a monovalent to trivalent halogenated hydrocarbon group; and $n^{10}1$ is an integer of 0 to 2;

a compound (11) represented by formula (11):

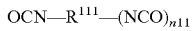

wherein $R^{111}$ is a monovalent or divalent hydrocarbon group or a monovalent or divalent halogenated hydrocarbon group; and $n^{111}$ is 0 or 1;

a compound (12) represented by formula (12):

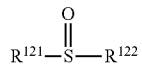

wherein $R^{121}$ and $R^{122}$ may be the same as or different from each other, and are each a halogen atom, a monovalent or divalent hydrocarbon group, or a monovalent or divalent halogenated hydrocarbon group; and $R^{121}$ and $R^{122}$ may be bonded to each other to form a ring;

a compound (13) represented by formula (13):

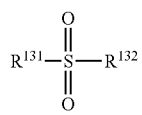

wherein $R^{131}$ and $R^{132}$ may be the same as or different from each other, and are each a halogen atom, a monovalent or divalent hydrocarbon group, or a monovalent or divalent halogenated hydrocarbon group; and $R^{131}$ and $R^{132}$ may be bonded to each other to form a ring;

a compound (14) represented by formula (14):

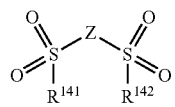

wherein $R^{141}$ and $R^{142}$ may be the same as or different from each other, and are each a halogen atom, a monovalent or divalent hydrocarbon group, or a monovalent or divalent halogenated hydrocarbon group; $R^{141}$ and $R^{142}$ may be bonded to each other to form a ring; and Z is an oxygen atom or a C1-C10 alkylene group, a compound (15) represented by formula (15):

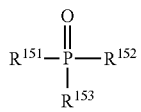

wherein $R^{151}$ to $R^{153}$ may be the same as or different from each other, and are each an organic group;

a compound (16) represented by formula (16):

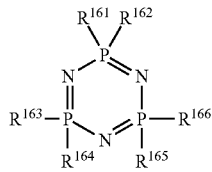

wherein $R^{161}$ to $R^{166}$ may be the same as or different from each other, and are each a halogen atom or an organic group; and a compound (17) represented by formula (17):

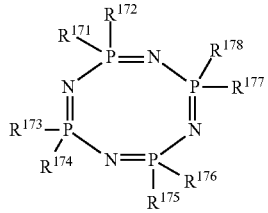

wherein $R^{171}$ to $R^{178}$ may be the same as or different from each other, and are each a halogen atom or an organic group.

The present invention also relates to an electrochemical device including the above electrolytic solution.

The present invention also relates to a lithium ion secondary battery including the above electrolytic solution.

The present invention also relates to a module including the above electrochemical device or the above lithium ion secondary battery.

Advantageous Effects of Invention

The use of the electrolytic solution of the present invention makes it possible to achieve an electrochemical device or module that is less likely to generate gas even in high-temperature storage and has high capacity retention even after high-temperature storage.

DESCRIPTION OF EMBODIMENTS

The present invention will be specifically described hereinbelow.

The electrolytic solution of the present invention contains at least one compound selected from the group consisting of a compound (1) and a compound (2).

The compound (1) is represented by formula (1):

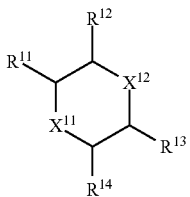

wherein $R^{11}$ to $R^{14}$ may be the same as or different from each other, and are each H, an alkyl group, or a halogenated alkyl group; and $X^{11}$ and $X^{12}$ may be the same as or different from each other, and are each an element in Group 16.

The lower limit of the carbon number of the alkyl group for $R^{11}$ to $R^{14}$ is preferably 1. The upper limit of the carbon number of the alkyl group is preferably 5, more preferably 4.

The lower limit of the carbon number of the halogenated alkyl group for $R^{11}$ to $R^{14}$ is preferably 1. The upper limit of the carbon number of the halogenated alkyl group is preferably 5, more preferably 4.

The halogenated alkyl group for $R^{11}$ to $R^{14}$ is preferably a fluorinated alkyl group. The lower limit of the carbon number of the fluorinated alkyl group is preferably 1. The upper limit of the carbon number of the fluorinated alkyl group is preferably 5, more preferably 4.

In the compound (1), preferably, $R^{11}$ and $R^{13}$ are each individually a halogenated alkyl group and $R^{12}$ and $R^{14}$ are H.

More preferably, $R^{11}$ and $R^{13}$ are each individually a fluorinated alkyl group and $R^{12}$ and $R^{14}$ are H.

Still more preferably, $R^{11}$ and $R^{13}$ are each individually a C1-C5 fluorinated alkyl group and $R^{12}$ and $R^{14}$ are H.

$X^{11}$ and $X^{12}$ are preferably individually O or S, more preferably both are O.

The compound (2) is represented by formula (2):

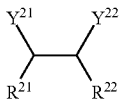

wherein $R^{21}$ and $R^{22}$ may be the same as or different from each other, and are each H, an alkyl group, or a halogenated alkyl group; $Y^{21}$ and $Y^{22}$ may be the same as or different from each other, and are each —$OR^{23}$ or a halogen atom; and $R^{23}$ is H, an alkyl group, or a halogenated alkyl group.

The lower limit of the carbon number of the alkyl group for $R^{21}$ to $R^{23}$ is preferably 1. The upper limit of the carbon number of the alkyl group is preferably 5, more preferably 4.

The lower limit of the carbon number of the halogenated alkyl group for $R^{21}$ to $R^{23}$ is preferably 1. The upper limit of the carbon number of the halogenated alkyl group is preferably 5, more preferably 4.

The halogenated alkyl group for $R^{21}$ to $R^{23}$ is preferably a fluorinated alkyl group. The lower limit of the carbon number of the fluorinated alkyl group is preferably 1. The upper limit of the carbon number of the fluorinated alkyl group is preferably 5, more preferably 4.

The halogen atom is preferably an element in the second to fifth periods, more preferably Br.

$R^{23}$ is preferably H.

Preferably, in the compound (2), one of $R^{21}$ and $R^{22}$ is H and the other is a halogenated alkyl group, and one of $Y^{21}$ and $Y^{22}$ is —$OR^{23}$ and the other is —$OR^{23}$ or a halogen atom.

More preferably, one of $R^{21}$ and $R^{22}$ is H and the other is a fluorinated alkyl group, and one of $Y^{21}$ and $Y^{22}$ is —OH and the other is —OH or a halogen atom.

The electrolytic solution preferably contains the compound selected from compounds (1) and (2) in an amount of 0.001 to 10000 mass ppm, more preferably 0.1 mass ppm or more, still more preferably 0.5 mass ppm or more, while more preferably 150 mass ppm or less, still more preferably 30 mass ppm or less. The amount of the compound selected from compounds (1) and (2) can be determined by GC-MS analysis.

The electrolytic solution of the present invention preferably further contains a lithium salt (X). Containing the lithium salt (X) allows the electrolytic solution of the present invention, when applied to a lithium ion secondary battery, to give an improved Li ion transport rate. In addition, the lithium ion secondary battery is less likely to generate gas even in high-temperature storage, and can have high capacity retention even after high-temperature storage.

The amount of the lithium salt (X) in the electrolytic solution is preferably 0.001 to 5 mass %. The amount of the lithium salt (X) in the electrolytic solution is more preferably 0.01 mass % or more, still more preferably 0.08 mass % or more, while more preferably 3 mass % or less, still more preferably 1 mass % or less. The amount of the lithium salt (X) can be determined by GC-MS analysis.

The lithium salt (X) is at least one selected from the group consisting of compounds (3) to (6), which will be described later. The lithium salt (X) is preferably at least one selected from the group consisting of compounds (3) to (5), more preferably at least one selected from the group consisting of compounds (3) and (4), still more preferably a compound (3).

The compound (3) is represented by formula (3):

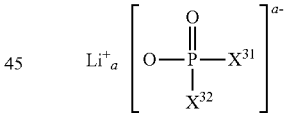

wherein $X^{31}$ and $X^{32}$ may be the same as or different from each other, and are each —H, —F, —O, —OCN, an alkyl group which may optionally have an ether bond, a fluorinated alkyl group which may optionally have an ether bond, an alkoxy group which may optionally have an ether bond, or a fluorinated alkoxy group which may optionally have an ether bond; $X^{31}$ and $X^{32}$ may be bonded to each other to form a ring; and a is an integer of 1 to 3.

The term "ether bond" herein means a bond represented by —O—.

The carbon number of the alkyl group, the fluorinated alkyl group, the alkoxy group, and the fluorinated alkoxy group is preferably 1 to 10, more preferably 1 to 3. The alkyl group, the fluorinated alkyl group, the alkoxy group, and the fluorinated alkoxy group preferably have no ether bond.

Preferably, one or both of $X^{31}$ and $X^{32}$ is/are —F, a fluorinated alkyl group which may optionally have an ether bond, or a fluorinated alkoxy group which may optionally have an ether bond. More preferably, both of them are —F, a C1-C3 fluorinated alkyl group which has no ether bond, or a C1-C3 fluorinated alkoxy group which has no ether bond.

The alkyl group, the fluorinated alkyl group, the alkoxy group, and the fluorinated alkoxy group may be substituted with —C≡N, —S(=O)$_2$—, —S(=O)$_2$—O—, —OM (M is a metal atom), or the like. Examples of M include alkali metal atoms. M may be Li.

Examples of the compound (3) include LiPO$_2$F$_2$, Li$_2$PO$_3$F, Li$_3$PO$_4$, LiOP(O)(CH$_3$)F, LiOP(O)(CF$_3$)F, LiOP(O)(C$_2$H$_5$)F, LiOP(O)(CH$_2$CF$_3$)F, LiOP(O)(CF$_2$CF$_3$)F, LiOP(O)(OCH$_3$)F, LiOP(O)(OCF$_3$)F, LiOP(O)(OC$_2$H$_5$)F, LiOP(O)(OCH$_2$CF$_3$)F, LiOP(O)(OCF$_2$CF$_3$)F, LiOP(O)(OCH$_3$)$_2$, LiOP(O)(OCH$_3$)(OCF$_3$), LiOP(O)(OCF$_3$)$_2$, LiOP(O)(OCH$_2$CF$_3$)$_2$, LiOP(O)(OCH$_2$CF$_3$)(OCH$_3$), LiOP(O)(OCH$_2$CF$_2$CF$_3$)$_2$, LiOP(O)(OCH$_2$CH$_2$F)$_2$, LiOP(O)(OCH$_2$CHF$_2$)$_2$, LiOP(O)(OCH$_2$CF$_3$)(OCN), LiOP(O)(OCH$_2$CHF$_2$)(OCN), LiOP(O)(OCH$_2$CN)$_2$, and LiOP(O)(OCH$_2$CF$_3$)(OCH$_2$CN).

The compound (3) preferably has a F atom from the standpoint of oxidation resistance, and is preferably at least one selected from the group consisting of LiPO$_2$F$_2$, LiOP(O)(OCF$_3$)$_2$, and LiOP(O)(OCH$_2$CF$_3$)$_2$ from the standpoint of resistance.

The compound (4) is represented by formula (4):

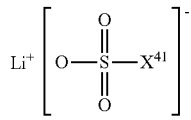

wherein $X^{41}$ is —H, —F, —Cl, an alkyl group which may optionally have an ether bond, a fluorinated alkyl group which may optionally have an ether bond, an alkoxy group which may optionally have an ether bond, or a fluorinated alkoxy group which may optionally have an ether bond.

The carbon number of the alkyl group, the fluorinated alkyl group, the alkoxy group, and the fluorinated alkoxy group is preferably 1 to 10, more preferably 1 to 3. The alkyl group, the fluorinated alkyl group, the alkoxy group, and the fluorinated alkoxy group preferably have no ether bond.

$X^{41}$ is preferably —F, an alkyl group which may optionally have an ether bond, a fluorinated alkyl group which may optionally have an ether bond, an alkoxy group which may optionally have an ether bond, or a fluorinated alkoxy group which may optionally have an ether bond, more preferably —F, a C1-C3 alkyl group which has no ether bond, or a C1-C3 fluorinated alkoxy group which has no ether bond.

The alkyl group, the fluorinated alkyl group, the alkoxy group, and the fluorinated alkoxy group may be substituted with —C≡N, —S(=O)$_2$—, —S(=O)$_2$—O—, —OM (M is a metal atom), or the like. Examples of M include alkali metal atoms. M may be Li.

Examples of the compound (4) include LiOSO$_2$F, LiOSO$_2$CH$_3$, LiOSO$_2$CF$_3$, LiOSO$_2$(OCH$_3$), LiOSO$_2$(OCF$_3$), LiOSO$_2$(OCH$_2$CH$_3$), LiOSO$_2$(OCH$_2$CF$_3$), LiOSO$_2$(OCF$_2$CF$_3$), LiOSO$_2$(OCH$_2$CH$_2$CH$_3$), and LiOSO$_2$(OCH$_2$CH$_2$CF$_3$).

The compound (4) is preferably at least one selected from the group consisting of LiOSO$_2$F, LiOSO$_2$CH$_3$, and LiOSO$_2$(OCH$_2$CH$_3$).

The compound (5) is represented by formula (5):

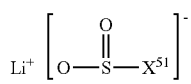

wherein $X^{51}$ is —H, —F, —Cl, an alkyl group which may optionally have an ether bond, a fluorinated alkyl group which may optionally have an ether bond, an alkoxy group which may optionally have an ether bond, or a fluorinated alkoxy group which may optionally have an ether bond.

The carbon number of the alkyl group, the fluorinated alkyl group, the alkoxy group, and the fluorinated alkoxy group is preferably 1 to 10, more preferably 1 to 3. The alkyl group, the fluorinated alkyl group, the alkoxy group, and the fluorinated alkoxy group preferably have no ether bond.

The alkyl group, the fluorinated alkyl group, the alkoxy group, and the fluorinated alkoxy group may be substituted with —C≡N, —S(=O)$_2$—, —S(=O)$_2$—O—, —OM (M is a metal atom), or the like. Examples of M include alkali metal atoms. M may be Li.

$X^{51}$ is preferably —F, a C1-C3 fluorinated alkyl group which has no ether bond, or a C1-C3 fluorinated alkoxy group which has no ether bond.

Examples of the compound (5) include LiOSOF, LiOSOCH$_3$, LiOSOCF$_3$, LiOSO(OCH$_3$), LiOSO(OCF$_3$), LiOSO(OCH$_2$CH$_3$), LiOSO(OCH$_2$CF$_3$), LiOSO(OCF$_2$CF$_3$), and LiOSO(OCH$_2$CH$_2$CH$_3$), and LiOSO(OCH$_2$CH$_2$CF$_3$).

The compound (5) is preferably at least one selected from the group consisting of LiOSOF, LiOSOCF$_3$, and LiOSO(OCF$_3$).

The compound (6) is represented by formula (6):

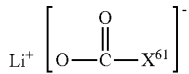

wherein $X^{61}$ is —H, —F, —Cl, an alkyl group which may optionally have an ether bond, a fluorinated alkyl group which may optionally have an ether bond, an alkoxy group which may optionally have an ether bond, or a fluorinated alkoxy group which may optionally have an ether bond.

The carbon number of the alkyl group, the fluorinated alkyl group, the alkoxy group, and the fluorinated alkoxy group is preferably 1 to 10, more preferably 1 to 3. The alkyl group, the fluorinated alkyl group, the alkoxy group, and the fluorinated alkoxy group preferably have no ether bond.

The alkyl group, the fluorinated alkyl group, the alkoxy group, and the fluorinated alkoxy group may be substituted with —C≡N, —S(=O)$_2$—, —S(=O)$_2$—O—, —OM (M is a metal atom), or the like. Examples of M include alkali metal atoms. M may be Li.

$X^{61}$ is preferably —F or a C1-C3 fluorinated alkoxy group which has no ether bond.

Examples of the compound (6) include LiOCOF, LiOCO(CH$_3$), LiOCO(CF$_3$), LiOCO(CFH$_2$), LiOCO(CF$_2$H), LiOCO(CH$_2$CH$_3$), LiOCO(CH$_2$CF$_3$), LiOCO(CH$_2$CF$_2$H), LiOCO(CF$_2$CF$_3$), LiOCO(CH$_2$CH$_2$CH$_3$), LiOCO(CH$_2$CH$_2$CF$_3$), LiOCO(CH$_2$CF$_2$CF$_3$), LiOCO(CH$_2$CF$_2$CF$_2$H), LiOCO(OCF$_3$), and LiOCO(OCH$_2$CH$_3$).

The compound (6) is preferably at least one selected from the group consisting of LiOCOF and LiOCO(CF$_3$).

The electrolytic solution of the present invention preferably further contains a cyclic dicarbonyl compound. When the electrolytic solution of the present invention contains the cyclic dicarbonyl compound and is applied to a lithium ion secondary battery, the lithium ion secondary battery is less likely to generate gas even in high-temperature storage, and can have high capacity retention even after high-temperature storage.

The amount of the cyclic dicarbonyl compound is preferably 0.001 to 10 mass %, more preferably 0.01 mass % or more, still more preferably 0.05 mass % or more, particularly preferably 0.08 mass % or more, while more preferably 3 mass % or less, still more preferably 2 mass % or less. The amount of the cyclic dicarbonyl compound can be determined by GC-MS analysis.

The cyclic dicarbonyl compound is preferably at least one selected from the group consisting of a compound (7) and a compound (8).

The compound (7) is represented by formula (7):

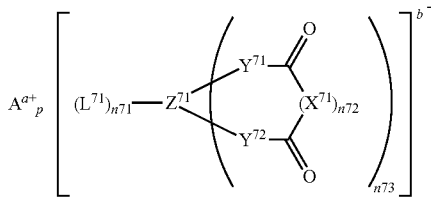

wherein $A^{a+}$ is a metal ion, a hydrogen ion, or an onium ion;

a is an integer of 1 to 3;

b is an integer of 1 to 3;

p is b/a;

$n^{73}$ is an integer of 1 to 4;

$n^{71}$ is an integer of 0 to 8;

$n^{72}$ is 0 or 1;

$Z^{71}$ is a transition metal or an element in Group III, IV, or V of the periodic table;

$X^{71}$ is O, S, a C1-C10 alkylene group, a C1-C10 halogenated alkylene group, a C6-C20 arylene group, or a C6-C20 halogenated arylene group, where the alkylene group, the halogenated alkylene group, the arylene group, and the halogenated arylene group each may have a substituent or a hetero atom in the structure, and $n^{73}$ $X^{71}$s may be bonded to each other when $n^{72}$ is 1 and $n^{73}$ is 2 to 4;

$L^{71}$ is a halogen atom, a cyano group, a C1-C10 alkyl group, a C1-C10 halogenated alkyl group, a C6-C20 aryl group, a C6-C20 halogenated aryl group, or $-Z^{73}Y^{73}$, where the alkylene group, the halogenated alkylene group, the arylene group, and the halogenated arylene group each may have a substituent or a hetero atom in the structure, and $n^{71}$ $L^{71}$s may be bonded to each other to form a ring when $n^{71}$ is 2 to 8;

$Y^{71}$, $Y^{72}$, and $Z^{73}$ are each individually O, S, $NY^{74}$, a hydrocarbon group, or a fluorinated hydrocarbon group; and $Y^{73}$ and $Y^{74}$ are each individually H, F, a C1-C10 alkyl group, a C1-C10 halogenated alkyl group, a C6-C20 aryl group, or a C6-C20 halogenated aryl group, where the alkyl group, the halogenated alkyl group, the aryl group, and the halogenated aryl group each may have a substituent or a hetero atom in the structure, and when there are multiple $Y^{73}$s or $Y^{74}$s, the $Y^{73}$s and $Y^{74}$s may be bonded to each other to form a ring.

Examples of $A^{a+}$ include a lithium ion, a sodium ion, a potassium ion, a magnesium ion, a calcium ion, a barium ion, a caesium ion, a silver ion, a zinc ion, a copper ion, a cobalt ion, an iron ion, a nickel ion, a manganese ion, a titanium ion, a lead ion, a chromium ion, a vanadium ion, a ruthenium ion, an yttrium ion, lanthanoid ions, actinoid ions, a tetrabutyl ammonium ion, a tetraethyl ammonium ion, a tetramethyl ammonium ion, a triethyl methyl ammonium ion, a triethyl ammonium ion, a pyridinium ion, an imidazolium ion, a hydrogen ion, a tetraethyl phosphonium ion, a tetramethyl phosphonium ion, a tetraphenyl phosphonium ion, a triphenyl sulfonium ion, and a triethyl sulfonium ion.

In applications such as electrochemical devices, $A^{a+}$ is preferably a lithium ion, a sodium ion, a magnesium ion, a tetraalkyl ammonium ion, or a hydrogen ion, particularly preferably a lithium ion. The valence (a) of the cation $A^{a+}$ is an integer of 1 to 3. If the valence is greater than 3, the crystal lattice energy is high and the compound (7) has difficulty in dissolving in the solvent. Thus, the valence is more preferably 1 if good solubility is needed. The valence (b) of the anion is also an integer of 1 to 3, particularly preferably 1. The constant p that represents the ratio between the cation and the anion is naturally defined by the ratio b/a between the valences thereof.

Next, the ligands in formula (7) are described. As used herein, organic or inorganic groups bonded to $Z^{71}$ in formula (7) are referred to as ligands.

$Z^{71}$ is preferably Al, B, V, Ti, Si, Zr, Ge, Sn, Cu, Y, Zn, Ga, Nb, Ta, Bi, P, As, Sc, Hf, or Sb, more preferably Al, B, or P.

$X^{71}$ is O, S, a C1-C10 alkylene group, a C1-C10 halogenated alkylene group, a C6-C20 arylene group, or a C6-C20 halogenated arylene group. These alkylene groups and arylene groups each may have a substituent or a hetero atom in the structure. Specifically, instead of the hydrogen of the alkylene group or the arylene group, the structure may have a halogen atom, an acyclic or cyclic alkyl group, an aryl group, an alkenyl group, an alkoxy group, an aryloxy group, a sulfonyl group, an amino group, a cyano group, a carbonyl group, an acyl group, an amide group, or a hydroxy group as a substituent; or, instead of the carbon of the alkylene or the arylene, the structure may have nitrogen, sulfur, or oxygen introduced therein. When $n^{72}$ is 1 and $n^{73}$ is 2 to 4, $n^{73}$ $X^{71}$s may be bonded to each other. One such example is a ligand such as ethylenediamine tetraacetic acid.

$L^{71}$ is a halogen atom, a cyano group, a C1-C10 alkyl group, a C1-C10 halogenated alkyl group, a C6-C20 aryl group, a C6-C20 halogenated aryl group, or $-Z^{73}Y^{73}$ ($Z^{73}$ and $Y^{73}$ will be described later). Similar to $X^{71}$, the alkyl groups and the aryl groups each may have a substituent or a hetero atom in the structure, and when $n^{71}$ is 2 to 8, $n^{71}$ $L^{71}$s may be bonded to each other to form a ring. $L^{71}$ is preferably a fluorine atom or a cyano group. This is because a fluorine atom can improve the solubility and the degree of dissociation of an anion compound salt, which involves improvement of the ion conductivity. This is also because a fluorine atom can improve the oxidation resistance, which makes it possible to restrain occurrence of side reactions.

$Y^{71}$, $Y^{72}$, and $Z^{73}$ are each individually O, S, $NY^{74}$, a hydrocarbon group, or a fluorinated hydrocarbon group. $Y^{71}$ and $Y^{72}$ are each preferably O, S, or $NY^{74}$, more preferably O. The compound (7) characteristically has bonds to $Z^{71}$ via $Y^{71}$ and $Y^{72}$ in the same ligand. Such a ligand forms a chelate structure with $Z^{71}$. The effect of this chelate improves the heat resistance, the chemical stability, and the hydrolysis resistance of this compound. The constant $n^{72}$ of the ligand is 0 or 1. In particular, $n^{72}$ is preferably 0 because the chelate ring becomes a five-membered ring and the chelate effect is most strongly achieved, improving the stability.

The term "fluorinated hydrocarbon group" herein refers to a hydrocarbon group in which at least one hydrogen atom has been replaced by a fluorine atom.

$Y^{73}$ and $Y^{74}$ are each individually H, a C1-C10 alkyl group, a C1-C10 halogenated alkyl group, a C6-C20 aryl group, or a C6-C20 halogenated aryl group. These alkyl groups and aryl groups each may have a substituent or a hetero atom in the structure. When there are multiple $Y^{73}$s or $Y^{74}$s, they may be bonded to each other to form a ring.

The constant $n^{73}$ relating to the number of the aforementioned ligands is an integer of 1 to 4, preferably 1 or 2, more preferably 2. The constant $n^{71}$ relating to the number of the aforementioned ligands is an integer of 0 to 8, preferably an integer of 0 to 4, more preferably 0, 2, or 4. In addition, $n^{71}$ is preferably 2 when $n^{73}$ is 1, and $n^{71}$ is preferably 0 when $n^{73}$ is 2.

In formula (7), the alkyl group, the halogenated alkyl group, the aryl group, and the halogenated aryl group include those having other functional groups such as branches, hydroxy groups, and ether bonds.

The compound (7) is preferably a compound represented by the following formula:

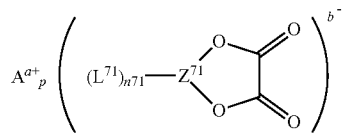

wherein $A^{a+}$, a, b, p, $n^{71}$, $Z^{71}$, and $L^{71}$ are as described above, or a compound represented by the following formula:

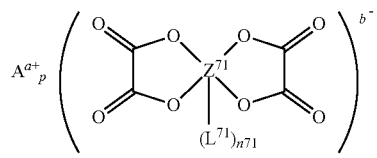

wherein $A^{a+}$, a, b, p, $n^{71}$, $Z^{71}$, and $L^{71}$ are as described above.

The compound (7) may be a lithium oxalatoborate salt. Examples thereof include lithium bis(oxalato)borate represented by the following formula:

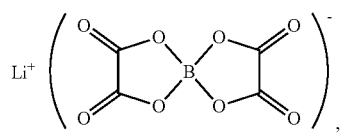

lithium difluorooxalatoborate represented by the following formula:

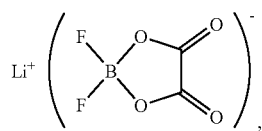

and lithium dicyanooxlatoborate represented by the following formula:

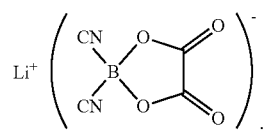

Examples of the compound (7) also include lithium tetrafluorooxalatophosphate represented by the following formula:

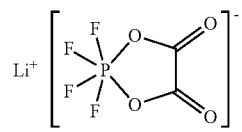

and lithium bis(oxalato)difluorophosphate represented by the following formula:

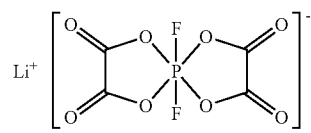

The compound (8) is represented by formula (8):

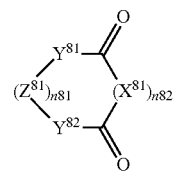

wherein n is 0 or 1;

$n^{82}$ is 0 or 1;

$Z^{81}$ is a transition metal or an element in Group III, IV, or V in the periodic table;

$X^{81}$ is O, S, a C1-C10 alkylene group, a C1-C10 halogenated alkylene group, a C6-C20 arylene group, or a C6-C20 halogenated arylene group, where the alkylene group, the halogenated alkylene group, the arylene group, and the halogenated arylene group each may have a substituent or a hetero atom in the structure;

$Y^{81}$ and $Y^{82}$ are each individually O, S, $NY^{84}$, a hydrocarbon group, or a fluorinated hydrocarbon group; and $Y^{84}$ is H, a C1-C10 alkyl group, a C1-C10 halogenated alkyl group, a C6-C20 aryl group, or a C6-C20 halogenated aryl group, where the alkyl group, the halogenated alkyl group, the aryl group, and the halogenated aryl group each may have a substituent or a hetero atom in the structure, and when there is multiple $Y^{84}$s, the $Y^{84}$s may be bonded to each other to form a ring.

$Z^{81}$ may be Al, B, V, Ti, Si, Zr, Ge, Sn, Cu, Y, Zn, Ga, Nb, Ta, Bi, P, As, Sc, Hf, Sb or the like. Preferably, $n^{81}$ is 0.

Preferably, $n^{82}$ is 1. $X^{81}$ is preferably O or S, more preferably O.

$Y^{81}$ and $Y^{82}$ are preferably each individually a hydrocarbon group or a fluorinated hydrocarbon group, more preferably a C1-C3 hydrocarbon group or a C1-C3 fluorinated hydrocarbon group. Preferably, $n^{81}$ is 0 and $Y^{81}$ and $Y^{82}$ are bonded to each other to form a ring.

The compound (8) is preferably a compound represented by the formula:

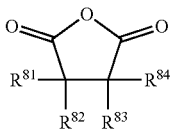

wherein $R^{81}$ to $R^{84}$ may be the same as or different from each other, and are each H, F, an alkyl group, or a fluorinated alkyl group, or a compound represented by the formula:

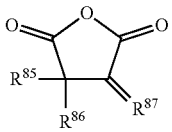

wherein $R^{85}$ and $R^{86}$ may be the same as or different from each other, and are each H, F, an alkyl group, or a fluorinated alkyl group; and $R^{87}$ is an alkene group or a fluorinated alkene group.

The carbon number of the alkyl group, the fluorinated alkyl group, the alkene group, and the fluorinated alkene group is preferably 1 to 10. For good compatibility with the electrolytic solution, the carbon number is more preferably 1 to 3.

Examples of $R^{81}$ to $R^{86}$ include H—, F—, $CH_3$—, $CH_3CH_2$—, $CH_3CH_2CH_2$—, $CF_3$—, $CF_3CF_2$—, $CH_2FCH_2$—, and $CF_3CF_2CF_2$—.

Examples of $R^{87}$ include $CH_2$= and $CH_3CH_2$=.

The compound (8) is preferably a compound represented by the formula:

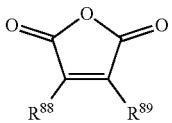

wherein $R^{88}$ and $R^{89}$ may be the same as or different from each other, and are each H, F, an alkyl group, or a fluorinated alkyl group.

The carbon number of the alkyl group and the fluorinated alkyl group is preferably 1 to 10. For good compatibility with the electrolytic solution, the carbon number is more preferably 1 to 3.

Examples of $R^{88}$ and $R^{89}$ include H—, F—, $CH_3$—, $CH_3CH_2$—, $CH_3CH_2CH_2$—, $CF_3$—, $CF_3CF_2$—, $CH_2FCH_2$—, and $CF_3CF_2CF_2$—.

Examples of the compound (8) include succinic anhydride, glutaric anhydride, itaconic anhydride, diglycolic anhydride, cyclohexanecarboxylic anhydride, cyclopentanetetracarboxylic anhydride, phenylsuccinic anhydride, dimethylsuccinic anhydride, trifluoromethylsuccinic anhydride, monofluorosuccinic anhydride, tetrafluorosuccinic anhydride, maleic anhydride, citraconic anhydride, and trifluoromethylmaleic anhydride.

In particular, maleic anhydride and trifluoromethylmaleic anhydride are preferred.

The electrolytic solution of the present invention preferably contains a compound (9). When the electrolytic solution of the present invention contains the compound (9) and is applied to a lithium ion battery, the lithium ion battery is less likely to generate gas even in high-temperature storage, and can have high capacity retention even after high-temperature storage.

The amount of the compound (9) relative to the electrolytic solution is preferably 0.001 to 20 mass %, more preferably 0.01 mass % or more, still more preferably 0.08 mass % or more, particularly preferably 0.5 mass % or more, while more preferably 10 mass % or less, still more preferably 5 mass % or less. The amount of the compound (9) can be determined by GC-MS analysis.

The compound (9) contains, in the molecule, a multiple bond between a hetero atom (excluding an oxygen atom) and an adjacent atom. The hetero atom is an atom other than carbon and hydrogen. The hetero atom is preferably at least one selected from the group consisting of S, P, and N. The multiple bond is a multiple bond between the hetero atom and an atom adjacent to the hetero atom. The multiple bond is preferably a double bond or triple bond, more preferably a double bond. Examples of the multiple bond include a multiple bond between the hetero atom and a carbon atom, a multiple bond between the hetero atom and an oxygen atom, and a multiple bond between the hetero atoms.

The compound (9) is preferably at least one selected from the group consisting of compounds represented by formula (9-1):

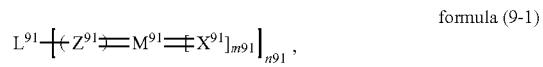 formula (9-1)

 formula (9-2)

 formula (9-3)

wherein
$X^{91}$ is O or N, $M^{91}$ is C, P, S, or N, and $Z^{91}$ is N or may be absent, but $L^{91}$-C=O, where N is absent, $M^{91}$ is C, and $X^{91}$ is O, is excluded;

$L^{91}$ is a halogen atom or an oxygen atom, or R, OR, ORR', ORR'O, SR, NR, SiR, or OSiR that may contain a halogen atom;

R and R' are each a C1-C10 alkyl group, a C1-C10 alkylene group, a C1-C10 alkene group, a C1-C10 alkyne group, a C1-C10 haloalkyl group, a C1-C10 haloalkylene group, a C1-C10 haloalkene group, a C1-C10 haloalkyne group, or a C1-C10 cycloalkyl group;

R and R' may form a ring together;
$n^{91}$ is an integer of 1 to 3; and
$m^{91}$ is 1 or 2.

Preferably, a structure represented by any of —C≡N, —N=C=O,

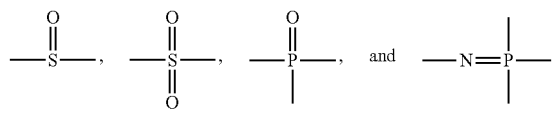

is contained in the compound (9).

The compound (9) is preferably at least one selected from the group consisting of compounds (10) to (17), more preferably at least one selected from the group consisting of compounds (10) and (12) to (17), still more preferably at least one selected from the group consisting of compounds (10) and (12) to (15), particularly preferably at least one selected from the group consisting of compounds (10) and (15), most preferably a compound (10).

The compound (10) is represented by formula (10):

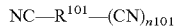
NC—R$^{101}$—(CN)$_{n101}$ wherein R$^{101}$ is a monovalent to trivalent hydrocarbon group or a monovalent to trivalent halogenated hydrocarbon group; and n$^{101}$ is an integer of 0 to 2.

Examples of the hydrocarbon group and the halogenated hydrocarbon group include C1-C10 alkyl groups, C3-C10 cycloalkyl groups, C1-C10 alkylene groups, C3-C10 cycloalkylene groups, C1-C10 alkylidyne groups, and C3-C10 cycloalkylidyne groups. The hydrocarbon group may contain —S(=O)$_2$—, —S(=O)$_2$—O—, or —P=O.

Examples of the cycloalkyl group include a cyclohexyl group. One or all of the hydrogen atoms in the cycloalkyl group may be replaced with —S(=O)$_2$—, —S(=O)$_2$—O—, —P=O, or —OM$^{102}$ (M$^{102}$ is a metal atom).

Examples of the cycloalkylidyne group include a cyclohexylidyne group. One or all of the hydrogen atoms in the cycloalkylidyne group may be replaced with —S(=O)$_2$—, —S(=O)$_2$—O—, —P=O, or —OM$^{102}$ (M$^{102}$ is a metal atom).

The compound (10) is preferably at least one selected from the group consisting of a compound represented by formula (10-1):

R$^{102}$—N wherein R$^{102}$ is a C1-C10 alkyl group or the formula: —R$^{103}$—CN (R$^{103}$ is a C1-C10 alkylene group), a compound represented by formula (10-2):

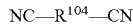
NC—R$^{104}$—CN wherein R$^{104}$ is a C1-C10 alkylene group, and a compound represented by formula (10-3):

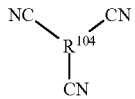

wherein R$^{104}$ is a C1-C10 alkylidyne group or a C3-C10 cycloalkylidyne group. The compound (10) is more preferably at least one selected from the group consisting of a compound represented by formula (10-2) and a compound represented by formula (10-3).

Examples of the compound (10) include acetonitrile, propionitrile, butanenitrile, succinonitrile, glutaronitrile, adiponitrile, octafluoroadiponitrile, 1,3,5-pentanetricarbonitrile, 1,3,6-hexanetricarbonyl, 1,3,5-cyclohexanetricarbonitrile, and CH$_3$SO$_3$C2H$_5$CN. Preferred among them are compounds having multiple CN groups.

The compound (11) is represented by formula (11):

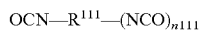
OCN—R$^{111}$—(NCO)$_{n111}$ wherein R$^{111}$ is a monovalent or divalent hydrocarbon group or a monovalent or divalent halogenated hydrocarbon group; and n$^{111}$ is 0 or 1.

Examples of the hydrocarbon group and the halogenated hydrocarbon group include C1-C10 alkyl groups, C1-C10 halogenated alkyl groups, C3-C10 cycloalkyl groups, C1-C10 alkylene groups, C1-C10 halogenated alkyl groups, and C3-C10 cycloalkylene groups.

The compound (11) is preferably at least one selected from the group consisting of a compound represented by formula (11-1):

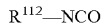
R$^{112}$—NCO wherein R$^{112}$ is a C1-C10 alkyl group which may optionally have a cyclic structure or a C1-C10 halogenated alkyl group which may optionally have a cyclic structure, and a compound represented by formula (11-2):

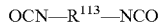
OCN—R$^{113}$—NCO wherein R$^{113}$ is a C1-C10 alkylene group which may optionally have a cyclic structure or a C1-C10 halogenated alkylene group which may optionally have a cyclic structure.

Examples of the compound (11) include hexanemethylene diisocyanate and 1,3-bis(isocyanatomethyl)cyclohexane.

The compound (12) is represented by formula (12):

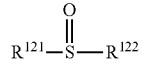

wherein R$^{121}$ and R$^{122}$ may be the same as or different from each other, and are each a halogen atom, a monovalent or divalent hydrocarbon group, or a monovalent or divalent halogenated hydrocarbon group; and R$^{121}$ and R$^{122}$ may be bonded to each other to form a ring.

Examples of the hydrocarbon group and the halogenated hydrocarbon group include C1-C10 alkyl groups, C1-C10 fluorinated alkyl groups, C1-C10 alkoxy groups, C1-C10 fluorinated alkoxy groups, C1-C10 alkylene groups, C1-C10 fluorinated alkylene groups, C1-C10 fluorinated oxyalkylene groups, C2-C10 alkenylidene groups, and C2-C10 fluorinated alkenylidene groups. When the carbon number is 2 or greater, the hydrocarbon group and the halogenated hydrocarbon group may have an ether bond.

The compound (12) is preferably a compound represented by formula (12-1):

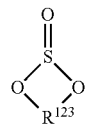

wherein R$^{123}$ is a C2 or C3 alkylene group or a C2 or C3 fluorinated alkylene group.

The compound (13) is represented by formula (13):

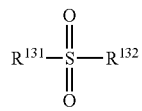

wherein R$^{131}$ and R$^{132}$ may be the same as or different from each other, and are each a halogen atom, a monovalent or divalent hydrocarbon group, or a monovalent or divalent halogenated hydrocarbon group; and R$^{131}$ and R$^{132}$ may be bonded to each other to form a ring.

Examples of the hydrocarbon group and the halogenated hydrocarbon group include C1-C10 alkyl groups, C1-C10 fluorinated alkyl groups, C1-C10 alkoxy groups, C1-C10 fluorinated alkoxy groups, C1-C10 alkylene groups, C1-C10 fluorinated alkylene groups, C1-C10 fluorinated oxyalkylene groups, and C2-C10 alkenylidene groups. When the carbon number is 2 or greater, the hydrocarbon group and the halogenated hydrocarbon group may have an ether bond.

The compound (13) is preferably at least one selected from the group consisting of a compound represented by formula (13-1):

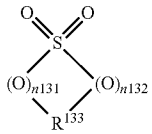

wherein $n^{131}$ is 0 or 1; $n^{132}$ is 0 or 1; and $R^{133}$ is a C2-C6 alkylene group, a C2-C6 fluorinated alkylene group, or a C2-C6 alkenylidene group, and a compound represented by formula (13-2):

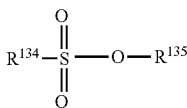

wherein $R^{134}$ is F, a C1-C5 alkyl group, or a C1-C5 fluorinated alkyl group; and $R^{135}$ is F, a C1-C5 alkyl group, or a C1-C5 fluorinated alkyl group.

The compound (14) is represented by formula (14):

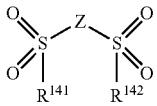

wherein $R^{141}$ and $R^{142}$ may be the same as or different from each other, and are each a halogen atom, a monovalent or divalent hydrocarbon group, or a monovalent or divalent halogenated hydrocarbon group; $R^{141}$ and $R^{142}$ may be bonded to each other to form a ring; and Z is an oxygen atom or a C1-C10 alkylene group.

Examples of the hydrocarbon group and the halogenated hydrocarbon group include C1-C10 alkyl groups, C1-C10 fluorinated alkyl groups, C1-C10 alkoxy groups, C1-C10 fluorinated alkoxy groups, C1-C10 alkylene groups, C1-C10 fluorinated alkylene groups, and C1-C10 fluorinated oxyalkylene groups. When the carbon number is 2 or greater, the hydrocarbon group and the halogenated hydrocarbon group may have an ether bond.

The compound (14) is preferably at least one selected from the group consisting of a compound represented by formula (14-1):

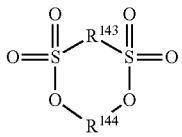

wherein $R^{143}$ and $R^{144}$ may be the same as or different from each other, and are each a C1-C3 alkylene group, and a compound represented by formula (14-2):

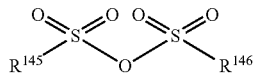

wherein $R^{145}$ and $R^{146}$ may be the same as or different from each other, and are each a C1-C3 alkyl group.

Examples of the compound (12) to (14) include 1,3-propane sultone, 2,4-butane sultone, 1,4-butane sultone, 1,3-propene sultone, methanesulfonic anhydride, propyl methanesulfonate, tetrafluoropropyl methanesulfonate, dimethyl sulfoxide, sulfolane, ethylene sulfite, sulfuric acid glycol, methylene methanedisulfonate, 3-fluoro sulfolane, 3-fluoro-1,3-propane sultone, and monofluorosulfuric acid glycol.

The compound (15) is represented by formula (15):

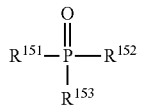

wherein $R^{151}$ to $R^{153}$ may be the same as or different from each other, and are each an organic group.

Examples of the organic group include C1-C10 alkyl groups, C1-C10 fluorinated alkyl groups, C1-C10 alkoxy groups, C1-C10 fluorinated alkoxy groups, groups represented by the formula: $—N(R^{154})_2$, groups represented by the formula: $—Si(R^{155})_3$, groups represented by the formula $—OSi(R^{156})_3$, groups represented by the formula $—R^{158}—S—R^{157}$, and groups represented by the formula: $—O—R^{159}—CN$.

$R^{154}$ to $R^{157}$ are each a C1-C4 alkyl group or a C1-C4 fluorinated alkyl group. $R^{158}$ and $R^{159}$ are each a C1-C3 alkylene group or a C1-C3 fluorinated alkyl group.

Examples of the compound (15) include $(CH_3CH_2O)_3P=O$, $(CF_3CH_2O)_3P=O$, $(CF_3CF_2CH_2O)_3P=O$, $(HCF_2CF_2CH_2O)_3P=O$, $(CH_3CH_2O)_2(CH_3CH_2)P=O$, $(CH_3CH_2)_2(CH_3O)P=O$, $[(CH_3)_2N]3P=O$, $[(CH_3)_3Si](CH_3O)_2P=O$, $[(CH_3)SiO]_3P=O$, $[(CH_3CH_2)_2]_2(CH_3CH_2SCH_2)P=O$, and $(CF_3CH_2O)_2(NCCH_2CH_2O)P=O$.

The compound (16) is represented by formula (16):

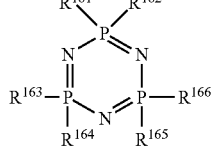

wherein $R^{161}$ to $R^{166}$ may be the same as or different from each other, and are each a halogen atom or an organic group.

The halogen atom is preferably F. Examples of the organic group include alkoxy groups such as methoxy and ethoxy groups, aryloxy groups such as phenoxy and methyl phenoxy groups, alkyl groups such as methyl and ethyl groups, aryl groups such as phenyl and tolyl groups, amino groups including substituted amino groups such as a methyl amino group, alkylthio groups such as methylthio and ethylthio groups, and arylthio groups such as a phenylthio group.

Examples of the compound (16) include hexafluorocyclotriphosphazene, pentafluoro (phenoxy)cyclotriphosphazene, ethoxy(pentafluoro)cyclotriphosphazene, and ethoxy (heptafluoro)cyclotriphosphazene.

The compound (17) is represented by formula (17):

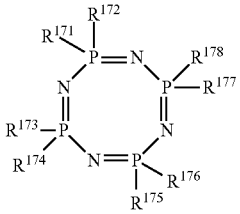

wherein $R^{171}$ to $R^{178}$ may be the same as or different from each other, and are each a halogen atom or an organic group.

The halogen atom is preferably F. Examples of the organic group include alkoxy groups such as methoxy and ethoxy groups, aryloxy groups such as phenoxy and methyl phenoxy groups, alkyl groups such as methyl and ethyl groups, aryl groups such as phenyl and tolyl groups, amino groups including substituted amino groups such as a methyl amino group, alkylthio groups such as methylthio and ethylthio groups, and arylthio groups such as a phenylthio group.

Examples of the compound (17) include ethoxy(pentafluoro)cyclotetraphosphazene.

The electrolytic solution of the present invention preferably contains a solvent.

The amount of the solvent in the electrolytic solution is preferably 70 to 99.999 mass %, more preferably 80 mass % or more, while more preferably 92 mass % or less.

The solvent preferably contains a carbonate.

The solvent preferably contains a cyclic carbonate and an acyclic carbonate.

The cyclic carbonate may be a non-fluorinated cyclic carbonate or may be a fluorinated cyclic carbonate.

The acyclic carbonate may be a non-fluorinated acyclic carbonate or may be a fluorinated acyclic carbonate. The solvent preferably contains at least one selected from the group consisting of non-fluorinated saturated cyclic carbonates, fluorinated saturated cyclic carbonates, fluorinated acyclic carbonates, and non-fluorinated acyclic carbonates. In particular, the solvent more preferably contains at least one selected from the group consisting of fluorinated saturated cyclic carbonates and fluorinated acyclic carbonates.

The solvent is preferably a non-aqueous solvent and the electrolytic solution of the present invention is preferably a non-aqueous electrolytic solution.

Examples of the non-fluorinated saturated cyclic carbonates include ethylene carbonate (EC), propylene carbonate (PC), and butylene carbonate.

In order to achieve a high permittivity and a suitable viscosity, the non-fluorinated saturated cyclic carbonate is preferably at least one compound selected from the group consisting of ethylene carbonate, propylene carbonate, and butylene carbonate.

The non-fluorinated saturated cyclic carbonate may include one of the above compounds or may include two or more thereof in combination.

The amount of the non-fluorinated saturated cyclic carbonate relative to the solvent is preferably 0 to 99 vol %, more preferably 1 vol % or more, while more preferably 90 vol % or less.

The fluorinated saturated cyclic carbonate is a saturated cyclic carbonate with a fluorine atom attached thereto. Specific examples thereof include a compound represented by formula (A) below:

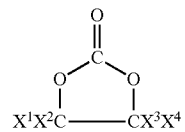

wherein $X^1$ to $X^4$ may be the same as or different from each other, and are individually —H, —CH$_3$, —F, a fluorinated alkyl group which may optionally have an ether bond, or a fluorinated alkoxy group which may optionally have an ether bond; at least one of $X^1$ to $X^4$ is —F, a fluorinated alkyl group which may optionally have an ether bond, or a fluorinated alkoxy group which may optionally have an ether bond.

If the electrolytic solution of the present invention contains the fluorinated saturated cyclic carbonate and is applied to a lithium ion secondary battery, a stable film is formed on the negative electrode so that side reactions of the electrolytic solution on the negative electrode may sufficiently be suppressed. As a result, significantly stable, excellent charge and discharge characteristics can be achieved.

The term "ether bond" herein means a bond represented by —O—.

In order to achieve a good permittivity and oxidation resistance, one or two of $X^1$ to $X^4$ is/are preferably —F, a fluorinated alkyl group which may optionally have an ether bond, or a fluorinated alkoxy group which may optionally have an ether bond.

In anticipation of a decrease in the viscosity at low temperatures, an increase in the flash point, and improvement in the solubility of the electrolyte salt, $X^1$ to $X^4$ are preferably individually —H, —F, a fluorinated alkyl group (a), a fluorinated alkyl group (b) having an ether bond, or a fluorinated alkoxy group (c).

The fluorinated alkyl group (a) is an alkyl group in which at least one hydrogen atom is replaced by a fluorine atom. The fluorinated alkyl group (a) preferably has a carbon number of 1 to 20, more preferably 1 to 17, still more preferably 1 to 7, particularly preferably 1 to 5.

If the carbon number is too large, the low-temperature characteristics may be poor and the solubility of the electrolyte salt may be low. If the carbon number is too small, the solubility of the electrolyte salt may be low, the discharge efficiency may be low, and the viscosity may be high, for example.

Examples of the fluorinated alkyl group (a) which has a carbon number of 1 include CFH$_2$—, CF$_2$H—, and CF$_3$—.

In order to achieve a good solubility of the electrolyte salt, preferred examples of the fluorinated alkyl group (a) which has a carbon number of 2 or greater include fluorinated alkyl groups represented by formula (a-1) below:

$$R^1\text{-}R^2\text{—} \tag{a-1}$$

wherein $R^1$ is an alkyl group which may optionally have a fluorine atom and which has a carbon number of 1 or greater; $R^2$ is a C1-C3 alkylene group which may optionally have a fluorine atom; and at least one of $R^1$ and $R^2$ has a fluorine atom.

$R^1$ and $R^2$ each may further have an atom other than the carbon atom, hydrogen atom, and fluorine atom.

$R^1$ is an alkyl group which may optionally have a fluorine atom and which has a carbon number of 1 or greater.

$R^1$ is preferably a C1-C16 linear or branched alkyl group. The carbon number of $R^1$ is more preferably 1 to 6, still more preferably 1 to 3.

Specifically, for example, CH$_3$—, CH$_3$CH$_2$—, CH$_3$CH$_2$CH$_2$—, CH$_3$CH$_2$CH$_2$CH$_2$—, and the groups represented by the following formulas:

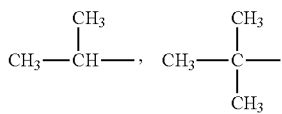

may be mentioned as linear or branched alkyl groups for R$^1$.

If R$^1$ is a linear alkyl group having a fluorine atom, examples thereof include CF$_3$—, CF$_3$CH$_2$—, CF$_3$CF$_2$—, CF$_3$CH$_2$CH$_2$—, CF$_3$CF$_2$CH$_2$—, CF$_3$CF$_2$CF$_2$—, CF$_3$CH$_2$CF$_2$—, CF$_3$CH$_2$CH$_2$CH$_2$—, CF$_3$CF$_2$CH$_2$CH$_2$—, CF$_3$CF$_2$CF$_2$CH$_2$—, CF$_3$CF$_2$CF$_2$CF$_2$—, CF$_3$CF$_2$CH$_2$CF$_2$—, CF$_3$CH$_2$CH$_2$CH$_2$CH$_2$—, CF$_3$CF$_2$CH$_2$CH$_2$CH$_2$—, CF$_3$CH$_2$CF$_2$CH$_2$CH$_2$—, CF$_3$CF$_2$CF$_2$CH$_2$CH$_2$—, CF$_3$CF$_2$CF$_2$CF$_2$CH$_2$—, CF$_3$CF$_2$CH$_2$CF$_2$CH$_2$—, CF$_3$CF$_2$CH$_2$CH$_2$CH$_2$CH$_2$—, CF$_3$CF$_2$CF$_2$CH$_2$CH$_2$CH$_2$—, CF$_3$CF$_2$CH$_2$CF$_2$CH$_2$CH$_2$—, HCF$_2$—, HCF$_2$CH$_2$—, HCF$_2$CF$_2$—, HCF$_2$CH$_2$CH$_2$—, HCF$_2$CF$_2$CH$_2$—, HCF$_2$CH$_2$CF$_2$—, HCF$_2$CF$_2$CH$_2$CH$_2$—, HCF$_2$CH$_2$CF$_2$CH$_2$—, HCF$_2$CF$_2$CF$_2$CF$_2$—, HCF$_2$CF$_2$CH$_2$CH$_2$CH$_2$—, HCF$_2$CH$_2$CF$_2$CH$_2$CH$_2$—, HCF$_2$CF$_2$CF$_2$CF$_2$CH$_2$—, HCF$_2$CF$_2$CF$_2$CH$_2$CH$_2$—, FCH$_2$—, FCH$_2$CH$_2$—, FCH$_2$CF$_2$—, FCH$_2$CF$_2$CH$_2$—, FCH$_2$CF$_2$CF$_2$—, CH$_3$CF$_2$CH$_2$—, CH$_3$CF$_2$CF$_2$—, CH$_3$CF$_2$CH$_2$CF$_2$—, CH$_3$CF$_2$CF$_2$CF$_2$—, CH$_3$CH$_2$CF$_2$CF$_2$—, CH$_3$CF$_2$CH$_2$CF$_2$CH$_2$—, CH$_3$CF$_2$CF$_2$CF$_2$CH$_2$—, CH$_3$CF$_2$CH$_2$CF$_2$CH$_2$—, CH$_3$CH$_2$CF$_2$CF$_2$CH$_2$—, CH$_3$CF$_2$CH$_2$CF$_2$CH$_2$CH$_2$—, CH$_3$CF$_2$CH$_2$CF$_2$CH$_2$CH$_2$—, HCFClCF$_2$CH$_2$—, HCF$_2$CFClCH$_2$—, HCF$_2$CFClCF$_2$CFClCH$_2$—, and HCFClCF$_2$CFClCF$_2$CH$_2$—.

If R$^1$ is a branched alkyl group having a fluorine atom, those represented by the following formulas:

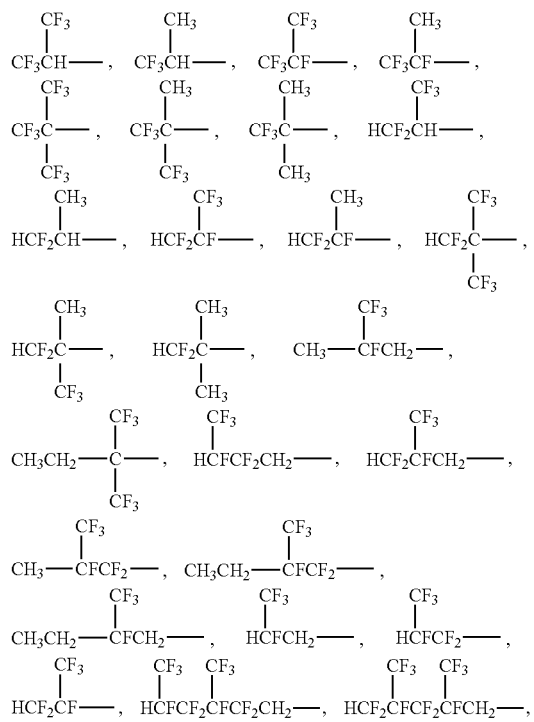

-continued

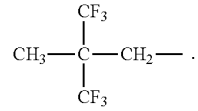

may be preferably mentioned. If the group has a branch represented by CH$_3$— or CF$_3$—, for example, the viscosity is likely to be high. Thus, the number of such branches is more preferably small (one) or zero.

R$^2$ is a C1-C3 alkylene group which may optionally have a fluorine atom. R$^2$ may be a linear or branched group. Examples of a minimum structural unit constituting such a linear or branched alkylene group are shown below. R$^2$ is constituted by one or combination of these units.

(i) Linear minimum structural units

—CH$_2$—, —CHF—, —CF$_2$—, —CHCl—, —CFCl—, —CCl$_2$—

(ii) Branched minimum structural units

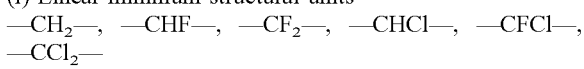

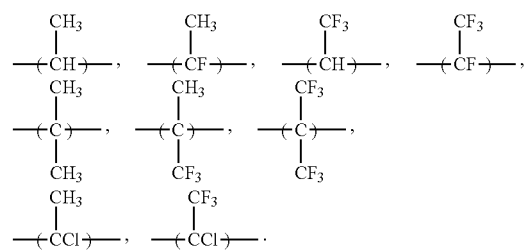

Preferred among these exemplified units are Cl-free structural units because such units are not dehydrochlorinated by a base, and thus are more stable.

If R$^2$ is a linear group, the group consists only of any of the above linear minimum structural units, preferably —CH$_2$—, —CH$_2$CH$_2$—, or —CF$_2$—. In order to further improve the solubility of the electrolyte salt, —CH$_2$— or —CH$_2$CH$_2$— is more preferred.

If R$^2$ is a branched group, the group includes at least one of the above branched minimum structural units. Preferred examples thereof include those represented by the formula: —(CX$^a$X$^b$)— (wherein X$^a$ is H, F, CH$_3$, or CF$_3$; X$^b$ is CH$_3$ or CF$_3$; if X$^b$ is CF$_3$, X$^a$ is H or CH$_3$). Such groups can much further improve the solubility of the electrolyte salt.

For example, CF$_3$CF$_2$—, HCF$_2$CF$_2$—, H$_2$CFCF$_2$—, CH$_3$CF$_2$—, CF$_3$CHF—, CF$_3$CF$_2$CF$_2$—, HCF$_2$CF$_2$CF$_2$—, H$_2$CFCF$_2$CF$_2$—, CH$_3$CF$_2$CF$_2$—, and those represented by the following formulas:

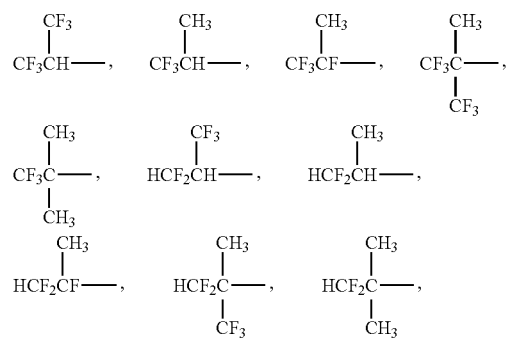

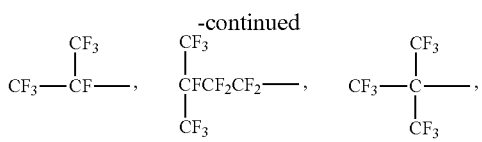

may be mentioned as preferred fluorinated alkyl groups (a).

The fluorinated alkyl group (b) having an ether bond is an alkyl group which has an ether bond and in which at least one hydrogen atom is replaced by a fluorine atom. The fluorinated alkyl group (b) having an ether bond preferably has a carbon number of 2 to 17. If the carbon number is too large, the fluorinated saturated cyclic carbonate may have a high viscosity, and also the number of fluorine-containing groups may be large. Thus, the solubility of the electrolyte salt may be poor due to reduction in the permittivity, and the compatibility with other solvents may be poor. Accordingly, the carbon number of the fluorinated alkyl group (b) having an ether bond is preferably 2 to 10, more preferably 2 to 7.

The alkylene group which constitutes the ether segment of the fluorinated alkyl group (b) having an ether bond may be a linear or branched alkylene group. Examples of a minimum structural unit constituting such a linear or branched alkylene group are shown below.

(i) Linear Minimum Structural Units

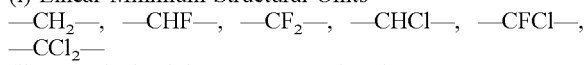

(ii) Branched Minimum Structural Units

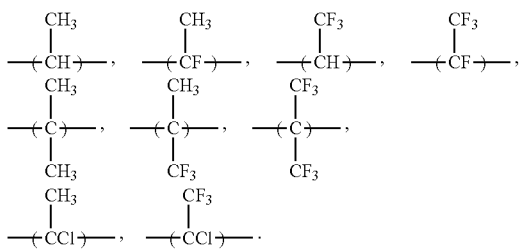

The alkylene group may be constituted by one of these minimum structural units alone, or may be constituted by multiple linear units (i), by multiple branched units (ii), or by a combination of a linear unit (i) and a branched unit (ii). Preferred examples will be mentioned in detail later.

Preferred among these exemplified units are Cl-free structural units because such units are not dehydrochlorinated by a base, and thus are more stable.

Still more preferred examples of the fluorinated alkyl group (b) having an ether bond include those represented by formula (b-1):

$$R^3—(OR^4)_{n1}— \quad (b\text{-}1)$$

wherein $R^3$ is preferably a C1-C6 alkyl group which may optionally have a fluorine atom; $R^4$ is preferably a C1-C4 alkylene group which may optionally have a fluorine atom; n1 is an integer of 1 to 3; and at least one of $R^3$ and $R^4$ has a fluorine atom.

Examples of the groups for $R^3$ and $R^4$ include the following, and any appropriate combination of these groups can provide the fluorinated alkyl group (b) having an ether bond represented by formula (b-1). Still, the groups are not limited thereto.

(1) $R^3$ is preferably an alkyl group represented by the formula: $X^c{}_3C—(R^5)_{n2}—$, where three $X^c$s may be the same as or different from each other, and are individually H or F;

$R^5$ is a C1-C5 alkylene group which may optionally have a fluorine atom; and n2 is 0 or 1.

If n2 is 0, $R^3$ may be $CH_3—$, $CF_3—$, $HCF_2—$, or $H_2CF—$, for example.

If n2 is 1, specific examples of linear groups for $R^3$ include $CF_3CH_2—$, $CF_3CF_2—$, $CF_3CH_2CH_2—$, $CF_3CF_2CH_2—$, $CF_3CF_2CF_2—$, $CF_3CH_2CF_2—$, $CF_3CH_2CH_2CH_2—$, $CF_3CF_2CH_2CH_2—$, $CF_3CH_2CF_2CH_2—$, $CF_3CF_2CF_2CH_2—$, $CF_3CF_2CH_2CF_2—$, $CF_3CH_2CH_2CH_2CH_2—$, $CF_3CF_2CH_2CH_2CH_2—$, $CF_3CH_2CF_2CH_2CH_2—$, $CF_3CF_2CF_2CH_2CH_2—$, $CF_3CF_2CF_2CF_2CH_2—$, $CF_3CF_2CH_2CF_2CH_2—$, $CF_3CH_2CH_2CH_2CH_2—$, $CF_3CF_2CF_2CF_2CH_2CH_2—$, $CF_3CF_2CH_2CF_2CH_2CH_2—$, $HCF_2CH_2—$, $HCF_2CF_2—$, $HCF_2CH_2CH_2—$, $HCF_2CF_2CH_2—$, $HCF_2CH_2CF_2—$, $HCF_2CF_2CH_2CH_2—$, $HCF_2CH_2CF_2CH_2—$, $HCF_2CF_2CF_2CF_2—$, $HCF_2CF_2CH_2CH_2CH_2—$, $HCF_2CH_2CF_2CH_2CH_2—$, $HCF_2CF_2CF_2CF_2CH_2—$, $HCF_2CF_2CF_2CF_2CH_2CH_2—$, $FCH_2CH_2—$, $FCH_2CF_2—$, $FCH_2CF_2CH_2—$, $CH_3CF_2—$, $CH_3CH_2—$, $CH_3CF_2CH_2—$, $CH_3CF_2CF_2—$, $CH_3CH_2CH_2—$, $CH_3CF_2CH_2CF_2—$, $CH_3CF_2CF_2CF_2—$, $CH_3CH_2CF_2CF_2—$, $CH_3CH_2CH_2CH_2—$, $CH_3CF_2CH_2CF_2CH_2—$, $CH_3CF_2CF_2CF_2CH_2—$, $CH_3CF_2CF_2CH_2CH_2—$, $CH_3CH_2CF_2CF_2CH_2—$, $CH_3CF_2CH_2CF_2CH_2CH_2—$, $CH_3CH_2CF_2CF_2CH_2CH_2—$, and $CH_3CF_2CH_2CF_2CH_2CH_2—$.

If n2 is 1, those represented by the following formulas:

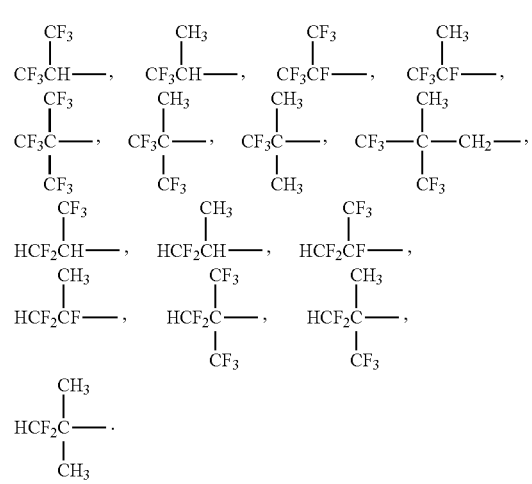

may be mentioned as branched groups for $R^3$.

If the group for $R^3$ has a branch such as $CH_3—$ or $CF_3—$, the viscosity is likely to be high. Thus, the group for $R^3$ is more preferably a linear group.

(2) In the segment $—(OR^4)_{n1}—$ of formula (b-1), n1 is an integer of 1 to 3, preferably 1 or 2. If n1 is 2 or 3, $R^4$s may be the same as or different from each other.

Preferred specific examples of the group for $R^4$ include the following linear or branched groups.

Examples of the linear groups include $—CH_2—$, $—CHF—$, $—CF_2—$, $—CH_2CH_2—$, $—CF_2CH_2—$, $—CF_2CF_2—$, $—CH_2CF_2—$, $—CH_2CH_2CH_2—$, $—CH_2CH_2CF_2—$, $—CH_2CF_2CH_2—$, $—CH_2CF_2CF_2—$, $—CF_2CH_2CH_2—$, $—CF_2CF_2CH_2—$, $—CF_2CH_2CF_2—$, and $—CF_2CF_2CF_2—$.

Those represented by the following formulas:

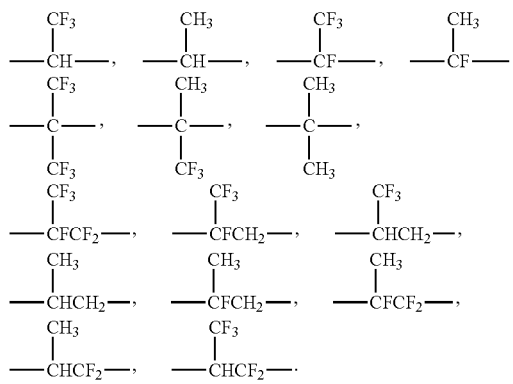

may be mentioned as branched groups.

The fluorinated alkoxy group (c) is an alkoxy group in which at least one hydrogen atom is replaced by a fluorine atom. The fluorinated alkoxy group (c) preferably has a carbon number of 1 to 17. The carbon number is more preferably 1 to 6.

The fluorinated alkoxy group (c) is particularly preferably a fluorinated alkoxy group represented by the formula: $X^d_3C-(R^6)_{n3}-O-$ (wherein three $X^d$s may be the same as or different from each other, and are individually H or F; $R^6$ is preferably a C1-C5 alkylene group which may optionally have a fluorine atom; n3 is 0 or 1; and any one of the three $X^d$s contains a fluorine atom).

Specific examples of the fluorinated alkoxy group (c) include fluorinated alkoxy groups in which an oxygen atom is bonded to an end of the alkyl group for $R^1$ in formula (a-1).

The fluorinated alkyl group (a), the fluorinated alkyl group (b) having an ether bond, and the fluorinated alkoxy group (c) in the fluorinated saturated cyclic carbonate each preferably have a fluorine content of 10 mass % or more. If the fluorine content is too low, an effect of decreasing the viscosity at low temperature and an effect of increasing the flash point may not be sufficiently achieved. Thus, the fluorine content is more preferably 12 mass % or more, still more preferably 15 mass % or more. The upper limit thereof is usually 76 mass %.

The fluorine content of each of the fluorinated alkyl group (a), the fluorinated alkyl group (b) having an ether bond, and the fluorinated alkoxy group (c) is a value calculated by the following formula:

{(Number of fluorine atoms×19)/(formula weight of the formula)}×100(%)

based on the corresponding structural formula.

In order to achieve a good permittivity and oxidation resistance, the fluorine content in the whole fluorinated saturated cyclic carbonate is preferably 10 mass % or more, more preferably 15 mass % or more. The upper limit thereof is usually 76 mass %.

The fluorine content in the fluorinated saturated cyclic carbonate is a value calculated by the following formula: {(Number of fluorine atoms×19)/(molecular weight of fluorinated saturated cyclic carbonate}×100(%), based on the structural formula of the fluorinated saturated cyclic carbonate.

Specific examples of the fluorinated saturated cyclic carbonate include the following.

Those represented by the following formulas:

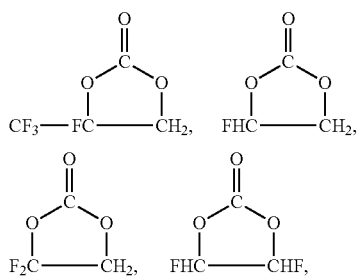

may be mentioned as specific examples of the fluorinated saturated cyclic carbonate in which at least one of $X^1$ to $X^4$ is —F. These compounds have a high withstand voltage and give a good solubility of the electrolyte salt.

Alternatively, those represented by the following formulas:

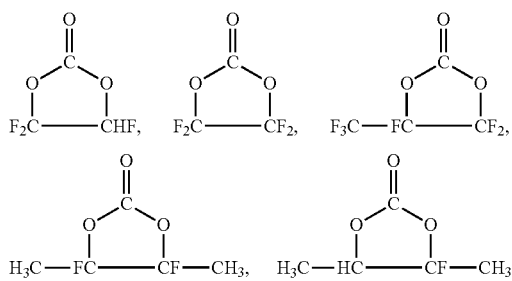

may also be used.

Those represented by the following formulas:

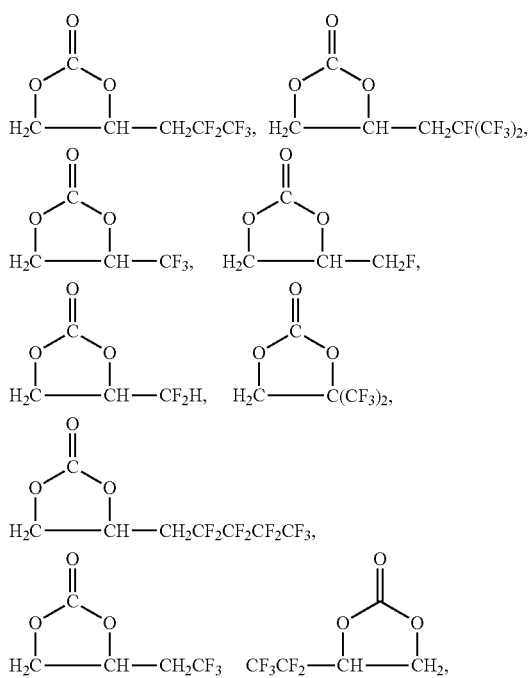

-continued
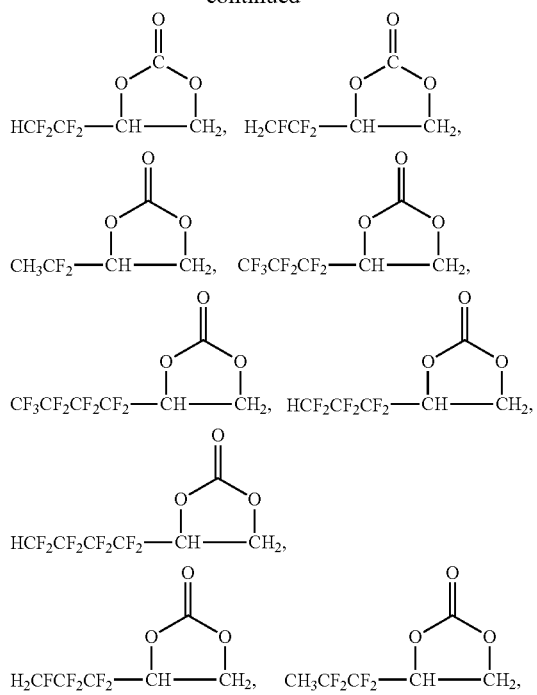
may be mentioned as specific examples of the fluorinated saturated cyclic carbonate in which at least one of $X^1$ to $X^4$ is a fluorinated alkyl group (a) and the others thereof are —H.
Those represented by the following formulas:
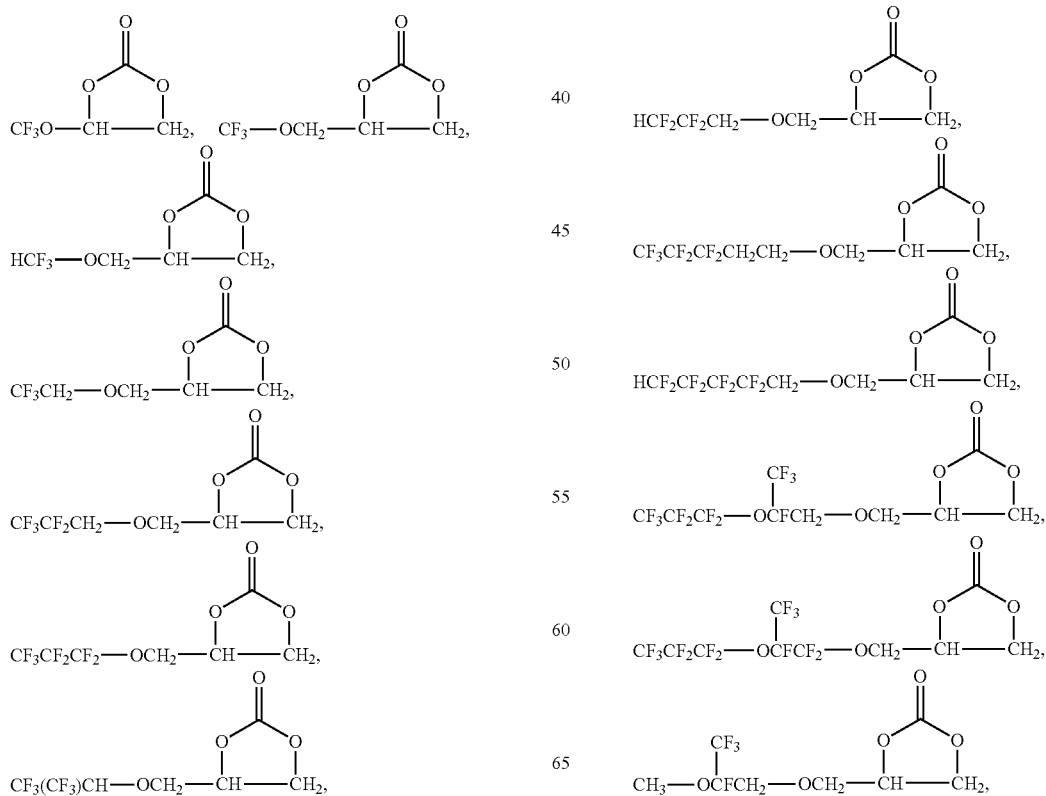

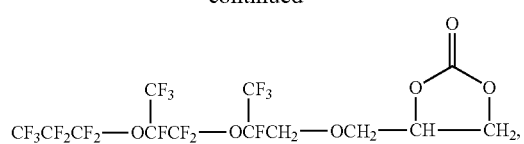
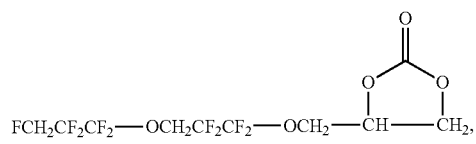
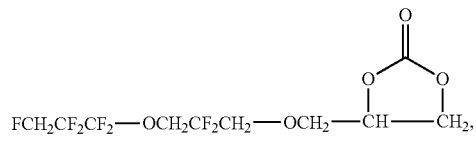
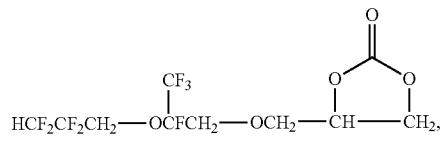
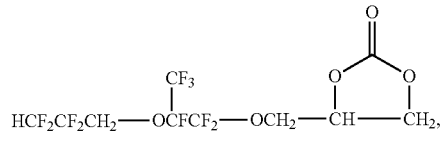
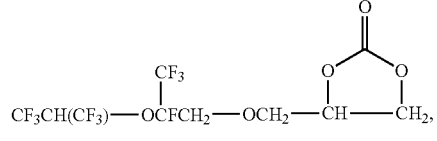
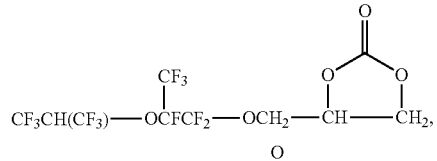
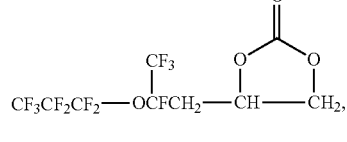
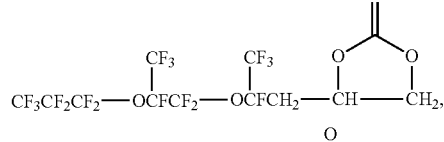
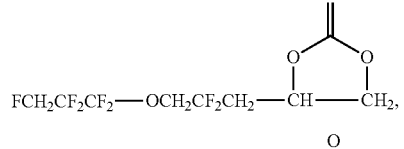
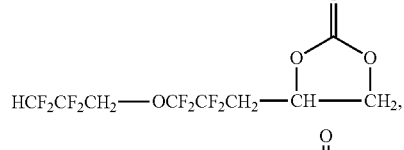
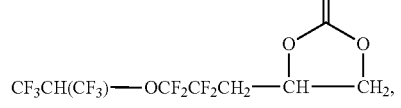
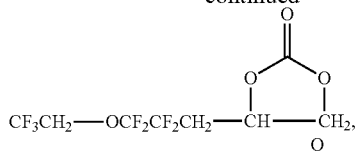
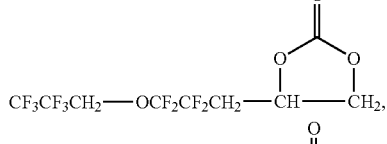
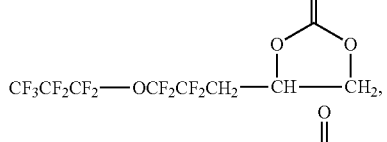
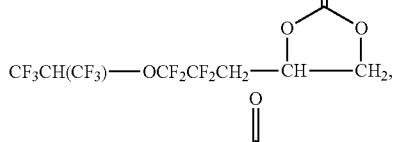
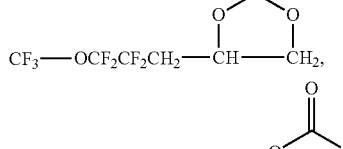
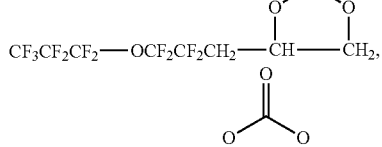
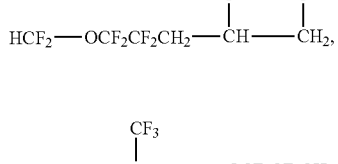
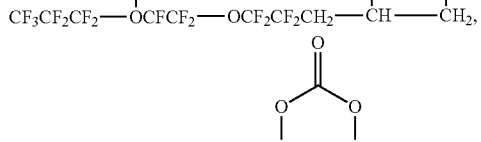
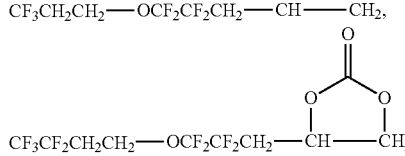
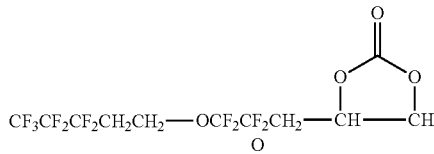
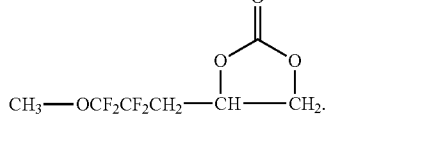
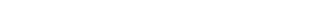
may be mentioned as specific examples of the fluorinated saturated cyclic carbonate in which at least one of $X^1$ to $X^4$ is a fluorinated alkyl group (b) having an ether bond or a fluorinated alkoxy group (c) and the others thereof are —H.

In particular, the fluorinated saturated cyclic carbonate is preferably any of the following compounds.

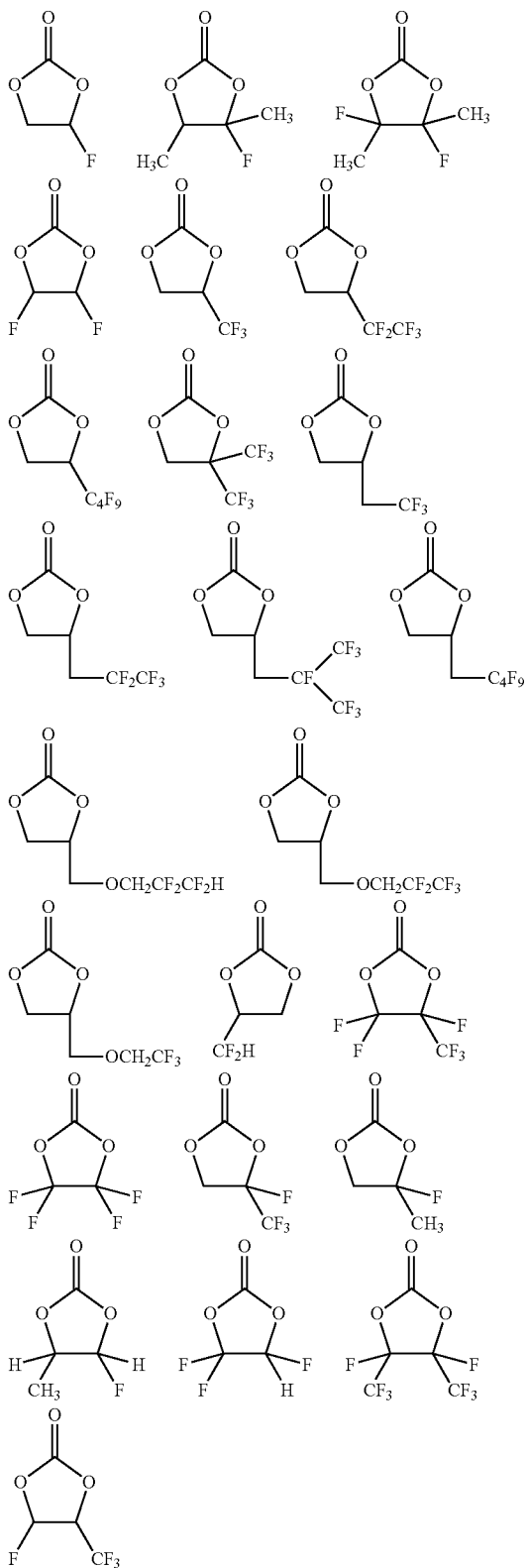

The fluorinated saturated cyclic carbonate is more preferably fluoroethylene carbonate or difluoroethylene carbonate.

The fluorinated saturated cyclic carbonate is not limited to the above specific examples. One of the above fluorinated saturated cyclic carbonates may be used alone, or two or more thereof may be used in any combination at any ratio. For example, a combination of fluoroethylene carbonate and trifluoroethylene carbonate may be used.

The amount of the fluorinated saturated cyclic carbonate in the solvent is preferably 0 to 99 vol %, more preferably 1 vol % or more, still more preferably 5 vol % or more, while more preferably 95 vol % or less, still more preferably 90 vol % or less.

Examples of the fluorinated acyclic carbonate include compounds represented by formula (B):

$$Rf^2OCOOR^6 \qquad (B)$$

wherein $Rf^2$ is a C1-C7 fluorinated alkyl group; and $R^6$ is a C1-C7 alkyl group which may optionally have a fluorine atom.

In order to achieve suitable use under high voltage, the electrolytic solution of the present invention preferably contains the fluorinated acyclic carbonate.

$Rf^2$ is a C1-C7 fluorinated alkyl group and $R^6$ is a C1-C7 alkyl group which may optionally have a fluorine atom.

The fluorinated alkyl group refers to an alkyl group in which at least one hydrogen atom is replaced by a fluorine atom. If $R^6$ is an alkyl group having a fluorine atom, it is a fluorinated alkyl group.

In order to achieve a low viscosity, $Rf^2$ and $R^6$ each preferably have a carbon number of 2 to 7, more preferably 2 to 4.

If the carbon number is too large, the low-temperature characteristics may be poor or the solubility of the electrolyte salt may be low. If the carbon number is too small, the solubility of the electrolyte salt may be low, the discharge efficiency may be low, and the viscosity may be high, for example.

Examples of the fluorinated alkyl group which has a carbon number of 1 include $CFH_2-$, $CF_2H-$, and $CF_3-$.

In order to achieve a good solubility of the electrolyte salt, preferred examples of the fluorinated alkyl group which has a carbon number of 2 or greater include fluorinated alkyl groups represented by formula (d-1) below:

$$R^1\text{-}R^2\text{---} \qquad (d\text{-}1)$$

wherein $R^1$ is an alkyl group which may optionally have a fluorine atom and which has a carbon number of 1 or greater; $R^2$ is a C1-C3 alkylene group which may optionally have a fluorine atom; and at least one of $R^1$ and $R^2$ has a fluorine atom.

$R^1$ and $R^2$ each may further have an atom other than the carbon atom, hydrogen atom, and fluorine atom. $R^1$ is an alkyl group which may optionally have a fluorine atom and which has a carbon number of 1 or greater. $R^1$ preferably is a C1-C6 linear or branched alkyl group. The carbon number of $R^1$ is more preferably 1 to 4, still more preferably 1 to 3.

Specifically, for example, $CH_3-$, $CH_3CH_2-$, $CH_3CH_2CH_2-$, $CH_3CH_2CH_2CH_2-$, and the groups represented by the following formulas:

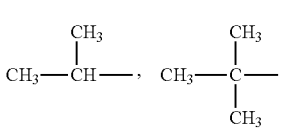

may be mentioned as linear or branched alkyl groups for $R^1$.

If $R^1$ is a linear alkyl group having a fluorine atom, examples thereof include $CF_3$—, $CF_3CH_2$—, $CF_3CF_2$—, $CF_3CH_2CH_2$—, $CF_3CF_2CH_2$—, $CF_3CF_2CF_2$—, $CF_3CH_2CF_2$—, $CF_3CH_2CH_2CH_2$—, $CF_3CF_2CH_2CH_2$—, $CF_3CH_2CF_2CH_2$—, $CF_3CF_2CF_2CH_2$—, $CF_3CF_2CF_2CF_2$—, $CF_3CF_2CH_2CF_2$—, $CF_3CH_2CH_2CH_2CH_2$—, $CF_3CF_2CH_2CH_2CH_2$—, $CF_3CH_2CF_2CH_2CH_2$—, $CF_3CF_2CF_2CH_2CH_2$—, $CF_3CF_2CH_2CF_2CH_2$—, $CF_3CF_2CH_2CF_2CH_2$—, $CF_3CF_2CF_2CF_2CH_2$—, $CF_3CF_2CF_2CH_2CH_2CH_2$—, $CF_3CH_2CF_2CH_2CH_2CH_2$—, $HCF_2$—, $HCF_2CH_2$—, $HCF_2CF_2$—, $HCF_2CH_2CH_2$—, $HCF_2CF_2CH_2$—, $HCF_2CH_2CF_2$—, $HCF_2CF_2CH_2CH_2$—, $HCF_2CH_2CF_2CH_2$—, $HCF_2CF_2CF_2CF_2$—, $HCF_2CF_2CH_2CH_2CH_2$—, $HCF_2CF_2CH_2CF_2CH_2$—, $HCF_2CF_2CF_2CF_2CH_2$—, $HCF_2CF_2CF_2CF_2CH_2CH_2$—, $FCH_2$—, $FCH_2CH_2$—, $FCH_2CF_2$—, $FCH_2CF_2CH_2$—, $FCH_2CF_2CF_2$—, $CH_3CF_2CH_2$—, $CH_3CF_2CF_2$—, $CH_3CF_2CH_2CF_2$—, $CH_3CF_2CF_2CF_2$—, $CH_3CH_2CF_2CF_2$—, $CH_3CF_2CH_2CF_2CH_2$—, $CH_3CF_2CF_2CF_2CH_2$—, $CH_3CF_2CH_2CF_2CH_2$—, $CH_3CH_2CF_2CF_2CH_2$—, $CH_3CF_2CH_2CF_2CH_2CH_2$—, $HCFClCF_2CH_2$—, $HCF_2CFClCH_2$—, $HCF_2CFClCF_2CFClCH_2$—, and $HCFClCF_2CFClCF_2CH_2$—.

If $R^1$ is a branched alkyl group having a fluorine atom, those represented by the following formulas:

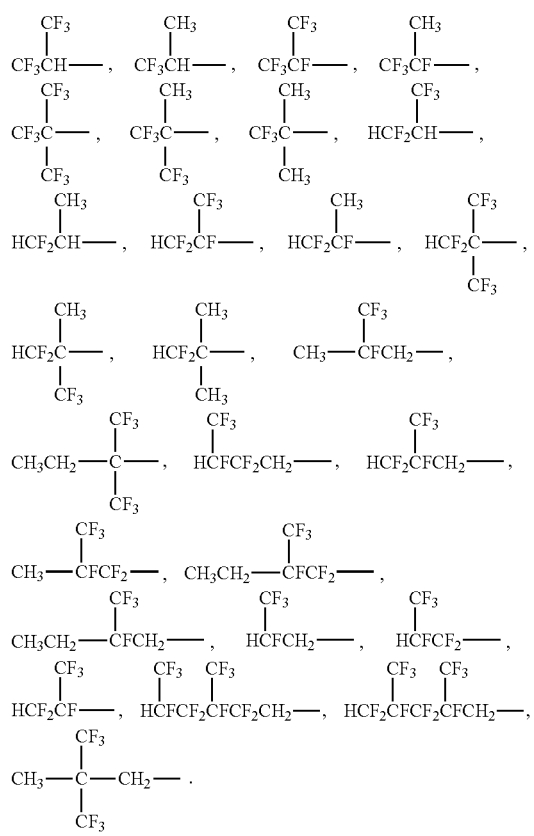

may be preferably mentioned. If the group has a branch represented by $CH_3$— or $CF_3$—, for example, the viscosity is likely to be high. Thus, the number of such branches is more preferably small (one) or zero.

$R^2$ is a C1-C3 alkylene group which may optionally have a fluorine atom. $R^2$ may be a linear or branched group. Examples of a minimum structural unit constituting such a linear or branched alkylene group are shown below. $R^2$ is constituted by one or combination of these units.

(i) Linear Minimum Structural Units

—$CH_2$—, —CHF—, —$CF_2$—, —CHCl—, —CFCl—, —$CCl_2$—

(ii) Branched Minimum Structural Units

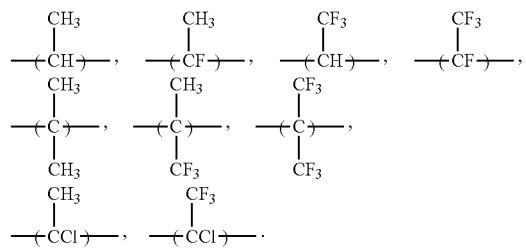

Preferred among these exemplified units are Cl-free structural units because such units are not dehydrochlorinated by a base, and thus are more stable.

If $R^2$ is a linear group, the group consists only of any of the above linear minimum structural units, and it is preferably —$CH_2$—, —$CH_2CH_2$—, or $CF_2$—. In order to further improve the solubility of the electrolyte salt, —$CH_2$— or —$CH_2CH_2$— is more preferred.

If $R^2$ is a branched group, the group includes at least one of the above branched minimum structural units. Preferred examples thereof include those represented by the formula —($CX^aX^b$)— (wherein $X^a$ is H, F, $CH_3$, or $CF_3$; $X^b$ is $CH_3$ or $CF_3$; if $X^b$ is $CF_3$, $X^a$ is H or $CH_3$). Such groups can much further improve the solubility of the electrolyte salt.

For example, $CF_3CF_2$—, $HCF_2CF_2$—, $H_2CFCF_2$—, $CH_3CF_2$—, $CF_3CH_2$—, $CF_3CF_2CF_2$—, $HCF_2CF_2CF_2$—, $H_2CFCF_2CF_2$—, $CH_3CF_2CF_2$—, and those represented by the following formulas:

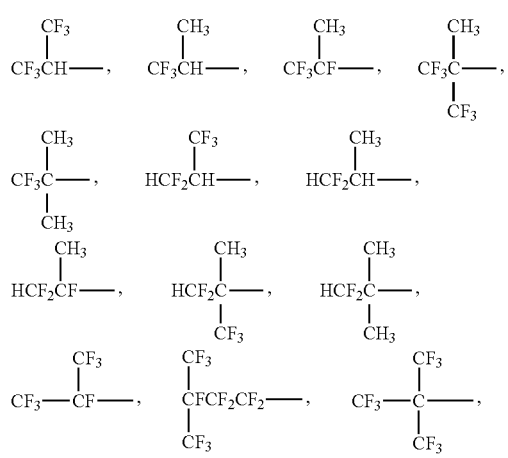

may be specifically mentioned as a preferred fluorinated alkyl group.

In particular, the fluorinated alkyl group for $Rf^2$ and $R^6$ is preferably $CF_3$—, $CF_3CF_2$—, $(CF_3)_2CH$—, $CF_3CH_2$—, $C_2F_5CH_2$—, $HCF_2CF_2CH_2$—, or $CF_3CFHCF_2CH_2$—. In order to achieve high incombustibility and good rate characteristics and oxidation resistance, the fluorinated alkyl group for $Rf^2$ and $R^6$ is more preferably $CF_3CH_2$—, $CF_3CF_2CH_2$—, or $HCF_2CF_2CH_2$—.

If $R^6$ is an alkyl group free from a fluorine atom, it is a C1-C7 alkyl group. In order to achieve a low viscosity, $R^6$ preferably has a carbon number of 1 to 4, more preferably 1 to 3.

Examples of the alkyl group free from a fluorine atom include $CH_3-$, $CH_3CH_2-$, $(CH_3)_2CH-$, and $C_3H_7-$. In order to achieve a low viscosity and good rate characteristics, $CH_3-$ or $CH_3CH_2-$ is preferred.

The fluorinated acyclic carbonate preferably has a fluorine content of 20 to 70 mass %. The fluorinated acyclic carbonate having a fluorine content within the above range makes it possible to maintain the compatibility with a solvent and the solubility of the salt. The fluorine content is more preferably 30 mass % or more, still more preferably 35 mass % or more, while more preferably 60 mass % or less, still more preferably 50 mass % or less.

The fluorine content in the present invention is a value calculated by the following formula: {(Number of fluorine atoms×19)/molecular weight of the fluorinated acyclic carbonate}×100(%), based on the structural formula of the fluorinated acyclic carbonate.

The fluorinated acyclic carbonate is preferably any of the following compounds because they have a low viscosity.

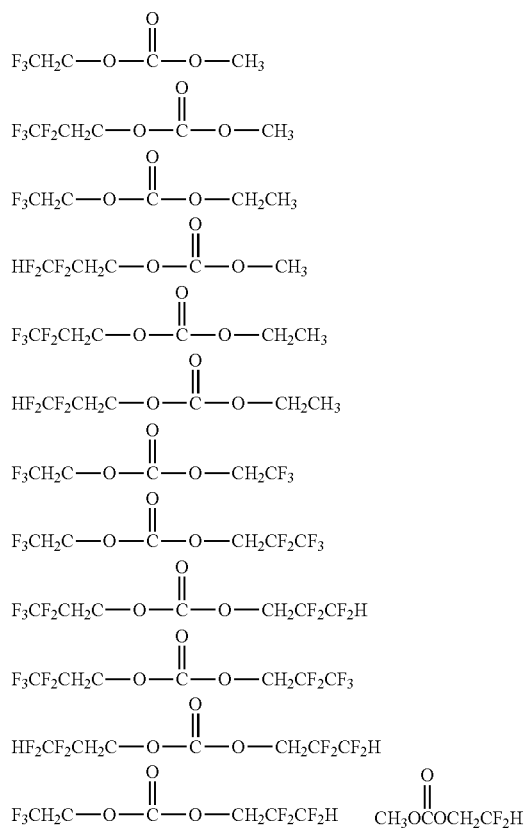

The amount of the fluorinated acyclic carbonate is preferably 1 to 90 vol % in the solvent. The fluorinated acyclic carbonate in an amount within the above range makes it possible to maintain the compatibility.

In order to maintain the solubility of the salt, the amount of the fluorinated acyclic carbonate in the electrolytic solution is more preferably 30 vol % or more, still more preferably 40 vol % or more, while more preferably 85 vol % or less, still more preferably 80 vol % or less.

Examples of the non-fluorinated acyclic carbonate include hydrocarbon-type acyclic carbonates such as $CH_3OCOOCH_3$ (dimethyl carbonate, DMC), $CH_3CH_2OCOOCH_2CH_3$ (diethyl carbonate, DEC), $CH_3CH_2OCOOCH_3$ (ethyl methyl carbonate, EMC), $CH_3OCOOCH_2CH_2CH_3$ (methyl propyl carbonate), methyl butyl carbonate, ethyl propyl carbonate, and ethyl butyl carbonate. In particular, the non-fluorinated acyclic carbonate is preferably at least one selected from the group consisting of ethyl methyl carbonate, diethyl carbonate, and dimethyl carbonate.

The amount of the non-fluorinated acyclic carbonate in the solvent is preferably 0 to 99 vol %, more preferably 1 vol % or more, while more preferably 90 vol % or less.

When the solvent contains the fluorinated saturated cyclic carbonate and the fluorinated acyclic carbonate, the lower limit of the amount of the fluorinated saturated cyclic carbonate is preferably 0.1 mass %, more preferably 0.2 mass %. The upper limit of the amount of the fluorinated saturated cyclic carbonate is preferably 60 mass %, more preferably 40 mass %. The lower limit of the amount of the fluorinated acyclic carbonate is preferably 30 mass %, more preferably 40 mass %. The upper limit of the amount of the fluorinated acyclic carbonate is preferably 90 mass %, more preferably 80 mass %.

The solvent preferably contains an acyclic ether. The acyclic ether may be a non-fluorinated acyclic ether or may be a fluorinated acyclic ether. The solvent more preferably contains a fluorinated acyclic ether.

The non-fluorinated acyclic ether preferably has a carbon number of 3 to 10.

Examples of the non-fluorinated acyclic ether include diethyl ether, di-n-butyl ether, dimethoxy methane, methoxy ethoxy methane, diethoxy methane, dimethoxy ethane, methoxy ethoxy ethane, diethoxy ethane, ethylene glycol di-n-propyl ether, ethylene glycol di-n-butyl ether, and diethylene glycol dimethyl ether.

One example of the fluorinated acyclic ether is a fluorinated acyclic ether (K) represented by formula (K) below:

$$Rf^1-O-Rf^2 \quad (K)$$

(wherein $Rf^1$ and $Rf^2$ may be the same as or different from each other, and each are a C1-C10 alkyl group or a C1-C10 fluorinated alkyl group; but at least one of $Rf^1$ and $Rf^2$ is a C1-C10 fluorinated alkyl group). Containing the fluorinated acyclic ether (K) can improve the incombustibility of the electrolytic solution, as well as improve the stability and safety at high temperature under high voltage.

In formula (K), at least one of $Rf^1$ and $Rf^2$ has only to be a C1-C10 fluorinated alkyl group. In order to further improve the incombustibility and the stability and safety at high temperature under high voltage of the electrolytic solution, both $Rf^1$ and $Rf^2$ are preferably a C1-C10 fluorinated alkyl group. In this case, $Rf^1$ and $Rf^2$ may be the same as or different from each other.

Particular preferably, $Rf^1$ and $Rf^2$ are the same as or different from each other, and $Rf^1$ is a C3-C6 fluorinated alkyl group and $Rf^2$ is a C2-C6 fluorinated alkyl group.

If the sum of the carbon numbers of $Rf^1$ and $Rf^2$ is too small, the fluorinated acyclic ether may have too low a boiling point. If the carbon number of $Rf^1$ or $Rf^2$ is too large, the solubility of the electrolyte salt may be low, which may cause a bad influence on the compatibility with other solvent, and the viscosity may be high so that the rate characteristics may be poor. In order to achieve excellent rate characteristics and boiling point, advantageously, the carbon number of $Rf^1$ is 3 or 4 and the carbon number of $Rf^2$ is 2 or 3.

The fluorinated acyclic ether (K) preferably has a fluorine content of 40 to 75 mass %. The fluorinated acyclic ether (K) having a fluorine content within this range may lead to particularly excellent balance between the incombustibility and the compatibility. The above range is also preferred for good oxidation resistance and safety.

The lower limit of the fluorine content is more preferably 45 mass %, still more preferably 50 mass %, particularly preferably 55 mass %. The upper limit thereof is more preferably 70 mass %, still more preferably 66 mass %.

The fluorine content of the fluorinated acyclic ether (K) is a value calculated by the following formula: {(number of fluorine atoms×19)/(molecular weight of fluorinated acyclic ether (K))}×100(%) based on the structural formula of the fluorinated acyclic ether (K).

Examples of the group for $Rf^1$ include $CF_3CF_2CH_2-$, $CF_3CFHCF_2-$, $HCF_2CF_2CF_2-$, $HCF_2CF_2CH_2-$, $CF_3CF_2CH_2CH_2-$, $CF_3CFHCF_2CH_2-$, $HCF_2CF_2CF_2CF_2-$, $HCF_2CF_2CF_2CH_2-$, $HCF_2CF_2CH_2CH_2-$, and $HCF_2CF(CF_3)CH_2-$.

Examples of the group for $Rf^2$ include $CF_3CF_2CH_2-$, $CF_3CFHCF_2-$, $CF_2HCF_2CF_2-$, $CF_2HCF_2CH_2-$, $CF_3CF_2CH_2CH_2-$, $CF_3CFHCF_2CH_2-$, $CF_2HCF_2CF_2CF_2-$, $CF_2HCF_2CF_2CH_2-$, $CF_2HCF_2CH_2CH_2-$, $CF_2HCF(CF_3)CH_2-$, $CF_2HCF_2-$, $CF_2HCH_2-$, and $CH_3CF_2-$.

Specific examples of the fluorinated acyclic ether (K) include $HCF_2CF_2CH_2OCF_2CF_2H$, $CF_3CF_2CH_2OCF_2CF_2H$, $HCF_2CF_2CH_2OCF_2CFHCF_3$, $CF_3CF_2CH_2OCF_2CFHCF_3$, $C_6F_{13}OCH_3$, $C_6F_{13}OC_2H_5$, $C_8F_{17}OCH_3$, $C_8F_{17}OC_2H_5$, $CF_3CFHCF_2CH(CH_3)OCF_2CFHCF_3$, $HCF_2CF_2OCH(C_2H_5)_2$, $HCF_2CF_2OC_4H_9$, $HCF_2CF_2OCH_2CH(C_2H_5)_2$, and $HCF_2CF_2OCH_2CH(CH_3)_2$.

In particular, those having $HCF_2-$ or $CF_3CFH-$ at one end or both ends can provide a fluorinated acyclic ether (K) excellent in polarizability and having a high boiling point. The boiling point of the fluorinated acyclic ether (K) is preferably 67° C. to 120° C. It is more preferably 80° C. or higher, still more preferably 90° C. or higher.

Such a fluorinated acyclic ether (K) may include one or two or more of $CF_3CH_2OCF_2CFHCF_3$, $CF_3CF_2CH_2OCF_2CFHCF_3$, $HCF_2CF_2CH_2OCF_2CFHCF_3$, $HCF_2CF_2CH_2OCH_2CF_2CF_2H$, $CF_3CFHCF_2CH_2OCF_2CFHCF_3$, $HCF_2CF_2CH_2OCH_2CF_2H$, $CF_3CF_2CH_2OCF_2CF_2H$, and the like.

In order to advantageously achieve a high boiling point, good compatibility with other solvents, and a good solubility of the electrolyte salt, the fluorinated acyclic ether (K) is preferably at least one selected from the group consisting of $HCF_2CF_2CH_2OCF_2CFHCF_3$ (boiling point: 106° C.), $CF_3CF_2CH_2OCF_2CFHCF_3$ (boiling point: 82° C.), $HCF_2CF_2CH_2CF_2CF_2H$ (boiling point: 92° C.), and $CF_3CF_2CH_2OCF_2CF_2H$ (boiling point: 68° C.), more preferably at least one selected from the group consisting of $HCF_2CF_2CH_2OCF_2CFHCF_3$ (boiling point: 106° C.), $HCF_2CF_2CH_2OCF_2CF_2H$ (boiling point: 92° C.), and $CF_3CF_2CH_2OCF_2CF_2H$ (boiling pint 68° C.).

The amount of the acyclic ether relative to the solvent is preferably 0 to 99.9 vol %, more preferably 0.1 vol % or more, while more preferably 90 vol % or less.

The amount of the fluorinated acyclic ether relative to the solvent is preferably 0 to 99.9 vol %, more preferably 0.1 vol % or more, while more preferably 90 vol % or less.

The solvent may contain at least one selected from the group consisting of the fluorinated saturated cyclic carbonate and the fluorinated acyclic carbonate, and the fluorinated acyclic ether.

When the solvent contains at least one selected from the group consisting of the fluorinated saturated cyclic carbonate and the fluorinated acyclic carbonate, and the fluorinated acyclic ether, the lower limit of the amount of the fluorinated carbonate is preferably 40 mass %, more preferably 50 mass %. The upper limit of the amount of the fluorinated carbonate is preferably 90 mass %, more preferably 80 mass %. The lower limit of the amount of the fluorinated acyclic ether is preferably 0.1 mass %, more preferably 0.2 mass %. The upper limit of the amount of the fluorinated acyclic ether is preferably 70 mass %, more preferably 60 mass %.

The solvent may contain the fluorinated saturated cyclic carbonate, the fluorinated acyclic carbonate, and the fluorinated acyclic ether.

When the solvent contains the fluorinated saturated cyclic carbonate, the fluorinated acyclic carbonate, and the fluorinated acyclic ether, the lower limit of the amount of the fluorinated saturated cyclic carbonate is preferably 0.1 mass %, more preferably 0.2 mass %. The upper limit of the amount of the fluorinated saturated cyclic carbonate is preferably 60 mass %, more preferably 40 mass %. The lower limit of the amount of the fluorinated acyclic carbonate is preferably 30 mass %, more preferably 40 mass %. The upper limit of the amount of the fluorinated acyclic carbonate is preferably 90 mass %, more preferably 80 mass %. The lower limit of the amount of the fluorinated acyclic ether is preferably 0.1 mass %, more preferably 0.2 mass %. The upper limit of the amount of the fluorinated acyclic ether is preferably 60 mass %, more preferably 40 mass %.

The electrolytic solution of the present invention preferably contains an electrolyte salt (excluding the lithium salt (X) and the compound (7)).

The electrolyte salt may be any salt that can be used in the electrolytic solution, such as lithium salts, ammonium salts, and metal salts, as well as liquid salts (ionic liquid), inorganic polymeric salts, and organic polymeric salts.

The electrolyte salt of the electrolytic solution for a lithium ion secondary battery is preferably a lithium salt (excluding the lithium salt (X) and the compound (7)).

Examples of the lithium salt include inorganic lithium salts such as $LiClO_4$, $LiPF_6$, and $LiBF_4$; and fluoroorganic acid lithium salts such as $LiCF_3SO_3$, $LiN(CF_3SO_2)_2$, $LiN(C_2F_5SO_2)_2$, $LiN(CF_3SO_2)(C_4F_9SO_2)$, $LiC(CF_3SO_2)_3$, $LiPF_4(CF_3)_2$, $LiPF_4(C_2F_5)_2$, $LiPF_4(CF_3SO_2)_2$, $LiPF_4(C_2F_5SO_2)_2$, $LiBF_2(CF_3)_2$, $LiBF_2(C_2F_5)_2$, $LiBF_2(CF_3SO_2)_2$, $LiBF_2(C_2F_5SO_2)_2$, and salts represented by the formula: $LiPF_a(C_nF_{2n+1})_{6-a}$ (wherein a is an integer of 0 to 5; and n is an integer of 1 to 6). These may be used alone or in combination of two or more.

In order to suppress degradation of the electrolytic solution after high-temperature storage, the lithium salt is particularly preferably at least one selected from the group consisting of $LiPF_6$, $LiBF_4$, $LiCF_3SO_3$, $LiN(CF_3SO_2)_2$, $LiN(C_2F_5SO_2)_2$, and salts represented by the formula: $LiPF_a(C_nF_{2n+1})_{6-a}$ (wherein a is an integer of 0 to 5; and n is an integer of 1 to 6).

Examples of the salts represented by the formula: $LiPF_a(C_nF_{2n+1})_{6-a}$ include $LiPF_3(CF_3)_3$, $LiPF_3(C_2F_5)_3$, $LiPF_3(C_3F_7)_3$, $LiPF_3(C_4F_9)_3$, $LiPF_4(CF_3)_2$, $LiPF_4(C_2F_5)_2$, $LiPF_4(C_3F_7)_2$, and $LiPF_4(C_4F_9)_2$ wherein the alkyl group represented by $C_3F_7$ or $C_4F_9$ in the formula may be either linear or branched.

The concentration of the lithium salt in the electrolytic solution is preferably 0.5 to 3 mol/L. If the concentration thereof is outside this range, the electrolytic solution tends to have a low electric conductivity and the battery performance tends to be impaired.

The concentration of the electrolyte salt is more preferably 0.9 mol/L or more and 1.5 mol/L or less.

The electrolyte salt in the electrolytic solution for an electric double layer capacitor is preferably an ammonium salt.

Examples of the ammonium salt include the following salts (IIa) to (IIe).

(IIa) Tetraalkyl Quaternary Ammonium Salts

Preferred examples thereof include tetraalkyl quaternary ammonium salts represented by formula (IIa):

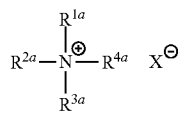

(IIa)

(wherein $R^{1a}$, $R^{2a}$, $R^{3a}$, and $R^{4a}$ may be the same as or different from each other, and are individually a C1-C6 alkyl group which may optionally have an ether bond; and $X^-$ is an anion). In order to improve the oxidation resistance, part or all of the hydrogen atoms in the ammonium salt is/are also preferably replaced by a fluorine atom and/or a C1-C4 fluorinated alkyl group.

Specific examples of the tetraalkyl quaternary ammonium salts include tetraalkyl quaternary ammonium salts represented by formula (IIa-1):

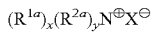

(IIa-1)

(wherein $R^{1a}$, $R^{2a}$, and $X^-$ are defined in the same manner as mentioned above; x and y may be the same as or different from each other, and are individually an integer of 0 to 4, where x+y=4), and alkyl ether group-containing trialkyl ammonium salts represented by formula (IIa-2):

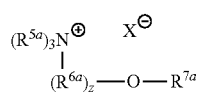

(IIa-2)

(wherein $R^{5a}$ is a C1-C6 alkyl group; $R^{6a}$ is a C1-C6 divalent hydrocarbon group; $R^{7a}$ is a C1-C4 alkyl group; z is 1 or 2; and $X^-$ is an anion). Introduction of an alkyl ether group may lead to reduction in the viscosity.

The anion $X^-$ may be either an inorganic anion or an organic anion. Examples of the inorganic anion include $AlCl_4^-$, $BF_4^-$, $PF_6^-$, $AsF_6^-$, $TaF_6^-$, $I^-$, and $SbF_6^-$. Examples of the organic anion include $CF_3COO^-$, $CF_3SO_3^-$, $(CF_3SO_2)_2N^-$, and $(C_2F_5SO_2)_2N^-$.

In order to achieve good oxidation resistance and ionic dissociation, $BF_4^-$, $PF_6^-$, $AsF_6^-$, and $SbF_6^-$ are preferred.

Preferred specific examples of the tetraalkyl quaternary ammonium salts include $Et_4NBF_4$, $Et_4NClO_4$, $Et_4NPF_6$, $Et_4NAsF_6$, $Et_4NSbF_6$, $Et_4NCF_3SO_3$, $Et_4N(CF_3SO_2)_2N$, $Et_4NC_4F_9SO_3$, $Et_3MeNBF_4$, $Et_3MeNClO_4$, $Et_3MeNPF_6$, $Et_3MeNAsF_6$, $Et_3MeNSbF_6$, $Et_3MeNCF_3SO_3$, $Et_3MeN(CF_3SO_2)_2N$, and $Et_3MeNC_4F_9SO_3$. In particular, $Et_4NBF_4$, $Et_4NPF_6$, $Et_4NSbF_6$, $Et_4NAsF_6$, $Et_3MeNBF_4$, and an N,N-diethyl-N-methyl-N-(2-methoxyethyl)ammonium salt may be mentioned.

(IIb) Spirocyclic Bipyrrolidinium Salts

Preferred examples thereof include spirocyclic bipyrrolidinium salts represented by formula (IIb-1):

(IIb-1)

(wherein $R^{8a}$ and $R^{9a}$ may be the same as or different from each other, and are individually a C1-C4 alkyl group; $X^-$ is an anion; n1 is an integer of 0 to 5; and n2 is an integer of 0 to 5); spirocyclic bipyrrolidinium salts represented by formula (IIb-2):

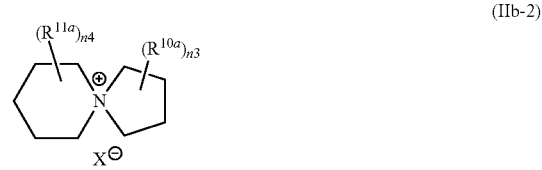

(IIb-2)

(wherein $R^{10a}$ and $R^{11a}$ may be the same as or different from each other, and are individually a C1-C4 alkyl group; $X^-$ is an anion; n3 is an integer of 0 to 5; and n4 is an integer of 0 to 5); and spirocyclic bipyrrolidinium salts represented by formula (IIb-3):

(IIb-3)

(wherein $R^{12a}$ and $R^{13a}$ may be the same as or different from each other, and are individually a C1-C4 alkyl group; $X^-$ is an anion; n5 is an integer of 0 to 5; and n6 is an integer of 0 to 5). In order to improve the oxidation resistance, part or all of the hydrogen atoms in the spirocyclic bipyrrolidinium salt is/are also preferably replaced by a fluorine atom and/or a C1-C4 fluorinated alkyl group.

Preferred specific examples of the anion $X^-$ are the same as those mentioned for the salts (IIa). In order to achieve good dissociation and a low internal resistance under high voltage, $BF_4^-$, $PF_6^-$, $(CF_3SO_2)_2N^-$, or $(C_2F_5SO_2)_2N^-$ is particularly preferred.

For example, those represented by the following formulas:

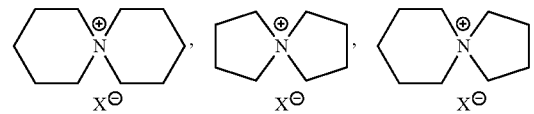

may be mentioned as preferred specific examples of the spirocyclic bipyrrolidinium salts.

These spirocyclic bipyrrolidinium salts are excellent in the solubility in a solvent, the oxidation resistance, and the ion conductivity.

(IIc) Imidazolium Salts

Preferred examples thereof include imidazolium salts represented by formula (IIc):

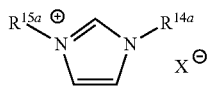

(IIc)

(wherein $R^{14a}$ and $R^{15a}$ may be the same as or different from each other, and are individually a C1-C6 alkyl group; and $X^-$ is an anion). In order to improve the oxidation resistance, part or all of the hydrogen atoms in the imidazolium salt is/are also preferably replaced by a fluorine atom and/or a C1-C4 fluorinated alkyl group.

Preferred specific examples of the anion $X^-$ are the same as those mentioned for the salts (IIa).

For example, one represented by the following formula:

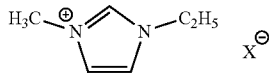

may be mentioned as a preferred specific example of the imidazolium salt.

This imidazolium salt is excellent in that it has a low viscosity and a good solubility.

(IId): N-Alkylpyridinium Salts

Preferred examples thereof include N-alkylpyridinium salts represented by formula (IId):

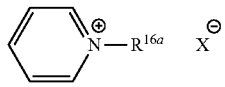

(IId)

(wherein $R^{16a}$ is a C1-C6 alkyl group; and $X^-$ is an anion) In order to improve the oxidation resistance, part or all of the hydrogen atoms in the N-alkylpyridinium salt is/are also preferably replaced by a fluorine atom and/or a C1-C4 fluorinated alkyl group.

Preferred specific examples of the anion $X^-$ are the same as those mentioned for the salts (IIa).

For example, those represented by the following formulas:

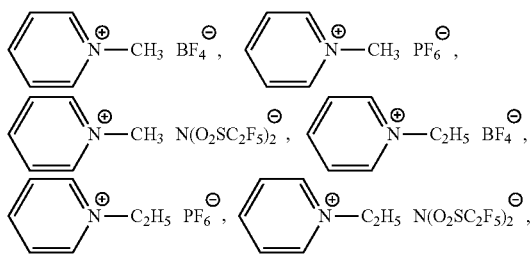

may be mentioned as preferred specific examples of the N-alkylpyridinium salts.

These N-alkylpyridinium salts are excellent in that they have a low viscosity and a good solubility.

(IIe) N,N-Dialkylpyrrolidinium Salts

Preferred examples thereof include N,N-dialkylpyrrolidinium salts represented by formula (IIe):

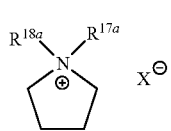

(IIe)

(wherein $R^{17a}$ and $R^{18a}$ may be the same as or different from each other, and are individually a C1-C6 alkyl group; and $X^-$ is an anion). In order to improve the oxidation resistance, part or all of the hydrogen atoms in the N,N-dialkylpyrrolidinium salt is/are also preferably replaced by a fluorine atom and/or a C1-C4 fluorinated alkyl group.

Preferred specific examples of the anion $X^-$ are the same as those mentioned for the salts (IIa).

For example, those represented by the following formulas:

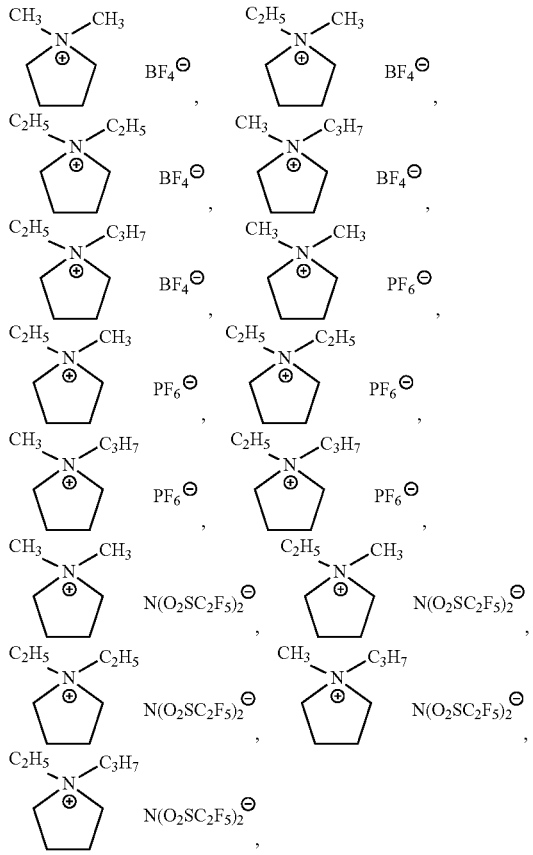

may be mentioned as preferred specific examples of the N,N-dialkylpyrrolidinium salts.

These N,N-dialkylpyrrolidinium salts are excellent in that they have a low viscosity and a good solubility.

Preferred among these ammonium salts are those represented by formula (IIa), (IIb), or (IIc) because they have a good solubility, oxidation resistance, and ion conductivity. More preferred are those represented by the following formulas:

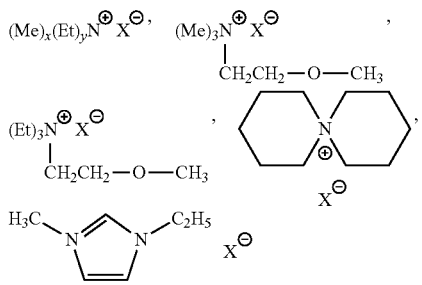

wherein Me is a methyl group; Et is an ethyl group; and X⁻, x, and y are defined in the same manner as in formula (IIa-1).

A lithium salt may be used as an electrolyte salt for electric double layer capacitors. Preferred examples thereof include $LiPF_6$, $LiBF_4$, $LiAsF_6$, $LiSbF_6$, and $LiN(SO_2C_2H_5)_2$.

In order to further increase the capacity, a magnesium salt may be used. Preferred examples of the magnesium salt include $Mg(ClO_4)_2$ and $Mg(OOC_2H_5)_2$.

If the electrolyte salt is any of the above ammonium salts, the concentration thereof is preferably 1.1 mol/L or higher. If the concentration thereof is lower than 1.1 mol/L, not only the low-temperature characteristics may be poor but also the initial internal resistance may be high. The concentration of the electrolyte salt is more preferably 1.25 mol/L or higher.

For good low-temperature characteristics, the concentration is preferably 1.7 mol/L or lower, more preferably 1.5 mol/L or lower.

If the ammonium salt is triethyl methyl ammonium tetrafluoroborate ($TEMABF_4$), the concentration thereof is preferably 1.1 to 1.4 mol/L in order to achieve excellent low-temperature characteristics.

If the ammonium salt is spirobipyrrolidinium tetrafluoroborate ($SBPBF_4$), the concentration thereof is preferably 1.3 to 1.7 mol/L.

The electrolytic solution of the present invention preferably further includes polyethylene oxide that has a weight average molecular weight of 2000 to 4000 and has —OH, —OCOOH, or —COOH at an end.

Containing such a compound improves the stability at the interfaces between the electrolytic solution and the respective electrodes, and thus can improve the battery characteristics.

Examples of the polyethylene oxide include polyethylene oxide monool, polyethylene oxide carboxylate, polyethylene oxide diol, polyethylene oxide dicarboxylate, polyethylene oxide triol, and polyethylene oxide tricarboxylate. These may be used alone or in combination of two or more.

In order to achieve good battery characteristics, a mixture of polyethylene oxide monool and polyethylene oxide diol and a mixture of polyethylene carboxylate and polyethylene dicarboxylate are preferred.

The polyethylene oxide having too small a weight average molecular weight may be easily oxidatively decomposed. The weight average molecular weight is more preferably 3000 to 4000.

The weight average molecular weight can be determined in terms of polystyrene equivalent by gel permeation chromatography (GPC).

The amount of the polyethylene oxide is preferably $1\times10^{-6}$ to $1\times10^{-2}$ mol/kg in the electrolytic solution. If the amount of the polyethylene oxide is too large, the battery characteristics may be poor.

The amount of the polyethylene oxide is more preferably $5\times10^{-6}$ mol/kg or more.

The electrolytic solution of the present invention may further contain, as an additive, an unsaturated cyclic carbonate. Containing such a compound suppresses degradation of the battery characteristics.

The unsaturated cyclic carbonate is a cyclic carbonate having an unsaturated bond, i.e., a cyclic carbonate having at least one carbon-carbon unsaturated bond in the molecule. Specific examples thereof include vinylene carbonate compounds such as vinylene carbonate, methyl vinylene carbonate, ethyl vinylene carbonate, 4,5-dimethyl vinylene carbonate, and 4,5-diethyl vinylene carbonate; and vinyl ethylene carbonate compounds such as 4-vinyl ethylene carbonate (VEC), 4-methyl-4-vinyl ethylene carbonate, 4-ethyl-4-vinyl ethylene carbonate, 4-n-propyl-4-vinyl ethylene carbonate, 5-methyl-4-vinyl ethylene carbonate, 4,4-divinyl ethylene carbonate, 4,5-divinyl ethylene carbonate, 4,4-dimethyl-5-methylene ethylene carbonate, and 4,4-diethyl-5-methylene ethylene carbonate. Preferred among these is vinylene carbonate, 4-vinyl ethylene carbonate, 4-methyl-4-vinyl ethylene carbonate, or 4,5-divinyl ethylene carbonate, and particularly preferred is vinylene carbonate or 4-vinyl ethylene carbonate.

The unsaturated cyclic carbonate may have any molecular weight that does not significantly deteriorate the effects of the present invention. The molecular weight is preferably 50 or higher and 250 or lower. The unsaturated cyclic carbonate having a molecular weight within this range is likely to assure its solubility in the electrolytic solution and to enable sufficient achievement of the effects of the present invention. The molecular weight of the unsaturated cyclic carbonate is more preferably 80 or higher, while more preferably 150 or lower.

The unsaturated cyclic carbonate may also be preferably a fluorinated unsaturated cyclic carbonate.

The number of fluorine atoms in the fluorinated unsaturated cyclic carbonate may be any number that is 1 or greater. The number of fluorine atoms is usually 6 or smaller, preferably 4 or smaller, most preferably 1 or 2.

Examples of the fluorinated unsaturated cyclic carbonate include fluorinated vinylene carbonate derivatives and fluorinated ethylene carbonate derivatives substituted with a substituent having an aromatic ring or a carbon-carbon double bond.

Examples of the fluorinated vinylene carbonate derivatives include 4-fluorovinylene carbonate, 4-fluoro-5-methyl vinylene carbonate, 4-fluoro-5-phenyl vinylene carbonate, 4-allyl-5-fluorovinylene carbonate, and 4-fluoro-5-vinyl vinylene carbonate.

Examples of the fluorinated ethylene carbonate derivatives substituted with a substituent having an aromatic ring or a carbon-carbon double bond include 4-fluoro-4-vinyl ethylene carbonate, 4-fluoro-4-allyl ethylene carbonate, 4-fluoro-5-vinyl ethylene carbonate, 4-fluoro-5-allyl ethylene carbonate, 4,4-difluoro-4-vinyl ethylene carbonate, 4,4-difluoro-4-allyl ethylene carbonate, 4,5-difluoro-4-vinyl ethylene carbonate, 4,5-difluoro-4-allyl ethylene carbonate, 4-fluoro-4,5-divinyl ethylene carbonate, 4-fluoro-4,5-diallyl ethylene carbonate, 4,5-difluoro-4,5-divinyl ethylene carbonate, 4,5-difluoro-4,5-diallyl ethylene carbonate, 4-fluoro-4-phenyl ethylene carbonate, 4-fluoro-5-phenyl ethylene carbonate, 4,4-difluoro-5-phenyl ethylene carbonate, and 4,5-difluoro-4-phenyl ethylene carbonate.

The fluorinated unsaturated cyclic carbonate may have any molecular weight that does not significantly deteriorate the effects of the present invention. The molecular weight is preferably 50 or higher and 500 or lower. The fluorinated unsaturated cyclic carbonate having a molecular weight within this range is likely to assure the solubility of the fluorinated cyclic carbonate in the electrolytic solution and to enable sufficient achievement of the effects of the present invention.

The unsaturated cyclic carbonates may be used alone or in any combination of two or more at any ratio.

If the unsaturated cyclic carbonate is used as an additive, the amount thereof in the electrolytic solution is preferably 0.1 to 10 mass %, more preferably 1 mass % or more, while more preferably 5 mass % or less.

The electrolytic solution of the present invention may further contain any other solvents or additives such as cyclic or acyclic carboxylates, cyclic ethers, nitrogen-containing compounds, boron-containing compounds, organic silicon-containing compounds, fireproof agents (flame retardants), surfactants, additives for increasing the permittivity, improvers for cycle characteristics and rate characteristics, and overcharge inhibitors, to the extent that the effects of the present invention are not impaired.

Examples of the cyclic carboxylates include those having 3 to 12 carbon atoms in total in the structural formula. Specific examples thereof include gamma-butyrolactone, gamma-valerolactone, gamma-caprolactone, and epsilon-caprolactone. Particularly preferred is gamma-butyrolactone because it can improve the battery characteristics owing to improvement in the degree of dissociation of lithium ions.

In general, the amount of the cyclic carboxylate is preferably 0.1 mass % or more, more preferably 1 mass % or more, in 100 mass % of the solvent. The cyclic carboxylate in an amount within this range is likely to improve the electric conductivity of the electrolytic solution, and thus to improve the large-current discharge characteristics of electrolyte batteries. The amount of the cyclic carboxylate is also preferably 10 mass % or less, more preferably 5 mass % or less. Such an upper limit may allow the electrolytic solution to have a viscosity within an appropriate range, may make it possible to avoid a reduction in the electric conductivity, may suppress an increase in the resistance of the negative electrode, and may allow electrolyte batteries to have large-current discharge characteristics within a favorable range.

The cyclic carboxylate to be suitably used may be a fluorinated cyclic carboxylate (fluorolactone). Examples of the fluorolactone include fluorolactones represented by formula (E) below:

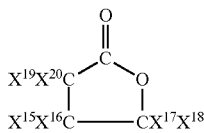
(E)

wherein $X^{15}$ to $X^{20}$ may be the same as or different from each other, and are individually —H, —F, —Cl, —CH$_3$, or a fluorinated alkyl group; and at least one of $X^{15}$ to $X^{20}$ is a fluorinated alkyl group.

Examples of the fluorinated alkyl group for $X^{15}$ to $X^{20}$ include —CFH$_2$, —CF$_2$H, —CF$_3$, —CH$_2$CF$_3$, —CF$_2$CF$_3$, —CH$_2$CF$_2$CF$_3$, and —CF(CF$_3$)$_2$. In order to achieve high oxidation resistance and an effect of improving the safety, —CH$_2$CF$_3$ and —CH$_2$CF$_2$CF$_3$ are preferred.

One of $X^{15}$ to $X^{20}$ or a plurality thereof may be replaced by —H, —F, —Cl, —CH$_3$, or a fluorinated alkyl group only when at least one of $X^{15}$ to $X^{20}$ is a fluorinated alkyl group. In order to achieve a good solubility of the electrolyte salt, the number of substituents is preferably 1 to 3, more preferably 1 or 2.

The substitution may be at any of the above sites in the fluorinated alkyl group. In order to achieve a good synthesizing yield, the substitution site is preferably $X^{17}$ and/or $X^{18}$. In particular, $X^{17}$ or $X^{18}$ is preferably a fluorinated alkyl group, especially, —CH$_2$CF$_3$ or —CH$_2$CF$_2$CF$_3$. The substituent for $X^{15}$ to $X^{20}$ other than the fluorinated alkyl group is —H, —F, —Cl, or CH$_3$. In order to achieve a good solubility of the electrolyte salt, —H is preferred.

In addition to those represented by the above formula, the fluorolactone may also be a fluorolactone represented by formula (F) below:

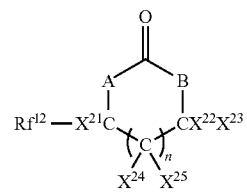
(F)

wherein one of A and B is $CX^{26}X^{27}$ (where $X^{26}$ and $X^{27}$ may be the same as or different from each other, and are individually —H, —F, —Cl, —CF$_3$, —CH$_3$, or an alkylene group in which a hydrogen atom may optionally be replaced by a halogen atom and which may optionally has a hetero atom in the chain) and the other is an oxygen atom; $Rf^{12}$ is a fluorinated alkyl group or fluorinated alkoxy group which may optionally have an ether bond; $X^{21}$ and $X^{22}$ may be the same as or different from each other, and are individually —H, —F, —Cl, —CF$_3$, or CH$_3$; $X^{23}$ to $X^{25}$ may be the same as or different from each other, and are individually —H, —F, —Cl, or an alkyl group in which a hydrogen atom may optionally be replaced by a halogen atom and which may optionally contain a hetero atom in the chain; and n=0 or 1.

Preferred examples of the fluorolactone represented by formula (F) include a 5-membered ring structure represented by formula (G) below:

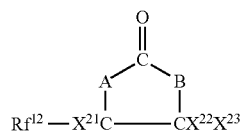
(G)

(wherein A, B, $Rf^{12}$, $X^{21}$, $X^{22}$, and $X^{23}$ are defined in the same manner as in formula (F)) because it is easily synthesized and has good chemical stability. Further, in relation to the combination of A and B, fluorolactones represented by formula (H) below:

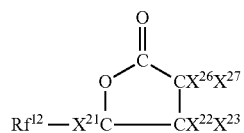
(H)

(wherein $Rf^{12}$, $X^{21}$, $X^{22}$, $X^{23}$, $X^{26}$, and $X^{27}$ are defined in the same manner as in formula (F)) and fluorolactones represented by formula (I) below:

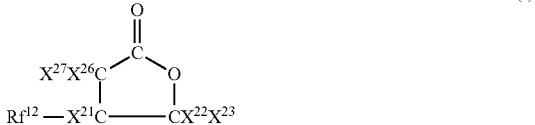
(I)

(wherein $Rf^{12}$, $X^{21}$, $X^{22}$, $X^{23}$, $X^{26}$, and $X^{27}$ are defined in the same manner as in formula (F)) may be mentioned.

In order to particularly achieve excellent characteristics such as a high permittivity and a high withstand voltage, and to improve the characteristics of the electrolytic solution in the present invention, for example, to achieve a good solubility of the electrolyte salt and to well reduce the internal resistance, those represented by the following formulas:

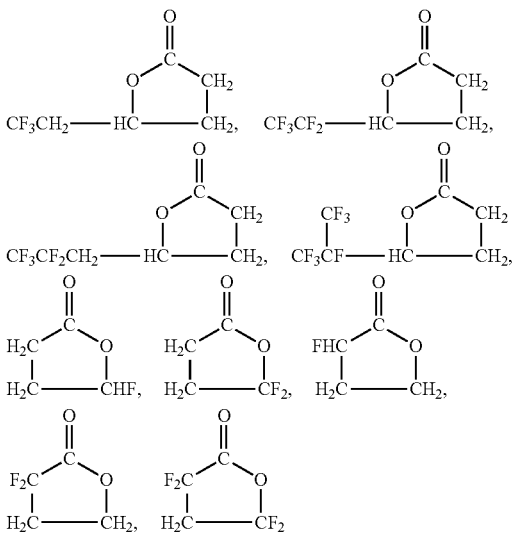

may be mentioned.

Containing a fluorinated cyclic carboxylate leads to effects of, for example, improving the ion conductivity, improving the safety, and improving the stability at high temperature.

Examples of the acyclic carboxylate include those having three to seven carbon atoms in total in the structural formula. Specific examples thereof include methyl acetate, ethyl acetate, n-propyl acetate, isopropyl acetate, n-butyl acetate, isobutyl acetate, t-butyl acetate, methyl propionate, ethyl propionate, n-propyl propionate, isopropyl propionate, n-butyl propionate, isobutyl propionate, t-butyl propionate, methyl butyrate, ethyl butyrate, n-propyl butyrate, isopropyl butyrate, methyl isobutyrate, ethyl isobutyrate, n-propyl isobutyrate, and isopropyl isobutyrate.

In order to improve the ion conductivity owing to a reduction in the viscosity, preferred are methyl acetate, ethyl acetate, n-propyl acetate, n-butyl acetate, methyl propionate, ethyl propionate, n-propyl propionate, isopropyl propionate, methyl butyrate, and ethyl butyrate, for example.

Also, a fluorinated acyclic carboxylate may also suitably be used. Preferred examples of the fluorine-containing ester include fluorinated acyclic carboxylates represented by formula (J) below:

$Rf^{10}COORf^{11}$ (J)

(wherein $Rf^{10}$ is a C1-C2 fluorinated alkyl group; and $Rf^{11}$ is a C1-C4 fluorinated alkyl group) because they are high in flame retardance and have good compatibility with other solvents and good oxidation resistance.

Examples of the group for $Rf^{10}$ include $CF_3-$, $CF_3CF_2-$, $HCF_2CF_2-$, $HCF_2-$, $CH_3CF_2-$, and $CF_3CH_2-$. In order to achieve good rate characteristics, $CF_3-$ and $CF_3CF_2-$ are particularly preferred.

Examples of the group for $Rf^{11}$ include $CF_3-$, $CF_3CF_2-$, $(CF_3)_2CH-$, $CF_3CH_2-$, $CF_3CH_2CH_2-$, $CF_3CFHCF_2CH_2-$, $C_2F_5CH_2-$, $CF_2HCF_2CH_2-$, $C_2F_5CH_2CH_2-$, $CF_3CF_2CH_2-$, and $CF_3CF_2CF_2CH_2-$. In order to achieve good compatibility with other solvents, $CF_3CH_2-$, $(CF_3)_2CH-$, $C_2F_5CH_2-$, and $CF_2HCF_2CH_2-$ are particularly preferred.

Specifically, for example, the fluorinated acyclic carboxylate may include one or two or more of $CF_3C(=O)OCH_2CF_3$, $CF_3C(=O)OCH_2CH_2CF_3$, $CF_3C(=O)OCH_2C_2F_5$, $CF_3C(=O)OCH_2CF_2CF_2H$, and $CF_3C(=O)OCH(CF_3)_2$. In order to achieve good compatibility with other solvents and good rate characteristics, $CF_3C(=O)OCH_2C_2F_5$, $CF_3C(=O)OCH_2CF_2CF_2H$, $CF_3C(=O)OCH_2CF_3$, and $CF_3C(=O)OCH(CF_3)_2$ are particularly preferred.

The cyclic ether is preferably a C3-C6 cyclic ether.

Examples of the C3-C6 cyclic ether include 1,3-dioxane, 2-methyl-1,3-dioxane, 4-methyl-1,3-dioxane, 1,4-dioxane, and fluorinated compounds thereof. Preferred are dimethoxy methane, diethoxy methane, ethoxy methoxy methane, ethylene glycol n-propyl ether, ethylene glycol di-n-butyl ether, and diethylene glycol dimethyl ether because they have a high ability to solvate with lithium ions and improve the degree of ion dissociation. Particularly preferred are dimethoxy methane, diethoxy methane, and ethoxy methoxy methane because they have a low viscosity and give a high ion conductivity.

Examples of the nitrogen-containing compound include carboxylic acid amide, fluorine-containing carboxylic acid amide, sulfonic acid amide, and fluorine-containing sulfonic acid amide. Also, 1-methyl-2-pyrrolidinone, 1-methyl-2-piperidone, 3-methyl-2-oxazilidinone, 1,3-dimethyl-2-imidazolidinone, and N-methylsuccinimide may be used.

Examples of the boron-containing compounds include borate esters such as trimethyl borate and triethyl borate, boric acid ethers, and alkyl borates.

Examples of the organic silicon-containing compounds include $(CH_3)_4-Si$ and $(CH_3)_3-Si-Si(CH_3)_3$.

Examples of the fireproof agents (flame retardants) include organophosphates and phosphazene-based compounds. Examples of the organophosphates include fluoroalkyl phosphates, non-fluoroalkyl phosphates, and aryl phosphates. Particularly preferred are fluoroalkyl phosphates because they can show a flame retardant effect even at a small amount.

Specific examples of the fluoroalkyl phosphates include fluorodialkyl phosphates disclosed in JP H11-233141 A, cyclic alkyl phosphates disclosed in JP H11-283669 A, and fluorotrialkyl phosphates.

The surfactant may be any of cationic surfactants, anionic surfactants, nonionic surfactants, and amphoteric surfactants. In order to achieve good cycle characteristics and rate characteristics, the surfactant is preferably one containing a fluorine atom.

Preferred examples of such a surfactant containing a fluorine atom include fluorine-containing carboxylic acid salts represented by the following formula:

$Rf^1COO^-M^+$ (wherein $Rf^1$ is a C3-C10 fluorinated alkyl group which may optionally have an ether bond; $M^+$ is $Li^+$, $Na^+$, $K^+$, or NHR'$_3^+$ (where R's may be the same as or different from each other, and are individually H or a C1-C3 alkyl group)), and fluorine-containing sulfonic acid salts represented by the following formula:

$$Rf^2SO_3^-M^+$$

(wherein $Rf^2$ is a C3-C10 fluorinated alkyl group which may optionally have an ether bond; $M^+$ is $Li^+$, $Na^+$, $K^+$, or NHR'$_3^+$ (where R's may be the same as or different from each other, and are individually H or a C1-C3 alkyl group)).

In order to reduce the surface tension of the electrolytic solution without impairing the charge and discharge cycle characteristics, the amount of the surfactant is preferably 0.01 to 2 mass % in the electrolytic solution.

Examples of the additives for increasing the permittivity include sulfolane, methyl sulfolane, γ-butyrolactone, γ-valerolactone, acetonitrile, and propionitrile.

Examples of the improvers for cycle characteristics and rate characteristics include methyl acetate, ethyl acetate, tetrahydrofuran, and 1,4-dioxane.

In order to suppress burst or combustion of batteries in case of overcharge, for example, the overcharge inhibitor is preferably an overcharge inhibitor having an aromatic ring. Examples of the overcharge inhibitor having an aromatic ring include aromatic compounds such as cyclohexyl benzene, biphenyl, alkyl biphenyl, terphenyl, partially hydrogenated terphenyl, t-butyl benzene, t-amyl benzene, diphenyl ether, benzofuran, dibenzofuran, dichloroaniline, and toluene; fluorinated aromatic compounds such as hexafluorobenzene, fluorobenzene, 2-fluorobiphenyl, o-cyclohexyl fluorobenzene, and p-cyclohexyl fluorobenzene; and fluoroanisole compounds such as 2,4-difluoroanisole, 2,5-difluoroanisole, 2,6-difluoroanisole, and 3,5-difluoroanisole. Preferred are aromatic compounds such as biphenyl, alkyl biphenyl, terphenyl, partially hydrogenated terphenyl, cyclohexyl benzene, t-butyl benzene, t-amyl benzene, diphenyl ether, and dibenzofuran. These compounds may be used alone or in combination of two or more. In the case of combination use of two or more compounds, preferred is a combination of cyclohexyl benzene and t-butyl benzene or t-amyl benzene, or a combination of at least one oxygen-free aromatic compound selected from biphenyl, alkyl biphenyl, terphenyl, partially hydrogenated terphenyl, cyclohexyl benzene, t-butyl benzene, t-amyl benzene, and the like, and at least one oxygen-containing aromatic compound selected from diphenyl ether, dibenzofuran, and the like. Such combinations lead to good balance between the overcharge inhibiting characteristics and the high-temperature storage characteristics.

In order to suppress burst or combustion of batteries in case of overcharge, for example, the amount of the overcharge inhibitor is preferably 0.1 to 5 mass % in the electrolytic solution.

The electrolytic solution of the present invention may further contain other known assistants to the extent that the effects of the present invention are not impaired. Examples of such known assistants include carbonate compounds such as erythritan carbonate, spiro-bis-dimethylene carbonate, and methoxy ethyl-methyl carbonate; spiro compounds such as 2,4,8,10-tetraoxaspiro[5.5]undecane and 3,9-divinyl-2,4,8,10-tetraoxaspiro[5.5]undecane; and hydrocarbon compounds such as heptane, octane, nonane, decane, and cycloheptane. These compounds may be used alone or in combination of two or more. These assistants can improve the capacity retention characteristics and the cycle characteristics after high-temperature storage.

The electrolytic solution of the present invention may be combined with a polymer material and thereby formed into a gel-like (plasticized), gel electrolytic solution.

Examples of such a polymer material include conventionally known polyethylene oxide and polypropylene oxide, modified products thereof (see JP H08-222270 A, JP 2002-100405 A); polyacrylate-based polymers, polyacrylonitrile, and fluororesins such as polyvinylidene fluoride and vinylidene fluoride-hexafluoropropylene copolymers (see JP H04-506726 T, JP H08-507407 T, JP H10-294131 A); and composites of any of these fluororesins and any hydrocarbon resin (see JP H11-35765 A, JP H11-86630 A). In particular, polyvinylidene fluoride or a vinylidene fluoride-hexafluoropropylene copolymer is preferably used as a polymer material for gel electrolytes.

The electrolytic solution of the present invention may also contain an ion conductive compound disclosed in Japanese Patent Application No. 2004-301934.

This ion conductive compound is an amorphous fluoropolyether compound having a fluorine-containing group at a side chain and is represented by formula (1-1):

$$A\text{-}(D)\text{-}B \quad (1\text{-}1)$$

wherein D is represented by formula (2-1):

$$\text{-}(D1)_n\text{—}(FAE)_m\text{-}(AE)_p\text{-}(Y)_q\text{—} \quad (2\text{-}1)$$

[wherein D1 is an ether unit having a fluoroether group at a side chain and is represented by formula (2a):

(2a)

(wherein Rf is a fluoroether group which may optionally have a cross-linkable functional group; and $R^{10}$ is a group or a bond that links Rf and the main chain);

FAE is an ether unit having a fluorinated alkyl group at a side chain and is represented by formula (2b):

(2b)

(wherein Rfa is a hydrogen atom or a fluorinated alkyl group which may optionally have a cross-linkable functional group; and $R^{11}$ is a group or a bond that links Rfa and the main chain);

AE is an ether unit represented by formula (2c):

(2c)

(wherein $R^{13}$ is a hydrogen atom, an alkyl group which may optionally have a cross-linkable functional group, an aliphatic cyclic hydrocarbon group which may optionally have a cross-linkable functional group, or an aromatic hydrocarbon group which may optionally have a cross-linkable functional group; and $R^{12}$ is a group or a bond that links $R^{13}$ and the main chain);

Y is a unit having at least one selected from the formulas (2d-1) to (2d-3):

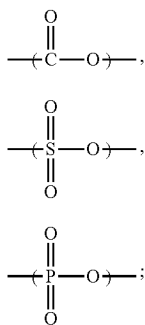

(2d-1)
(2d-2)
(2d-3)

n is an integer of 0 to 200;
m is an integer of 0 to 200;
p is an integer of 0 to 10000;
q is an integer of 1 to 100;
n+m is not 0; and
the bonding order of D1, FAE, AE, and Y is not specified]; and A and B may be the same as or different from each other, and are individually a hydrogen atom, an alkyl group which may optionally have a fluorine atom and/or a cross-linkable functional group, a phenyl group which may optionally have a fluorine atom and/or a cross-linkable functional group, a —COOH group, —OR (where R is a hydrogen atom or an alkyl group which may optionally have a fluorine atom and/or a cross-linkable functional group), an ester group, or a carbonate group (if an end of D is an oxygen atom, A and B each are none of a —COOH group, —OR, an ester group, and a carbonate group).

The electrolytic solution of the present invention may further contain other additives, if necessary. Examples of such other additives include metal oxides and glass.

The electrolytic solution of the present invention preferably contains 0.5 to 70 ppm of HF. Containing HF promotes formation of a film of an additive. If the amount of HF is too small, the ability of an additive to form the film on a negative electrode tends to be poor, and the battery characteristics tend to be poor. If the amount of HF is too large, the HF tends to have an influence on the electrolytic solution, so that the oxidation resistance tends to be low. The electrolytic solution of the present invention does not deteriorate the capacity recovery rate under high-temperature storage of batteries even if it contains HF in an amount within the above range.

The amount of HF is more preferably 1 ppm or more, still more preferably 2.5 ppm or more. The amount of HF is more preferably 60 ppm or less, still more preferably 50 ppm or less, particularly preferably 30 ppm or less.

The amount of HF can be determined by neutralization titration.

The electrolytic solution of the present invention may be prepared by any method using the aforementioned components.

The electrolytic solution of the present invention can be suitably applied to electrochemical devices such as lithium ion secondary batteries and electric double-layer capacitors. Such an electrochemical device including the electrolytic solution of the present invention is also one aspect of the present invention.

Examples of the electrochemical devices include lithium ion secondary batteries, capacitors (electric double-layer capacitors), radical batteries, solar cells (in particular, dye-sensitized solar cells), fuel cells, various electrochemical sensors, electrochromic elements, electrochemical switching elements, aluminum electrolytic capacitors, and tantalum electrolytic capacitors. Preferred are lithium ion secondary batteries and electric double-layer capacitors.

The lithium ion secondary battery may include a positive electrode, a negative electrode, and the aforementioned electrolytic solution.

<Positive Electrode>

The positive electrode is formed from a positive electrode mixture containing a positive electrode active material, which is a material of the positive electrode, and a current collector.

The positive electrode active material may be any material that can electrochemically occlude and release lithium ions. For example, a substance containing lithium and at least one transition metal is preferred. Specific examples thereof include lithium-containing transition metal complex oxides and lithium-containing transition metal phosphoric acid compounds. In particular, the positive electrode active material is preferably a lithium-containing transition metal complex oxide that generates a high voltage.

Examples of the lithium-containing transition metal complex oxides include lithium-manganese spinel complex oxides represented by the formula: $Li_aMn_{2-b}M^1_bO_4$ (wherein $0.9 \leq a$; $0 \leq b \leq 1.5$; and $M^1$ is at least one metal selected from the group consisting of Fe, Co, Ni, Cu, Zn, Al, Sn, Cr, V, Ti, Mg, Ca, Sr, B, Ga, In, Si, and Ge), lithium-nickel complex oxides represented by the formula: $LiNi_{1-c}M^2_cO_2$ (wherein $0 \leq c \leq 0.5$; and $M^2$ is at least one metal selected from the group consisting of Fe, Co, Mn, Cu, Zn, Al, Sn, Cr, V, Ti, Mg, Ca, Sr, B, Ga, In, Si, and Ge), and lithium-cobalt complex oxides represented by the formula: $LiCo_{1-d}M^3_dO_2$ (wherein $0 \leq d \leq 0.5$; and $M^3$ is at least one metal selected from the group consisting of Fe, Ni, Mn, Cu, Zn, Al, Sn, Cr, V, Ti, Mg, Ca, Sr, B, Ga, In, Si, and Ge).

In order to provide a high-power lithium ion secondary battery having a high energy density, preferred is $LiCoO_2$, $LiMnO_2$, $LiNiO_2$, $LiMn_2O_4$, $LiNi_{0.8}Co_{0.15}Al_{0.05}O_2$, or $LiNi_{1/3}Co_{1/3}Mn_{1/3}O_2$ Examples of other positive electrode active materials include $LiFePO_4$, $LiNi_{0.8}Co_{0.2}O_2$, $Li_{1.2}Fe_{0.4}Mn_{0.4}O_2$, $LiNi_{0.5}Mn_{0.5}O_2$, and $LiV_3O_6$.

In order to improve the continuous charge characteristics, the positive electrode active material preferably contains lithium phosphate. The use of lithium phosphate may be achieved in any manner, and the positive electrode active material and lithium phosphate are preferably used in admixture. The lower limit of the amount of lithium phosphate in the sum of the amounts of the positive electrode active material and the lithium phosphate is preferably 0.1 mass % or more, more preferably 0.3 mass % or more, still more preferably 0.5 mass % or more, whereas the upper limit thereof is preferably 10 mass % or less, more preferably 8 mass % or less, still more preferably 5 mass % or less.

To the surface of the positive electrode active material may be attached a substance having a composition different from the positive electrode active material. Examples of the substance attached to the surface include oxides such as aluminum oxide, silicon oxide, titanium oxide, zirconium oxide, magnesium oxide, calcium oxide, boron oxide, antimony oxide, and bismuth oxide; sulfates such as lithium sulfate, sodium sulfate, potassium sulfate, magnesium sulfate, calcium sulfate, and aluminum sulfate; carbonates such as lithium carbonate, calcium carbonate, and magnesium carbonate; and carbon.

Such a substance may be attached to the surface of the positive electrode active material by, for example, a method of dissolving or suspending the substance in a solvent, impregnating the solution or suspension into the positive electrode active material, and drying the impregnated material; a method of dissolving or suspending a precursor of the substance in a solvent, impregnating the solution or suspension into the positive electrode active material, and reacting the material and the precursor by heating; or a method of adding the substance to a precursor of the positive electrode active material and simultaneously sintering the materials. In the case where carbon is to be attached, a carbonaceous material in the form of activated carbon, for example, may be mechanically attached to the surface afterward.

The lower limit of the amount (in terms of mass) of the substance attached to the surface relative to the amount of the positive electrode active material is preferably 0.1 ppm or more, more preferably 1 ppm or more, still more preferably 10 ppm or more, whereas the upper limit thereof is preferably 20% or less, more preferably 10% or less, still more preferably 5% or less. The substance attached to the surface suppresses the oxidation of the electrolytic solution on the surface of the positive electrode active material, so that the battery life is improved. If the amount thereof is too small, the substance fails to sufficiently provide the effect. If the amount thereof is too large, the substance may hinder the entrance and exit of lithium ions, so that the resistance may be increased.

Particles of the positive electrode active material may have any conventionally used shape, such as an agglomerative shape, a polyhedral shape, a spherical shape, an ellipsoidal shape, a plate shape, a needle shape, or a pillar shape. The primary particles may agglomerate to form secondary particles.

The positive electrode active material has a tap density of preferably 0.5 g/cm$^3$ or higher, more preferably 0.8 g/cm$^3$ or higher, still more preferably 1.0 g/cm$^3$ or higher. If the tap density of the positive electrode active material is below the lower limit, an increased amount of a dispersion medium is required, as well as increased amounts of a conductive material and a binder are required in formation of a positive electrode active material layer. Thus, the filling rate of the positive electrode active material into the positive electrode active material layer may be limited and the battery capacity may be limited. With a complex oxide powder having a high tap density, a positive electrode active material layer with a high density can be formed. The tap density is preferably as high as possible and has no upper limit, in general. Still, if the tap density is too high, diffusion of lithium ions in the positive electrode active material layer with the electrolytic solution serving as a diffusion medium may function as a rate-determining step, so that the load characteristics may be easily impaired. Thus, the upper limit of the tap density is preferably 4.0 g/cm$^3$ or lower, more preferably 3.7 g/cm$^3$ or lower, still more preferably 3.5 g/cm$^3$ or lower.

In the present invention, the tap density is determined as a powder filling density (tap density) g/cm$^3$ when 5 to 10 g of the positive electrode active material powder is filled into a 10-ml glass graduated cylinder and the cylinder is tapped 200 times with a stroke of about 20 mm.

The particles of the positive electrode active material have a median size d50 (if the primary particles agglomerate to form secondary particles, the secondary particle size) of preferably 0.3 μm or greater, more preferably 0.5 μm or greater, still more preferably 0.8 μm or greater, most preferably 1.0 μm or greater, while preferably 30 μm or smaller, more preferably 27 μm or smaller, still more preferably 25 μm or smaller, most preferably 22 μm or smaller. If the median size is below the lower limit, products with a high tap density may not be obtained. If the median size exceeds the upper limit, diffusion of lithium in the particles may take a long time, so that the battery performance may be poor or streaks may be formed in formation of positive electrodes for batteries, i.e., when the active material and components such as a conductive material and a binder are formed into slurry by adding a solvent and the slurry is applied in the form of a film, for example. Mixing two or more positive electrode active materials having different median sizes d50 leads to further improved filling in formation of positive electrodes.

In the present invention, the median size d50 is determined using a known laser diffraction/scattering particle size distribution analyzer. In the case of using LA-920 (Horiba, Ltd.) as the particle size distribution analyzer, the dispersion medium used in the measurement is a 0.1 mass % sodium hexametaphosphate aqueous solution and the measurement refractive index is set to 1.24 after 5-minute ultrasonic dispersion.

If the primary particles agglomerate to form secondary particles, the average primary particle size of the positive electrode active material is preferably 0.05 μm or greater, more preferably 0.1 μm or greater, still more preferably 0.2 μm or greater. The upper limit thereof is preferably 5 μm or smaller, more preferably 4 μm or smaller, still more preferably 3 μm or smaller, most preferably 2 μm or smaller. If the average primary particle size exceeds the upper limit, spherical secondary particles are difficult to form, which may have a bad influence on the powder filling or may cause a great reduction in the specific surface area. Thus, the battery performance such as output characteristics is more likely to be impaired. In contrast, if the average primary particle size is below the lower limit, the crystals usually do not sufficiently grow. Thus, charge and discharge may be poorly reversible.

In the present invention, the primary particle size is measured by scanning electron microscopic (SEM) observation. Specifically, the primary particle size is determined as follows. A photograph at a magnification of 10000× is first taken. Any 50 primary particles are selected and the maximum length between the left and right boundary lines of each primary particle is measured along the horizontal line. Then, the average value of the maximum lengths is calculated, which is defined as the primary particle size.

The positive electrode active material has a BET specific surface area of preferably 0.1 m$^2$/g or larger, more preferably 0.2 m$^2$/g or larger, still more preferably 0.3 m$^2$/g or larger. The upper limit of the BET specific surface area is preferably 50 m$^2$/g or smaller, more preferably 40 m$^2$/g or smaller, still more preferably 30 m$^2$/g or smaller. If the BET specific surface area is smaller than the above range, the battery performance may be easily impaired. If it is larger than the above range, the tap density is less likely to be high and formation of the positive electrode active material layer may involve a difficulty in applying the material.

In the present invention, the BET specific surface area is defined by a value determined by single point BET nitrogen adsorption utilizing a gas flow method using a surface area analyzer (e.g., fully automatic surface area measurement device, Ohkura Riken Co., Ltd.), a sample pre-dried in the stream of nitrogen at 150° C. for 30 minutes, and a nitrogenhelium gas mixture with the nitrogen pressure relative to the atmospheric pressure being accurately adjusted to 0.3.

When the lithium ion secondary battery of the present invention is used as a large-size lithium ion secondary battery for hybrid vehicles or distributed generation, it is required to achieve a high output. Thus, the particles of the positive electrode active material preferably mainly include secondary particles.

The particles of the positive electrode active material preferably include 0.5 to 7.0 vol % of fine particles having an average secondary particle size of 40 µm or smaller and having an average primary particle size of 1 µm or smaller. Containing fine particles having an average primary particle size of 1 µm or smaller leads to an increase in the contact area with the electrolytic solution and more rapid diffusion of lithium ions between the electrode and the electrolytic solution. As a result, the output performance of the battery can be improved.

The positive electrode active material can be produced by any usual method of producing inorganic compounds. In particular, a spherical or ellipsoidal active material can be produced by various methods. For example, a material substance of transition metal is dissolved or crushed and dispersed in a solvent such as water, and the pH of the solution or dispersion is adjusted under stirring to form a spherical precursor. The precursor is recovered and, if necessary, dried. Then, a Li source such as LiOH, $Li_2CO_3$, or $LiNO_3$ is added thereto and the mixture is sintered at high temperature, thereby providing an active material.

In order to produce a positive electrode, the aforementioned positive electrode active materials may be used alone, or two or more thereof having different compositions may be used in combination at any ratio. Preferred examples of the combination in this case include a combination with $LiCoO_2$ and $LiMn_2O_4$ in which part of Mn may optionally be replaced by a different transition metal (e.g., $LiNi_{0.33}Co_{0.33}Mn_{0.33}O_2$), and a combination with $LiCoO_2$ in which part of Co may optionally be replaced by a different transition metal.

In order to achieve a high battery capacity, the amount of the positive electrode active material is preferably 50 to 99 mass %, more preferably 80 to 99 mass %, of the positive electrode mixture. The amount of the positive electrode active material in the positive electrode active material layer is preferably 80 mass % or more, more preferably 82 mass % or more, particularly preferably 84 mass % or more. The upper limit of the amount thereof is preferably 99 mass % or less, more preferably 98 mass % or less. Too small an amount of the positive electrode active material in the positive electrode active material layer may lead to an insufficient electric capacity. In contrast, too large an amount thereof may lead to an insufficient strength of the resulting positive electrode.

The positive electrode mixture preferably further includes a binder, a thickening agent, and a conductive material.

The binder may be any material that is safe against a solvent to be used in production of electrodes and the electrolytic solution. Examples thereof include polyvinylidene fluoride, polytetrafluoroethylene, polyethylene, polypropylene, SBR (styrene-butadiene rubber), isoprene rubber, butadiene rubber, ethylene-acrylic acid copolymers, ethylene-methacrylic acid copolymers, polyethylene terephthalate, polymethyl methacrylate, polyimide, aromatic polyamide, cellulose, nitro cellulose, NBR (acrylonitrile-butadiene rubber), fluororubber, ethylene-propylene rubber, styrene-butadiene-styrene block copolymers or hydrogenated products thereof, EPDM (ethylene-propylene-diene terpolymers), styrene-ethylene-butadiene-ethylene copolymers, styrene-isoprene-styrene block copolymers or hydrogenated products thereof, syndiotactic-1,2-polybutadiene, polyvinyl acetate, ethylene-vinyl acetate copolymers, propylene-α-olefin copolymers, fluorinated polyvinylidene fluoride, tetrafluoroethylene-ethylene copolymers, and polymer compositions having an ion conductivity of alkali metal ions (especially, lithium ions). These agents may be used alone or in any combination of two or more at any ratio.

The amount of the binder, which is expressed as the proportion of the binder in the positive electrode active material layer, is usually 0.1 mass % or more, preferably 1 mass % or more, more preferably 1.5 mass % or more. The proportion is also usually 80 mass % or less, preferably 60 mass % or less, still more preferably 40 mass % or less, most preferably 10 mass % or less. Too low a proportion of the binder may fail to sufficiently hold the positive electrode active material so that the resulting positive electrode may have an insufficient mechanical strength, resulting in deteriorated battery performance such as cycle characteristics. In contrast, too high a proportion thereof may lead to a reduction in battery capacity and conductivity.

Examples of the thickening agent include carboxymethyl cellulose, methyl cellulose, hydroxymethyl cellulose, ethyl cellulose, polyvinyl alcohol, oxidized starch, monostarch phosphate, casein, and salts thereof. These agents may be used alone or in any combination of two or more at any ratio.

The proportion of the thickening agent relative to the active material is usually 0.1 mass % or more, preferably 0.2 mass % or more, more preferably 0.3 mass % or more. It is usually 5 mass % or less, preferably 3 mass % or less, more preferably 2 mass % or less. If the proportion thereof is below this range, easiness of application may be significantly impaired. If the proportion is above this range, the proportion of the active material in the positive electrode active material layer is low, so that the capacity of the battery may be low or the resistance between the positive electrode active materials may be high.

The conductive material may be any known conductive material. Specific examples thereof include metal materials such as copper and nickel, and carbon materials such as graphite (e.g., natural graphite, artificial graphite), carbon black (e.g., acetylene black), and amorphous carbon (e.g., needle coke). These materials may be used alone or in any combination of two or more at any ratio. The conductive material is used such that the amount thereof in the positive electrode active material layer is usually 0.01 mass % or more, preferably 0.1 mass % or more, more preferably 1 mass % or more, while usually 50 mass % or less, preferably 30 mass % or less, more preferably 15 mass % or less. If the amount thereof is below this range, the conductivity may be insufficient. In contrast, if the amount thereof is above this range, the battery capacity may be low.

The solvent for forming slurry may be any solvent that can dissolve or disperse therein the positive electrode active material, the conductive material, and the binder, as well as a thickening agent used if necessary. The solvent may be either of an aqueous solvent or an organic solvent. Examples of the aqueous solvent include water and solvent mixtures of an alcohol and water. Examples of the organic solvent include aliphatic hydrocarbons such as hexane; aromatic hydrocarbons such as benzene, toluene, xylene, and methyl naphthalene; heterocyclic compounds such as quinoline and pyridine; ketones such as acetone, methyl ethyl ketone, and cyclohexanone; esters such as methyl acetate and methyl acrylate; amines such as diethylene triamine and N,N-dimethylaminopropylamine; ethers such as diethyl ether, propylene oxide, and tetrahydrofuran (THF); amides such as N-methylpyrrolidone (NMP), dimethyl formamide, and dimethyl acetamide; and aprotic polar solvents such as hexamethyl phospharamide and dimethyl sulfoxide.

The current collector for positive electrodes may be formed from any metal material such as aluminum, titanium, tantalum, stainless steel, or nickel, or any alloy thereof; or any carbon material such as carbon cloth or carbon paper. Preferred is any metal material, especially aluminum or alloy thereof.

In the case of a metal material, the current collector may be in the form of metal foil, metal cylinder, metal coil, metal plate, metal film, expanded metal, punched metal, metal foam, or the like. In the case of a carbon material, it may be in the form of carbon plate, carbon film, carbon cylinder, or the like. Preferred among these is a metal film. The film may be in the form of mesh, as appropriate. The film may have any thickness, and the thickness is usually 1 µm or greater, preferably 3 µm or greater, more preferably 5 µm or greater, while usually 1 mm or smaller, preferably 100 µm or smaller, more preferably 50 µm or smaller. If the film is thinner than this range, it may have an insufficient strength as a current collector. In contrast, if the film is thicker than this range, it may have poor handleability.

In order to reduce the electric contact resistance between the current collector and the positive electrode active material layer, the current collector also preferably has a conductive auxiliary agent applied on the surface thereof. Examples of the conductive auxiliary agent include carbon and noble metals such as gold, platinum, and silver.

The ratio between the thicknesses of the current collector and the positive electrode active material layer may be any value, and the ratio {(thickness of positive electrode active material layer on one side immediately before injection of electrolytic solution)/(thickness of current collector)} is preferably 20 or lower, more preferably 15 or lower, most preferably 10 or lower. The ratio is also preferably 0.5 or higher, more preferably 0.8 or higher, most preferably 1 or higher. If the ratio exceeds this range, the current collector may generate heat due to Joule heating during high-current-density charge and discharge. If the ratio is below this range, the ratio by volume of the current collector to the positive electrode active material is so high that the capacity of the battery may be low.

The positive electrode may be produced by a usual method. One example of the production method is a method in which the positive electrode active material is mixed with the aforementioned binder, thickening agent, conductive material, solvent, and other components to form a slurry-like positive electrode mixture, and then this mixture is applied to a current collector, dried, and pressed so as to be densified.

The densification may be achieved using a manual press or a roll press, for example. The density of the positive electrode active material layer is preferably 1.5 g/cm$^3$ or higher, more preferably 2 g/cm$^3$ or higher, still more preferably 2.2 g/cm$^3$ or higher, while preferably 5 g/cm$^3$ or lower, more preferably 4.5 g/cm$^3$ or lower, still more preferably 4 g/cm$^3$ or lower. If the density is above this range, the permeability of the electrolytic solution toward the vicinity of the interface between the current collector and the active material may be low, in particular, the charge and discharge characteristics at high current density may be impaired, so that a high output may not be achieved. If the density is below this range, the conductivity between the active materials may be low and the resistance of the battery may be high, so that a high output may not be achieved.

In order to improve the stability at high output and high temperature, the area of the positive electrode active material layer is preferably large relative to the outer surface area of an external case of the battery in the case of using the electrolytic solution of the present invention. Specifically, the sum of the areas of the positive electrodes is preferably 15 times or more, more preferably 40 times or more, greater than the surface area of the external case of the secondary battery. For closed, square-shaped cases, the outer surface area of an external case of the battery herein refers to the total area calculated from the dimension of length, width, and thickness of the case portion into which a power-generating element is filled except for a protruding portion of a terminal. For closed, cylinder-like cases, the outer surface area of an external case of the battery herein refers to a geometric surface area of an approximated cylinder of the case portion into which a power-generating element is filled except for a protruding portion of a terminal. The sum of the areas of the positive electrodes herein refers to a geometric surface area of a positive electrode mixture layer opposite to a mixture layer including the negative electrode active material. For structures including a current collector foil and positive electrode mixture layers on both sides of the current collector, the sum of the areas of the positive electrodes is the sum of the areas calculated on the respective sides.

The positive electrode plate may have any thickness. In order to achieve a high capacity and a high output, the lower limit of the thickness of the mixture layer on one side of the current collector excluding the thickness of the base metal foil is preferably 10 µm or greater, more preferably 20 µm or greater, while preferably 500 µm or smaller, more preferably 450 µm or smaller.

To the surface of the positive electrode plate may be attached a substance having a different composition. Examples of the substance attached to the surface include oxides such as aluminum oxide, silicon oxide, titanium oxide, zirconium oxide, magnesium oxide, calcium oxide, boron oxide, antimony oxide, and bismuth oxide; sulfates such as lithium sulfate, sodium sulfate, potassium sulfate, magnesium sulfate, calcium sulfate, and aluminum sulfate; carbonates such as lithium carbonate, calcium carbonate, and magnesium carbonate; and carbon.

<Negative Electrode>

The negative electrode includes a negative electrode mixture including a negative electrode active material, and a current collector.

Examples of the negative electrode active material include carbonaceous materials that can occlude and release lithium such as pyrolysates of organic matter under various pyrolysis conditions, artificial graphite, and natural graphite; metal oxide materials that can occlude and release lithium such as tin oxide and silicon oxide; lithium metals; various lithium alloys; and lithium-containing metal complex oxide materials. Two or more of these negative electrode active materials may be used in admixture.

The carbonaceous material that can occlude and release lithium is preferably artificial graphite produced by high-temperature treatment of easily graphitizable pitch from various materials, purified natural graphite, or a material obtained by surface-treating such graphite with pitch or other organic matter and then carbonizing the surface-treated graphite. In order to achieve a good balance between the initial irreversible capacity and the high-current-density charge and discharge characteristics, it is more preferably selected from carbonaceous materials obtained by one or more heat treatments at 400° C. to 3200° C. on natural graphite, artificial graphite, artificial carbonaceous substances, or artificial graphite substances; carbonaceous materials which allow the negative electrode active material layer to include at least two or more carbonaceous matters having different crystallinities and/or has an interface between the carbonaceous matters having the different crystallinities; and carbonaceous materials which allow the negative electrode active material layer to have an interface between at least two or more carbonaceous matters having different orientations. These carbonaceous materials may be used alone or in any combination of two or more at any ratio.

Examples of the carbonaceous materials obtained by one or more heat treatments at 400° C. to 3200° C. on artificial carbonaceous substances or artificial graphite substances include coal-based coke, petroleum-based coke, coal-based pitch, petroleum-based pitch, and those prepared by oxidizing these pitches; needle coke, pitch coke, and carbon materials prepared by partially graphitizing these cokes; pyrolysates of organic matter such as furnace black, acetylene black, and pitch-based carbon fibers; carbonizable organic matter and carbides thereof; and solutions prepared by dissolving carbonizable organic matter in a low-molecular-weight organic solvent such as benzene, toluene, xylene, quinoline, or n-hexane, and carbides thereof.

The metal material (excluding lithium-titanium complex oxides) to be used as the negative electrode active material may be any compound that can occlude and release lithium, and examples thereof include simple lithium, simple metals and alloys that constitute lithium alloys, and oxides, carbides, nitrides, silicides, sulfides, and phosphides thereof. The simple metals and alloys constituting lithium alloys are preferably materials containing any of metal and semi-metal elements in Groups 13 and 14, more preferably simple metal of aluminum, silicon, and tin (hereinafter, referred to as "specific metal elements"), and alloys and compounds containing any of these atoms. These materials may be used alone or in combination of two or more at any ratio.

Examples of the negative electrode active material having at least one atom selected from the specific metal elements include simple metal of any one specific metal element, alloys of two or more specific metal elements, alloys of one or two or more specific metal elements and one or two or more other metal elements, compounds containing one or two or more specific metal elements, and composite compounds such as oxides, carbides, nitrides, silicides, sulfides, and phosphides of the compounds. Use of such a simple metal, alloy, or metal compound as the negative electrode active material can give a high capacity to batteries.

Examples thereof further include compounds in which any of the above composite compounds are complexly bonded with several elements such as simple metals, alloys, and nonmetal elements. Specifically, in the case of silicon or tin, for example, an alloy of this element and a metal that does not serve as a negative electrode can be used. In the case of tin, for example, a composite compound including a combination of 5 or 6 elements, including tin, a metal (excluding silicon) that serves as a negative electrode, a metal that does not serve as a negative electrode, and a nonmetal element, can be used.

Specific examples thereof include simple Si, $SiB_4$, $SiB_6$, $Mg_2Si$, $Ni_2Si$, $TiSi_2$, $MoSi_2$, $CoSi_2$, $NiSi_2$, $CaSi_2$, $CrSi_2$, $Cu_6Si$, $FeSi_2$, $MnSi_2$, $NbSi_2$, $TaSi_2$, $VSi_2$, $WSi_2$, $ZnSi_2$, SiC, $Si_3N_4$, $Si_2N_2O$, $SiO_v$ ($0<v\leq2$), LiSiO, simple tin, $SnSiO_3$, LiSnO, $Mg_2Sn$, and $SnO_w$ ($0<w\leq2$).

Examples thereof further include composite materials of Si or Sn used as a first constitutional element, and second and third constitutional elements. The second constitutional element is at least one selected from cobalt, iron, magnesium, titanium, vanadium, chromium, manganese, nickel, copper, zinc, gallium, and zirconium, for example. The third constitutional element is at least one selected from boron, carbon, aluminum, and phosphorus, for example.

In order to achieve a high battery capacity and excellent battery characteristics, the metal material is preferably simple silicon or tin (which may contain trace impurities), $SiO_v$ ($0<v\leq2$), $SnO_w$ ($0\leq w\leq2$), a Si—Co—C composite material, a Si—Ni—C composite material, a Sn—Co—C composite material, or a Sn—Ni—C composite material.

The lithium-containing metal complex oxide material to be used as the negative electrode active material may be any material that can occlude and release lithium. In order to achieve good high-current-density charge and discharge characteristics, materials containing titanium and lithium are preferred, lithium-containing metal complex oxide materials containing titanium are more preferred, and complex oxides of lithium and titanium (hereinafter, abbreviated as "lithium titanium complex oxides") are still more preferred. In other words, use of a spinel-structured lithium titanium complex oxide contained in the negative electrode active material for electrolyte batteries is particularly preferred because such a compound markedly reduces the output resistance.

Preferred examples of the lithium titanium complex oxides include compounds represented by the formula:

$$Li_xTi_yM_zO_4$$

wherein M is at least one element selected from the group consisting of Na, K, Co, Al, Fe, Ti, Mg, Cr, Ga, Cu, Zn, and Nb.

Particularly preferred compositions are those satisfying one of the following:
(i) $1.2\leq x\leq1.4$, $1.5\leq y\leq1.7$, $z=0$
(ii) $0.9\leq x\leq1.1$, $1.9\leq y\leq2.1$, $z=0$
(iii) $0.7\leq x\leq0.9$, $2.1\leq y\leq2.3$, $z=0$
because the compound structure satisfying any of these compositions gives good balance of the battery performance.

Particularly preferred representative composition of the compound is $Li_{4/3}Ti_{5/3}O_4$ corresponding to the composition (i), $Li_1Ti_2O_4$ corresponding to the composition (ii), and $Li_{4/5}Ti_{11/5}O_4$ corresponding to the composition (iii).

Preferred examples of the structure satisfying $Z\neq0$ include $Li_{4/3}Ti_{4/3}Al_{1/3}O_4$.

The negative electrode mixture preferably further contains a binder, a thickening agent, and a conductive material.

Examples of the binder include the same binders as those mentioned for the positive electrode. The proportion of the binder relative to the negative electrode active material is preferably 0.1 mass % or more, more preferably 0.5 mass % or more, particularly preferably 0.6 mass % or more. The proportion is also preferably 20 mass % or less, more preferably 15 mass % or less, still more preferably 10 mass % or less, particularly preferably 8 mass % or less. If the proportion of the binder relative to the negative electrode active material exceeds the above range, a large amount of the binder may fail to contribute to the battery capacity, so that the battery capacity may be low. If the proportion is lower than the above range, the negative electrode may have a lowered strength.

In particular, in the case of using a rubbery polymer typified by SBR as a main component, the proportion of the binder relative to the negative electrode active material is usually 0.1 mass % or more, preferably 0.5 mass % or more, more preferably 0.6 mass % or more, while usually 5 mass % or less, preferably 3 mass % or less, more preferably 2 mass % or less. In the case of using a fluoropolymer typified by polyvinylidene fluoride as a main component, the proportion of the binder relative to the negative electrode active material is usually 1 mass % or more, preferably 2 mass % or more, more preferably 3 mass % or more, while usually 15 mass % or less, preferably 10 mass % or less, more preferably 8 mass % or less.

Examples of the thickening agent include the same thickening agents as those mentioned for the positive electrode. The proportion of the thickening agent relative to the negative electrode active material is usually 0.1 mass % or more, preferably 0.5 mass % or more, still more preferably 0.6 mass % or more, while usually 5 mass % or less, preferably 3 mass % or less, still more preferably 2 mass % or less. If the proportion of the thickening agent relative to the negative electrode active material is below the range, easiness of application may be significantly impaired. If the proportion thereof is above the range, the proportion of the negative electrode active material in the negative electrode active material layer is low, so that the capacity of the battery may be low or the resistance between the negative electrode active materials may be high.

Examples of the conductive material of the negative electrode include metal materials such as copper and nickel; and carbon materials such as graphite and carbon black.

The solvent for forming slurry may be any solvent that can dissolve or disperse the negative electrode active material and the binder, and a thickening agent and a conductive material that are used as necessary. The slurry-forming solvent may be an aqueous solvent or an organic solvent.

Examples of the aqueous solvent include water and alcohols. Examples of the organic solvent include N-methylpyrrolidone (NMP), dimethyl formamide, dimethyl acetamide, methyl ethyl ketone, cyclohexanone, methyl acetate, methyl acrylate, diethyl triamine, N,N-dimethyl aminopropyl amine, tetrahydrofuran (THF), toluene, acetone, diethyl ether, dimethyl acetamide, hexamethyl phospharamide, dimethyl sulfoxide, benzene, xylene, quinoline, pyridine, methyl naphthalene, and hexane.

Examples of the material of the current collector for negative electrodes include copper, nickel, and stainless steel. For easy processing of the material into a film and low cost, copper foil is preferred.

The current collector usually has a thickness of 1 μm or larger, preferably 5 μm or larger. The thickness is also usually 100 μm or smaller, preferably 50 μm or smaller. Too thick a negative electrode current collector may cause an excessive reduction in capacity of the whole battery, whereas too thin a current collector may be difficult to handle.

The negative electrode may be produced by a usual method. One example of the production method is a method in which the negative electrode material is mixed with the aforementioned binder, thickening agent, conductive material, solvent, and other components to form a slurry-like mixture, and then this mixture is applied to a current collector, dried, and pressed so as to be densified. In the case of using an alloyed material, a thin film layer containing the above negative electrode active material (negative electrode active material layer) can be produced by vapor deposition, sputtering, plating, or the like technique.

The electrode formed from the negative electrode active material may have any structure. The density of the negative electrode active material existing on the current collector is preferably 1 g·cm$^{-3}$ or higher, more preferably 1.2 g·cm$^{-3}$ or higher, particularly preferably 1.3 g·cm$^{-3}$ or higher, while preferably 2.2 g·cm$^{-3}$ or lower, more preferably 2.1 g·cm$^{-3}$ or lower, still more preferably 2.0 g·cm$^{-3}$ or lower, particularly preferably 1.9 g·cm$^{-3}$ or lower. If the density of the negative electrode active material existing on the current collector exceeds the above range, the particles of the negative electrode active material may be broken, the initial irreversible capacity may be high, and the permeability of the electrolytic solution toward the vicinity of the interface between the current collector and the negative electrode active material may be impaired, so that the high-current-density charge and discharge characteristics may be impaired. If the density thereof is below the above range, the conductivity between the negative electrode active materials may be impaired, the resistance of the battery may be high, and the capacity per unit volume may be low.

The thickness of the negative electrode plate is a design matter in accordance with the positive electrode plate to be used, and may be any value. The thickness of the mixture layer excluding the thickness of the base metal foil is usually 15 μm or greater, preferably 20 μm or greater, more preferably 30 μm or greater, while usually 300 μm or smaller, preferably 280 μm or smaller, more preferably 250 μm or smaller.

To the surface of the negative electrode plate may be attached a substance having a different composition. Examples of the substance attached to the surface include oxides such as aluminum oxide, silicon oxide, titanium oxide, zirconium oxide, magnesium oxide, calcium oxide, boron oxide, antimony oxide, and bismuth oxide; sulfates such as lithium sulfate, sodium sulfate, potassium sulfate, magnesium sulfate, calcium sulfate, and aluminum sulfate; and carbonates such as lithium carbonate, calcium carbonate, and magnesium carbonate.

<Separator>

The lithium ion secondary battery of the present invention preferably further includes a separator.

The separator may be formed from any known material and may have any known shape as long as the resulting separator is stable to the electrolytic solution and is excellent in a liquid-retaining ability. The separator is preferably in the form of a porous sheet or a nonwoven fabric which is formed from a material stable to the electrolytic solution of the present invention, such as resin, glass fiber, or inorganic matter, and which is excellent in a liquid-retaining ability.

Examples of the material of a resin or glass-fiber separator include polyolefins such as polyethylene and polypropylene, aromatic polyamide, polytetrafluoroethylene, polyether sulfone, and glass filters. These materials may be used alone or in any combination of two or more at any ratio, for example, in the form of a polypropylene/polyethylene bilayer film or a polypropylene/polyethylene/polypropylene trilayer film. In order to achieve good permeability of the electrolytic solution and a good shut-down effect, the separator is particularly preferably a porous sheet or a nonwoven fabric formed from polyolefin such as polyethylene or polypropylene.

The separator may have any thickness, and the thickness is usually 1 μm or larger, preferably 5 μm or larger, more preferably 8 μm or larger, while usually 50 μm or smaller, preferably 40 μm or smaller, more preferably 30 μm or smaller. If the separator is thinner than the above range, the insulation and mechanical strength may be poor. If the separator is thicker than the above range, not only the battery performance, such as rate characteristics, may be poor but also the energy density of the whole electrolyte battery may be low.

If the separator is a porous one such as a porous sheet or a nonwoven fabric, the separator may have any porosity. The porosity is usually 20% or higher, preferably 35% or higher, more preferably 45% or higher, whereas the porosity is usually 90% or lower, preferably 85% or lower, more preferably 75% or lower. If the porosity is lower than the range, the film resistance tends to be high and the rate characteristics tend to be poor. If the porosity is higher than the range, the mechanical strength of the separator tends to be low and the insulation tends to be poor.

The separator may also have any average pore size. The average pore size is usually 0.5 µm or smaller, preferably 0.2 µm or smaller, while usually 0.05 µm or larger. If the average pore size exceeds the range, short circuits may easily occur. If the average pore size is lower than the range, the film resistance may be high and the rate characteristics may be poor.

Examples of the inorganic material include oxides such as alumina and silicon dioxide, nitrides such as aluminum nitride and silicon nitride, and sulfates such as barium sulfate and calcium sulfate. The inorganic material is in the form of particles or fibers.

The separator is in the form of a thin film such as a nonwoven fabric, a woven fabric, or a microporous film. The thin film favorably has a pore size of 0.01 to 1 µm and a thickness of 5 to 50 µm. In addition to the form of the above separate thin film, the separator may have a structure in which a composite porous layer containing particles of the above inorganic material is formed on the surface of one or both of the positive and negative electrodes using a resin binder. For example, alumina particles having a 90% particle size of smaller than 1 µm are applied to the respective surfaces of the positive electrode with fluororesin used as a binder to form a porous layer.

<Battery Design>

The electrode group may be either a laminated structure including the above positive and negative electrode plates with the above separator in between, or a wound structure including the above positive and negative electrode plates in spiral with the above separator in between. The proportion of the volume of the electrode group in the battery internal volume (hereinafter, referred to as an electrode group proportion) is usually 40% or higher, preferably 50% or higher, while usually 90% or lower, preferably 80% or lower.

If the electrode group proportion is lower than the above range, the battery capacity may be low. If the electrode group proportion exceeds the above range, the battery may have small space for voids. Thus, when the battery temperature rises to high temperature, the components may swell or the liquid fraction of the electrolytic solution shows a high vapor pressure, so that the internal pressure rises. As a result, the battery characteristics such as charge and discharge repeatability and the high-temperature storage ability may be impaired, and a gas-releasing valve for releasing the internal pressure toward the outside may work.

The current collecting structure may be any structure. In order to more effectively improve the high-current-density charge and discharge characteristics by the electrolytic solution of the present invention, the current collecting structure is preferably a structure which reduces the resistances at wiring portions and jointing portions. When the internal resistance is reduced in such a manner, the effects of using the electrolytic solution of the present invention can particularly favorably be achieved.

In an electrode group having the layered structure, the metal core portions of the respective electrode layers are preferably bundled and welded to a terminal. If an electrode has a large area, the internal resistance is high. Thus, multiple terminals may preferably be formed in the electrode to reduce the resistance. In an electrode group having the wound structure, multiple lead structures may be disposed on each of the positive electrode and the negative electrode and bundled to a terminal. Thereby, the internal resistance can be reduced.

The external case may be made of any material that is stable to an electrolytic solution to be used. Specific examples thereof include metals such as nickel-plated steel plates, stainless steel, aluminum and aluminum alloys, and magnesium alloys, and a layered film (laminate film) of resin and aluminum foil. In order to reduce the weight, a metal such as aluminum or an aluminum alloy or a laminate film is favorably used.

External cases made of metal may have a sealed up structure formed by welding the metal by laser welding, resistance welding, or ultrasonic welding or a caulking structure using the metal via a resin gasket. External cases made of a laminate film may have a sealed up structure formed by hot melting the resin layers. In order to improve the sealability, a resin which is different from the resin of the laminate film may be disposed between the resin layers. Especially, in the case of forming a sealed up structure by hot melting the resin layers via current collecting terminals, metal and resin are to be bonded. Thus, the resin to be disposed between the resin layers is favorably a resin having a polar group or a modified resin having a polar group introduced thereinto.

The lithium ion secondary battery of the present invention may have any shape, and examples thereof include cylindrical batteries, square batteries, laminated batteries, coin batteries, and large-size batteries. The shapes and the configurations of the positive electrode, the negative electrode, and the separator may be changed in accordance with the shape of the battery.

A module including the lithium ion secondary battery of the present invention is also one aspect of the present invention.

The electric double-layer capacitor may contain a positive electrode, a negative electrode, and the electrolytic solution described above.

In the electric double-layer capacitor, at least one of the positive electrode and the negative electrode is a polarizable electrode. Examples of the polarizable electrode and a non-polarizable electrode include the following electrodes specifically disclosed in JP H09-7896 A.

The polarizable electrode mainly containing activated carbon that can be used in the present invention is preferably one containing inactivated carbon having a large specific surface area and a conductive material, such as carbon black, providing electronic conductivity. The polarizable electrode can be formed by any of various methods. For example, a polarizable electrode including activated carbon and carbon black can be produced by mixing activated carbon powder, carbon black, and phenolic resin, press-molding the mixture, and then sintering and activating the mixture in an inert gas atmosphere and water vapor atmosphere. Preferably, this polarizable electrode is bonded to a current collector using a conductive adhesive, for example.

Alternatively, a polarizable electrode can also be formed by kneading activated carbon powder, carbon black, and a binder in the presence of alcohol and forming the mixture into a sheet shape, and then drying the sheet. This binder may be polytetrafluoroethylene, for example. Alternatively, a polarizable electrode integrated with a current collector can be produced by mixing activated carbon powder, carbon black, a binder, and a solvent to form slurry, applying this slurry to metal foil of a current collector, and then drying the slurry.

The electric double-layer capacitor may have polarizable electrodes mainly containing activated carbon on the respective sides. Still, the electric double-layer capacitor may have a non-polarizable electrode on one side, for example, a positive electrode mainly including an electrode active material such as a metal oxide and a negative electrode including a polarizable electrode that mainly contains activated carbon may be combined; or a negative electrode mainly including a carbon material that can reversibly occlude and release lithium ions or a negative electrode of lithium metal or lithium alloy and a polarizable positive electrode mainly including activated carbon may be combined.

In place of or in combination with activated carbon, any carbonaceous material such as carbon black, graphite, expanded graphite, porous carbon, carbon nanotube, carbon nanohorn, and Kethenblack may be used.

The non-polarizable electrode is preferably an electrode mainly containing a carbon material that can reversibly occlude and release lithium ions, and this carbon material is made to occlude lithium ions in advance. In this case, the electrolyte used is a lithium salt. The electric double-layer capacitor having such a configuration achieves a much higher withstand voltage of exceeding 4 V.

The solvent used in preparation of slurry in the production of electrodes is preferably one that dissolves a binder. In accordance with the type of a binder, N-methylpyrrolidone, dimethyl formamide, toluene, xylene, isophorone, methyl ethyl ketone, ethyl acetate, methyl acetate, dimethyl phthalate, ethanol, methanol, butanol, or water is appropriately selected.

Examples of the activated carbon used for the polarizable electrode include phenol resin-type activated carbon, coconut shell-type activated carbon, and petroleum coke-type activated carbon. In order to achieve a large capacity, petroleum coke-type activated carbon or phenol resin-type activated carbon is preferably used. Examples of methods of activating the activated carbon include steam activation and molten KOH activation. In order to achieve a larger capacity, activated carbon prepared by molten KOH activation is preferably used.

Preferred examples of the conductive material used for the polarizable electrode include carbon black, Ketjenblack, acetylene black, natural graphite, artificial graphite, metal fiber, conductive titanium oxide, and ruthenium oxide. In order to achieve good conductivity (i.e., low internal resistance), and because too large an amount thereof may lead to a decreased capacity of the product, the amount of the conductive material such as carbon black used for the polarizable electrode is preferably 1 to 50 mass % in the sum of the amounts of the activated carbon and the conductive material.

In order to provide an electric double-layer capacitor having a large capacity and a low internal resistance, the activated carbon used for the polarizable electrode preferably has an average particle size of 20 μm or smaller and a specific surface area of 1500 to 3000 $m^2/g$. Preferred examples of the carbon material for providing an electrode mainly containing a carbon material that can reversibly occlude and release lithium ions include natural graphite, artificial graphite, graphitized mesocarbon microsphere, graphitized whisker, vapor-grown carbon fiber, sintered furfuryl alcohol resin, and sintered novolak resin.

The current collector may be any chemically and electrochemically corrosion-resistant one. Preferred examples of the current collector used for the polarizable electrode mainly containing activated carbon include stainless steel, aluminum, titanium, and tantalum. Particularly preferred materials in terms of the characteristics and cost of the resulting electric double-layer capacitor are stainless steel and aluminum. Preferred examples of the current collector used for the electrode mainly containing a carbon material that can reversibly occlude and release lithium ions include stainless steel, copper, and nickel.

The carbon material that can reversibly occlude and release lithium ions can be allowed to occlude lithium ions in advance by (1) a method of mixing powdery lithium to a carbon material that can reversibly occlude and release lithium ions, (2) a method of placing lithium foil on an electrode including a carbon material that can reversibly occlude and release lithium ions and a binder so that the lithium foil is electrically in contact with the electrode, immersing this electrode in an electrolytic solution containing a lithium salt dissolved therein so that the lithium is ionized, and allowing the carbon material to take in the resulting lithium ions, or (3) a method of placing an electrode including a carbon material that can reversibly occlude and release lithium ions and a binder at a minus side and placing a lithium metal at a plus side, immersing the electrodes in a non-aqueous electrolytic solution containing a lithium salt as an electrolyte, and supplying a current so that the carbon material is allowed to electrochemically take in the ionized lithium.

Examples of known electric double-layer capacitors include wound electric double-layer capacitors, laminated electric double-layer capacitors, and coin-type electric double-layer capacitors. The electric double-layer capacitor of the present invention may also be any of these types.

For example, a wound electric double-layer capacitor is assembled by winding a positive electrode and a negative electrode each of which includes a laminate (electrode) of a current collector and an electrode layer, and a separator in between to provide a wound element, putting this wound element in a case made of, for example, aluminum, filling the case with an electrolytic solution, preferably a non-aqueous electrolytic solution, and sealing the case with a rubber sealant.

A separator formed from a conventionally known material and having a conventionally known structure can be used. Examples thereof include polyethylene porous membranes, and nonwoven fabric of polypropylene fiber, glass fiber, or cellulose fiber.

In accordance with any known method, the capacitor may be formed into a laminated electric double-layer capacitor in which a sheet-like positive electrode and negative electrode are stacked with an electrolytic solution and a separator in between or a coin-type electric double-layer capacitor in which a positive electrode and a negative electrode are fixed by a gasket with an electrolytic solution and a separator in between.

The electrolytic solution of the present invention is useful as an electrolytic solution for large-size lithium ion secondary batteries for hybrid vehicles or distributed generation, and for electric double-layer capacitors.

EXAMPLES

The present invention will be described with reference to, but not limited to, examples.

(Preparation of Electrolytic Solution)

The components were mixed in accordance with the compositions shown in the tables. To each mixture was added LiPF$_6$ to a concentration of 1.0 mol/L. Thereby, an electrolytic solution was prepared.

The compounds shown in the tables are as follows.

Solvent

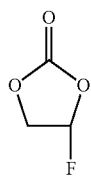
FA1-1

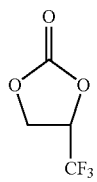
FA1-5

CH$_3$OCOOCH$_2$CF$_3$    FA2-1

CF$_3$CF$_2$CH$_2$OCF$_2$CF$_2$H    FA3-1

Compound A

a

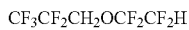
b

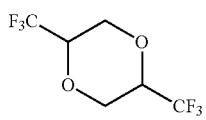
c

Compound B

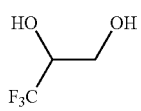
I

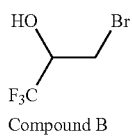
II

LiPO$_2$F$_2$    III

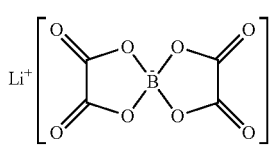
IV

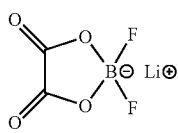
V

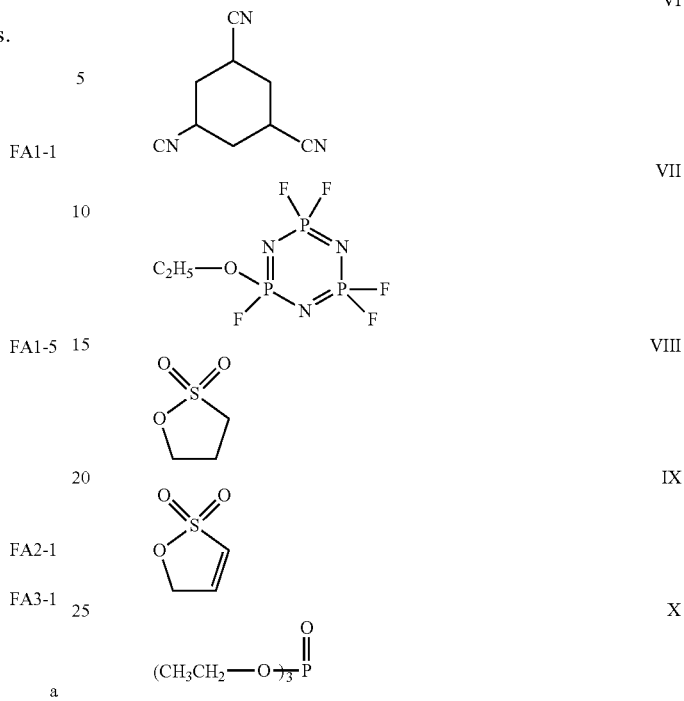

-continued

VI, VII, VIII, IX, X

With the resulting electrolytic solutions, lithium ion secondary batteries were produced as follows.

(Production of Positive Electrode)

LiNi$_{0.5}$Mn$_{1.5}$O$_4$ serving as a positive electrode active material, acetylene black serving as a conductive material, and dispersion of polyvinylidene fluoride (PVdF) in N-methyl-2-pyrrolidone serving as a binding agent were mixed such that the solid content ratio of the active material, the conductive material, and the binding agent was 92/3/5 (mass % ratio). Thereby, positive electrode mixture slurry was prepared. The resulting positive electrode mixture slurry was uniformly applied onto a 20-μm-thick aluminum foil current collector and dried, and then the workpiece was compression molded using a press. Thereby, a positive electrode was produced.

(Production of Negative Electrode)

Artificial graphite powder serving as a negative electrode active material, an aqueous dispersion of sodium carboxymethyl cellulose (concentration of sodium carboxymethyl cellulose: 1% by mass) serving as a thickening agent, and an aqueous dispersion of styrene-butadiene rubber (concentration of styrene-butadiene rubber: 50% by mass) serving as a binding agent were mixed into a slurry-like form in an aqueous solvent such that the solid content ratio of the active material, the thickening agent, and the binding agent was 97.6/1.2/1.2 (mass % ratio). Thereby, negative electrode mixture slurry was prepared. The slurry was uniformly applied to 20-μm-thick copper foil and dried, and then the workpiece was compression molded using a press. Thereby, a negative electrode was produced.

(Production of Lithium Ion Secondary Battery)

The negative electrode and positive electrode produced as mentioned above and a polyethylene separator were stacked in the order of the negative electrode, the separator, and the positive electrode, whereby a battery element was produced.

This battery element was inserted into a bag made from a laminate film consisting of an aluminum sheet (thickness: 40

µm) and resin layers covering the respective faces of the sheet, with the terminals of the positive electrode and the negative electrode protruding from the bag. Then, the bag was charged with one of the electrolytic solutions and vacuum-sealed. Thereby, a sheet-like lithium ion secondary battery was produced.

<Evaluation of Gas Volume Before and after High-Temperature Storage>

A cycle of charge and discharge under predetermined charge and discharge conditions (0.5 C charge with a predetermined voltage until 0.1 C charge current, and discharge at a current corresponding to 1 C until 3.0 V) was defined as one cycle and the initial discharge capacity was determined from the discharge capacity of the third cycle. The battery was again subjected to CC/CV charge (cutoff: 0.1 C) to 4.75 V, and then the gas volume was measured. After the gas volume measurement, the produced secondary battery was stored at 85° C. for 24 hours. After storage, the gas volume of the secondary battery after the high-temperature storage test was measured. The temperature for the gas volume measurement was 25° C. The gas volume was determined by the following formula.

Volume of gas generated (ml)=(gas volume after high-temperature storage (ml))−(gas volume before high-temperature storage (ml))

<Test of High-Temperature Storage Characteristics>

The above produced secondary battery in the state of being sandwiched and pressurized between plates was subjected to constant current-constant voltage charge (hereinafter, referred to as CC/CV charge) (0.1 C cut off) to 4.35 V at a current corresponding to 0.2 C at 25° C. Then, the battery was discharged to 3 V at a constant current of 0.2 C. This process was counted as one cycle. The initial discharge capacity was determined from the discharge capacity of the third cycle. Here, 1 C means a current value required for discharging the reference capacity of a battery in an hour. For example, 0.2 C indicates a ⅕ current value thereof. The secondary battery was again subjected to the CC/CV charge (0.1 C cut off) to 4.35V, and then stored at a high temperature of 60° C. for three days. Subsequently, the battery was discharged to 3 V at a current of 0.2 C at 25° C., and the residual capacity after high-temperature storage was measured. The ratio of the residual capacity to the initial discharge capacity was determined, and was regarded as the storage capacity retention (%).

(Residual capacity)/(initial discharge capacity)× 100=storage capacity retention (%)

Tables 1 to 3 show the results.

TABLE 1

| | Compound A | | Compound B | | Solvent | | | | Solvent composition (volume ratio) | | | | Volume of gas generated (mL) | Capacity retention at 60° C. (%) |
| | | Proportion in electrolytic solution | | Proportion in electrolytic solution | Cyclic carbonate | Acyclic carbonate | | Ether | | | | | | |
| | Type | (mass ppm) | Type | (mass %) | FA1 | FA2 | | FA3 | FA1-1 | FA1-5 | FA2 | FA3 | | |
| Example 1 | a | 0.001 | — | — | FA1-1 FA1-5 | FA2-1 | | FA3-1 | 25 | 5 | 70 | 0 | 4.01 | 77 |
| Example 2 | a | 0.01 | — | — | FA1-1 FA1-5 | FA2-1 | | FA3-1 | 25 | 5 | 70 | 0 | 3.98 | 77 |
| Example 3 | a | 0.1 | — | — | FA1-1 FA1-5 | FA2-1 | | FA3-1 | 25 | 5 | 70 | 0 | 3.93 | 78 |
| Example 4 | a | 0.5 | — | — | FA1-1 FA1-5 | FA2-1 | | FA3-1 | 25 | 5 | 70 | 0 | 3.60 | 79 |
| Example 5 | a | 5 | — | — | FA1-1 FA1-5 | FA2-1 | | FA3-1 | 25 | 5 | 70 | 0 | 3.62 | 78 |
| Example 6 | a | 20 | — | — | FA1-1 FA1-5 | FA2-1 | | FA3-1 | 25 | 5 | 70 | 0 | 3.63 | 77 |
| Example 7 | a | 100 | — | — | FA1-1 FA1-5 | FA2-1 | | FA3-1 | 25 | 5 | 70 | 0 | 3.70 | 77 |
| Example 8 | a | 500 | — | — | FA1-1 FA1-5 | FA2-1 | | FA3-1 | 25 | 5 | 70 | 0 | 3.80 | 77 |
| Example 9 | a | 1000 | — | — | FA1-1 FA1-5 | FA2-1 | | FA3-1 | 25 | 5 | 70 | 0 | 3.90 | 76 |
| Example 10 | a | 10000 | — | — | FA1-1 FA1-5 | FA2-1 | | FA3-1 | 25 | 5 | 70 | 0 | 4.10 | 75 |
| Example 11 | b | 0.001 | — | — | FA1-1 — | FA2-1 | | FA3-1 | 30 | 0 | 70 | 0 | 4.04 | 75 |
| Example 12 | b | 0.01 | — | — | FA1-1 — | FA2-1 | | FA3-1 | 30 | 0 | 70 | 0 | 3.82 | 76 |
| Example 13 | b | 0.1 | — | — | FA1-1 — | FA2-1 | | FA3-1 | 30 | 0 | 70 | 0 | 3.62 | 78 |
| Example 14 | b | 0.5 | — | — | FA1-1 — | FA2-1 | | FA3-1 | 30 | 0 | 70 | 0 | 3.66 | 77 |
| Example 15 | b | 5 | — | — | FA1-1 — | FA2-1 | | FA3-1 | 30 | 0 | 70 | 0 | 3.78 | 76 |
| Example 16 | b | 20 | — | — | FA1-1 — | FA2-1 | | FA3-1 | 30 | 0 | 70 | 0 | 3.88 | 74 |
| Example 17 | b | 100 | — | — | FA1-1 — | FA2-1 | | FA3-1 | 30 | 0 | 70 | 0 | 3.90 | 73 |
| Example 18 | b | 500 | — | — | FA1-1 — | FA2-1 | | FA3-1 | 30 | 0 | 70 | 0 | 3.93 | 72 |
| Example 19 | b | 1000 | — | — | FA1-1 — | FA2-1 | | FA3-1 | 30 | 0 | 70 | 0 | 3.96 | 70 |
| Example 20 | b | 10000 | — | — | FA1-1 — | FA2-1 | | FA3-1 | 30 | 0 | 70 | 0 | 4.09 | 68 |
| Example 21 | c | 0.001 | — | — | FA1-1 — | FA2-1 | | FA3-1 | 30 | 0 | 70 | 0 | 4.02 | 76 |
| Example 22 | c | 0.01 | — | — | FA1-1 — | FA2-1 | | FA3-1 | 30 | 0 | 70 | 0 | 3.85 | 77 |
| Example 23 | c | 0.1 | — | — | FA1-1 — | FA2-1 | | FA3-1 | 30 | 0 | 70 | 0 | 3.61 | 79 |
| Example 24 | c | 0.5 | — | — | FA1-1 — | FA2-1 | | FA3-1 | 30 | 0 | 70 | 0 | 3.69 | 78 |
| Example 25 | c | 5 | — | — | FA1-1 — | FA2-1 | | FA3-1 | 30 | 0 | 70 | 0 | 3.75 | 77 |
| Example 26 | c | 20 | — | — | FA1-1 — | FA2-1 | | FA3-1 | 30 | 0 | 70 | 0 | 3.83 | 75 |
| Example 27 | c | 100 | — | — | FA1-1 — | FA2-1 | | FA3-1 | 30 | 0 | 70 | 0 | 3.90 | 73 |
| Example 28 | c | 500 | — | — | FA1-1 — | FA2-1 | | FA3-1 | 30 | 0 | 70 | 0 | 3.95 | 71 |
| Example 29 | c | 1000 | — | — | FA1-1 — | FA2-1 | | FA3-1 | 30 | 0 | 70 | 0 | 4.05 | 69 |
| Example 30 | c | 10000 | — | — | FA1-1 — | FA2-1 | | FA3-1 | 30 | 0 | 70 | 0 | 4.15 | 67 |
| Example 31 | a | 0.5 | I | 0.001 | FA1-1 FA1-5 | FA2-1 | | FA3-1 | 25 | 5 | 70 | 0 | 3.85 | 78 |
| Example 32 | a | 0.5 | I | 0.01 | FA1-1 FA1-5 | FA2-1 | | FA3-1 | 25 | 5 | 70 | 0 | 3.70 | 79 |
| Example 33 | a | 0.5 | I | 0.1 | FA1-1 FA1-5 | FA2-1 | | FA3-1 | 25 | 5 | 70 | 0 | 3.58 | 80 |
| Example 34 | a | 0.5 | I | 1 | FA1-1 FA1-5 | FA2-1 | | FA3-1 | 25 | 5 | 70 | 0 | 3.75 | 78 |
| Example 35 | a | 0.5 | I | 10 | FA1-1 FA1-5 | FA2-1 | | FA3-1 | 25 | 5 | 70 | 0 | 3.80 | 74 |
| Example 36 | a | 0.5 | II | 0.001 | FA1-1 FA1-5 | FA2-1 | | FA3-1 | 25 | 5 | 70 | 0 | 3.82 | 77 |
| Example 37 | a | 0.5 | II | 0.01 | FA1-1 FA1-5 | FA2-1 | | FA3-1 | 25 | 5 | 70 | 0 | 3.65 | 80 |
| Example 38 | a | 0.5 | II | 0.1 | FA1-1 FA1-5 | FA2-1 | | FA3-1 | 25 | 5 | 70 | 0 | 3.57 | 81 |

TABLE 1-continued

| | Compound A | | Compound B | | Solvent | | | | | | | Volume of gas generated (mL) | Capacity retention at 60° C. (%) |
|---|---|---|---|---|---|---|---|---|---|---|---|---|---|
| | | Proportion in electrolytic solution | | Proportion in electrolytic solution | Cyclic carbonate | Acyclic carbonate | Ether | Solvent composition (volume ratio) | | | | | |
| | Type | (mass ppm) | Type | (mass %) | FA1 | FA2 | FA3 | FA1-1 | FA1-5 | FA2 | FA3 | | |
| Example 39 | a | 0.5 | II | 1 | FA1-1 FA1-5 | FA2-1 | FA3-1 | 25 | 5 | 70 | 0 | 3.68 | 79 |
| Example 40 | a | 0.5 | II | 10 | FA1-1 FA1-5 | FA2-1 | FA3-1 | 25 | 5 | 70 | 0 | 3.75 | 75 |

TABLE 2

| | Compound A | | Compound B | | Solvent | | | | | | | Volume of gas generated (mL) | Capacity retention at 60° C. (%) |
|---|---|---|---|---|---|---|---|---|---|---|---|---|---|
| | | Proportion in electrolytic solution | | Proportion in electrolytic solution | Cyclic carbonate | Acyclic carbonate | Ether | Solvent composition (volume ratio) | | | | | |
| | Type | (mass ppm) | Type | (mass %) | FA1 | FA2 | FA3 | FA1-1 | FA1-5 | FA2 | FA3 | | |
| Example 41 | a | 0.5 | III | 0.001 | FA1-1 FA1-5 | FA2-1 | FA3-1 | 25 | 5 | 70 | 0 | 3.77 | 79 |
| Example 42 | a | 0.5 | III | 0.01 | FA1-1 FA1-5 | FA2-1 | FA3-1 | 25 | 5 | 70 | 0 | 3.65 | 80 |
| Example 43 | a | 0.5 | III | 0.1 | FA1-1 FA1-5 | FA2-1 | FA3-1 | 25 | 5 | 70 | 0 | 3.54 | 82 |
| Example 44 | a | 0.5 | III | 1 | FA1-1 FA1-5 | FA2-1 | FA3-1 | 25 | 5 | 70 | 0 | 3.67 | 79 |
| Example 45 | a | 0.5 | III | 5 | FA1-1 FA1-5 | FA2-1 | FA3-1 | 25 | 5 | 70 | 0 | 3.77 | 77 |
| Example 46 | a | 0.5 | IV | 0.001 | FA1-1 FA1-5 | FA2-1 | FA3-1 | 25 | 5 | 70 | 0 | 3.76 | 78 |
| Example 47 | a | 0.5 | IV | 0.01 | FA1-1 FA1-5 | FA2-1 | FA3-1 | 25 | 5 | 70 | 0 | 3.62 | 80 |
| Example 48 | a | 0.5 | IV | 0.1 | FA1-1 FA1-5 | FA2-1 | FA3-1 | 25 | 5 | 70 | 0 | 3.56 | 81 |
| Example 49 | a | 0.5 | IV | 1 | FA1-1 FA1-5 | FA2-1 | FA3-1 | 25 | 5 | 70 | 0 | 3.67 | 79 |
| Example 50 | a | 0.5 | IV | 5 | FA1-1 FA1-5 | FA2-1 | FA3-1 | 25 | 5 | 70 | 0 | 3.80 | 77 |
| Example 51 | a | 0.5 | V | 0.001 | FA1-1 FA1-5 | FA2-1 | FA3-1 | 25 | 5 | 70 | 0 | 3.79 | 77 |
| Example 52 | a | 0.5 | V | 0.01 | FA1-1 FA1-5 | FA2-1 | FA3-1 | 25 | 5 | 70 | 0 | 3.67 | 79 |
| Example 53 | a | 0.5 | V | 0.1 | FA1-1 FA1-5 | FA2-1 | FA3-1 | 25 | 5 | 70 | 0 | 3.58 | 81 |
| Example 54 | a | 0.5 | V | 1 | FA1-1 FA1-5 | FA2-1 | FA3-1 | 25 | 5 | 70 | 0 | 3.68 | 79 |
| Example 55 | a | 0.5 | V | 20 | FA1-1 FA1-5 | FA2-1 | FA3-1 | 25 | 5 | 70 | 0 | 3.77 | 75 |
| Example 56 | a | 0.5 | VI | 0.001 | FA1-1 FA1-5 | FA2-1 | FA3-1 | 25 | 5 | 70 | 0 | 3.75 | 82 |
| Example 57 | a | 0.5 | VI | 0.01 | FA1-1 FA1-5 | FA2-1 | FA3-1 | 25 | 5 | 70 | 0 | 3.58 | 82 |
| Example 58 | a | 0.5 | VI | 0.1 | FA1-1 FA1-5 | FA2-1 | FA3-1 | 25 | 5 | 70 | 0 | 3.50 | 83 |
| Example 59 | a | 0.5 | VI | 1 | FA1-1 FA1-5 | FA2-1 | FA3-1 | 25 | 5 | 70 | 0 | 3.59 | 81 |
| Example 60 | a | 0.5 | VI | 20 | FA1-1 FA1-5 | FA2-1 | FA3-1 | 25 | 5 | 70 | 0 | 3.72 | 80 |
| Example 61 | a | 0.5 | VII | 0.001 | FA1-1 FA1-5 | FA2-1 | FA3-1 | 25 | 5 | 70 | 0 | 3.76 | 77 |
| Example 62 | a | 0.5 | VII | 0.01 | FA1-1 FA1-5 | FA2-1 | FA3-1 | 25 | 5 | 70 | 0 | 3.62 | 78 |
| Example 63 | a | 0.5 | VII | 0.1 | FA1-1 FA1-5 | FA2-1 | FA3-1 | 25 | 5 | 70 | 0 | 3.59 | 80 |
| Example 64 | a | 0.5 | VII | 1 | FA1-1 FA1-5 | FA2-1 | FA3-1 | 25 | 5 | 70 | 0 | 3.65 | 77 |
| Example 65 | a | 0.5 | VII | 20 | FA1-1 FA1-5 | FA2-1 | FA3-1 | 25 | 5 | 70 | 0 | 3.78 | 75 |
| Example 66 | a | 0.5 | VIII | 0.001 | FA1-1 FA1-5 | FA2-1 | FA3-1 | 25 | 5 | 70 | 0 | 3.80 | 79 |
| Example 67 | a | 0.5 | VIII | 0.01 | FA1-1 FA1-5 | FA2-1 | FA3-1 | 25 | 5 | 70 | 0 | 3.65 | 80 |
| Example 68 | a | 0.5 | VIII | 0.1 | FA1-1 FA1-5 | FA2-1 | FA3-1 | 25 | 5 | 70 | 0 | 3.57 | 81 |
| Example 69 | a | 0.5 | VIII | 1 | FA1-1 FA1-5 | FA2-1 | FA3-1 | 25 | 5 | 70 | 0 | 3.65 | 79 |
| Example 70 | a | 0.5 | VIII | 20 | FA1-1 FA1-5 | FA2-1 | FA3-1 | 25 | 5 | 70 | 0 | 3.79 | 76 |
| Example 71 | a | 0.5 | IX | 0.001 | FA1-1 FA1-5 | FA2-1 | FA3-1 | 25 | 5 | 70 | 0 | 3.80 | 78 |
| Example 72 | a | 0.5 | IX | 0.01 | FA1-1 FA1-5 | FA2-1 | FA3-1 | 25 | 5 | 70 | 0 | 3.65 | 80 |
| Example 73 | a | 0.5 | IX | 0.1 | FA1-1 FA1-5 | FA2-1 | FA3-1 | 25 | 5 | 70 | 0 | 3.56 | 82 |
| Example 74 | a | 0.5 | IX | 1 | FA1-1 FA1-5 | FA2-1 | FA3-1 | 25 | 5 | 70 | 0 | 3.68 | 79 |
| Example 75 | a | 0.5 | IX | 20 | FA1-1 FA1-5 | FA2-1 | FA3-1 | 25 | 5 | 70 | 0 | 3.81 | 77 |
| Example 76 | a | 0.5 | X | 0.001 | FA1-1 FA1-5 | FA2-1 | FA3-1 | 25 | 5 | 70 | 0 | 3.78 | 78 |
| Example 77 | a | 0.5 | X | 0.01 | FA1-1 FA1-5 | FA2-1 | FA3-1 | 25 | 5 | 70 | 0 | 3.66 | 79 |
| Example 78 | a | 0.5 | X | 0.1 | FA1-1 FA1-5 | FA2-1 | FA3-1 | 25 | 5 | 70 | 0 | 3.59 | 80 |
| Example 79 | a | 0.5 | X | 1 | FA1-1 FA1-5 | FA2-1 | FA3-1 | 25 | 5 | 70 | 0 | 3.68 | 78 |
| Example 80 | a | 0.5 | X | 20 | FA1-1 FA1-5 | FA2-1 | FA3-1 | 25 | 5 | 70 | 0 | 3.80 | 75 |

TABLE 3

| | Compound A | | Compound B | | Solvent | | | Solvent composition (volume ratio) | | | | Volume of gas generated (mL) | Capacity retention at 60° C. (%) |
|---|---|---|---|---|---|---|---|---|---|---|---|---|---|
| | | Proportion in electrolytic solution | | Proportion in electrolytic solution | Cyclic carbonate | Acyclic carbonate | Ether | | | | | | |
| | Type | (mass ppm) | Type | (mass %) | FA1 | FA2 | FA3 | FA1-1 | FA1-5 | FA2 | FA3 | | |
| Example 81 | b | 0.1 | I | 0.1 | FA1-1 | — | FA2-1 | FA3-1 | 30 | 0 | 70 | 0 | 3.60 | 79 |
| Example 82 | b | 0.1 | II | 0.1 | FA1-1 | — | FA2-1 | FA3-1 | 30 | 0 | 70 | 0 | 3.60 | 80 |
| Example 83 | b | 0.1 | III | 0.1 | FA1-1 | — | FA2-1 | FA3-1 | 30 | 0 | 70 | 0 | 3.62 | 80 |
| Example 84 | b | 0.1 | IV | 0.1 | FA1-1 | — | FA2-1 | FA3-1 | 30 | 0 | 70 | 0 | 3.61 | 79 |
| Example 85 | b | 0.1 | V | 0.1 | FA1-1 | — | FA2-1 | FA3-1 | 30 | 0 | 70 | 0 | 3.63 | 80 |
| Example 86 | b | 0.1 | VI | 0.1 | FA1-1 | — | FA2-1 | FA3-1 | 30 | 0 | 70 | 0 | 3.56 | 82 |
| Example 87 | b | 0.1 | VII | 0.1 | FA1-1 | — | FA2-1 | FA3-1 | 30 | 0 | 70 | 0 | 3.64 | 79 |
| Example 88 | b | 0.1 | VIII | 0.1 | FA1-1 | — | FA2-1 | FA3-1 | 30 | 0 | 70 | 0 | 3.66 | 78 |
| Example 89 | b | 0.1 | IX | 0.1 | FA1-1 | — | FA2-1 | FA3-1 | 30 | 0 | 70 | 0 | 3.60 | 81 |
| Example 90 | b | 0.1 | X | 0.1 | FA1-1 | — | FA2-1 | FA3-1 | 30 | 0 | 70 | 0 | 3.65 | 79 |
| Example 91 | c | 0.1 | I | 0.1 | FA1-1 | — | FA2-1 | FA3-1 | 30 | 0 | 70 | 0 | 3.61 | 80 |
| Example 92 | c | 0.1 | II | 0.1 | FA1-1 | — | FA2-1 | FA3-1 | 30 | 0 | 70 | 0 | 3.58 | 80 |
| Example 93 | c | 0.1 | III | 0.1 | FA1-1 | — | FA2-1 | FA3-1 | 30 | 0 | 70 | 0 | 3.60 | 81 |
| Example 94 | c | 0.1 | IV | 0.1 | FA1-1 | — | FA2-1 | FA3-1 | 30 | 0 | 70 | 0 | 3.62 | 80 |
| Example 95 | c | 0.1 | V | 0.1 | FA1-1 | — | FA2-1 | FA3-1 | 30 | 0 | 70 | 0 | 3.61 | 80 |
| Example 96 | c | 0.1 | VI | 0.1 | FA1-1 | — | FA2-1 | FA3-1 | 30 | 0 | 70 | 0 | 3.54 | 82 |
| Example 97 | c | 0.1 | VII | 0.1 | FA1-1 | — | FA2-1 | FA3-1 | 30 | 0 | 70 | 0 | 3.63 | 80 |
| Example 98 | c | 0.1 | VIII | 0.1 | FA1-1 | — | FA2-1 | FA3-1 | 30 | 0 | 70 | 0 | 3.65 | 79 |
| Example 99 | c | 0.1 | IX | 0.1 | FA1-1 | — | FA2-1 | FA3-1 | 30 | 0 | 70 | 0 | 3.62 | 80 |
| Example 100 | c | 0.1 | X | 0.1 | FA1-1 | — | FA2-1 | FA3-1 | 30 | 0 | 70 | 0 | 3.62 | 80 |
| Example 101 | a | 0.5 | VI | 0.1 | FA1-1 | FA1-5 | FA2-1 | FA3-1 | 25 | 5 | 40 | 30 | 3.42 | 85 |
| Example 102 | b | 0.1 | VI | 0.1 | FA1-1 | — | FA2-1 | FA3-1 | 30 | 0 | 40 | 30 | 3.50 | 83 |
| Example 103 | c | 0.1 | VI | 0.1 | FA1-1 | — | FA2-1 | FA3-1 | 30 | 0 | 40 | 30 | 3.52 | 83 |
| Comparative Example 1 | — | — | I | 0.1 | FA1-1 | FA1-5 | FA2-1 | FA3-1 | 25 | 5 | 40 | 30 | 4.17 | 65 |
| Comparative Example 2 | — | — | II | 0.1 | FA1-1 | FA1-5 | FA2-1 | FA3-1 | 25 | 5 | 40 | 30 | 4.18 | 65 |
| Comparative Example 3 | — | — | III | 0.1 | FA1-1 | FA1-5 | FA2-1 | FA3-1 | 25 | 5 | 40 | 30 | 4.21 | 63 |
| Comparative Example 4 | — | — | IV | 0.1 | FA1-1 | FA1-5 | FA2-1 | FA3-1 | 25 | 5 | 40 | 30 | 4.20 | 63 |
| Comparative Example 5 | — | — | V | 0.1 | FA1-1 | FA1-5 | FA2-1 | FA3-1 | 25 | 5 | 40 | 30 | 4.17 | 64 |
| Comparative Example 6 | — | — | VI | 0.1 | FA1-1 | FA1-5 | FA2-1 | FA3-1 | 25 | 5 | 40 | 30 | 4.16 | 66 |
| Comparative Example 7 | — | — | VII | 0.1 | FA1-1 | FA1-5 | FA2-1 | FA3-1 | 25 | 5 | 40 | 30 | 4.17 | 65 |
| Comparative Example 8 | — | — | VIII | 0.1 | FA1-1 | FA1-5 | FA2-1 | FA3-1 | 25 | 5 | 40 | 30 | 4.19 | 64 |
| Comparative Example 9 | — | — | IX | 0.1 | FA1-1 | FA1-5 | FA2-1 | FA3-1 | 25 | 5 | 40 | 30 | 4.20 | 66 |
| Comparative Example 10 | — | — | X | 0.1 | FA1-1 | FA1-5 | FA2-1 | FA3-1 | 25 | 5 | 40 | 30 | 4.21 | 65 |

The invention claimed is:

1. An electrolytic solution comprising:
a compound (1) represented by formula (1):

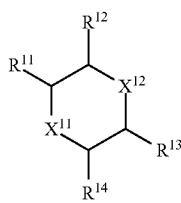

wherein $R^{11}$ and $R^{13}$ are each individually a halogenated C1-C5 alkyl group and $R^{12}$ and $R^{14}$ are H; and $X^{11}$ and $X^{12}$ are individually O or S, and
wherein the electrolytic solution contains the compound (1) in an amount of 0.001 mass ppm to 10000 mass ppm relative to the electrolytic solution.

2. The electrolytic solution according to claim 1, further comprising a solvent,
wherein the solvent contains a carbonate.

3. The electrolytic solution according to claim 1, further comprising a solvent,
wherein the solvent contains an acyclic ether.

4. The electrolytic solution according to claim 1, further comprising at least one lithium salt (X) selected from the group consisting of:
a compound (3) represented by formula (3):

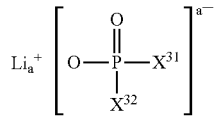

wherein $X^{31}$ and $X^{32}$ may be the same as or different from each other, and are each —H, —F, —O, —OCN, an alkyl group which may optionally have an ether bond, a fluorinated alkyl group which may optionally have an ether bond, an alkoxy group which may optionally have an ether bond, or a fluorinated alkoxy group which may optionally have an ether bond; $X^{31}$ and $X^{32}$ may be bonded to each other to form a ring; and a is an integer of 1 to 3;

a compound (4) represented by formula (4):

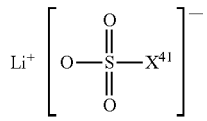

wherein $X^{41}$ is —H, —F, —Cl, an alkyl group which may optionally have an ether bond, a fluorinated alkyl group which may optionally have an ether bond, an alkoxy group which may optionally have an ether bond, or a fluorinated alkoxy group which may optionally have an ether bond;

a compound (5) represented by formula (5):

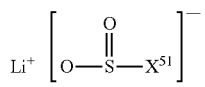

wherein $X^{51}$ is —H, —F, —Cl, an alkyl group which may optionally have an ether bond, a fluorinated alkyl group which may optionally have an ether bond, an alkoxy group which may optionally have an ether bond, or a fluorinated alkoxy group which may optionally have an ether bond; and a compound (6) represented by formula (6):

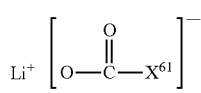

wherein $X^{61}$ is —H, —F, —Cl, an alkyl group which may optionally have an ether bond, a fluorinated alkyl group which may optionally have an ether bond, an alkoxy group which may optionally have an ether bond, or a fluorinated alkoxy group which may optionally have an ether bond.

5. The electrolytic solution according to claim 1, further comprising at least one cyclic dicarbonyl compound selected from the group consisting of:

a compound represented by formula (7):

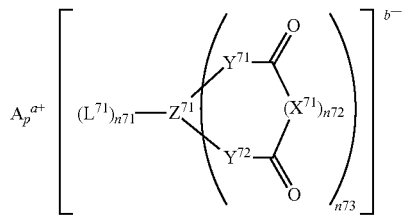

wherein
$A^{a+}$ is a metal ion, a hydrogen ion, or an onium ion; a is an integer of 1 to 3;
b is an integer of 1 to 3;
p is b/a;
$n^{73}$ is an integer of 1 to 4;
$n^{71}$ is an integer of 0 to 8;
$n^{72}$ is 0 or 1;

$Z^{71}$ is a transition metal or an element in Group III, IV, or V of the periodic table;

$X^{71}$ is O, S, a C1-C10 alkylene group, a C1-C10 halogenated alkylene group, a C6-C20 arylene group, or a C6-C20 halogenated arylene group, where the alkylene group, the halogenated alkylene group, the arylene group, and the halogenated arylene group each may have a substituent or a hetero atom in the structure, and $n^{73}$ $X^{71}$s may be bonded to each other when $n^{72}$ is 1 and $n^{73}$ is 2 to 4;

$L^{71}$ is a halogen atom, a cyano group, a C1-C10 alkyl group, a C1-C10 halogenated alkyl group, a C6-C20 aryl group, a C6-C20 halogenated aryl group, or —$Z^{73}Y^{73}$, where the alkylene group, the halogenated alkylene group, the arylene group, and the halogenated arylene group each may have a substituent or a hetero atom in the structure, and $n^{71}$ $L^{71}$s may be bonded to each other to form a ring when $n^{71}$ is 2 to 8;

$Y^{71}$, $Y^{72}$, and $Z^{73}$ are each individually O, S, $NY^{74}$, a hydrocarbon group, or a fluorinated hydrocarbon group; and $Y^{73}$ and $Y^{74}$ are each individually H, F, a C1-C10 alkyl group, a C1-C10 halogenated alkyl group, a C6-C20 aryl group, or a C6-C20 halogenated aryl group, where the alkyl group, the halogenated alkyl group, the aryl group, and the halogenated aryl group each may have a substituent or a hetero atom in the structure, and when there are multiple $Y^{73}$s or $Y^{74}$s, the $Y^{73}$s and $Y^{74}$s may be bonded to each other to form a ring; and a compound (8) represented by (8):

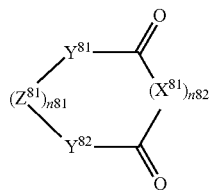

wherein
$n^{81}$ is 0 or 1;
$n^{82}$ is 0 or 1;
$Z^{81}$ is a transition metal or an element in Group III, IV, or V in the periodic table;
$X^{81}$ is O, S, a C1-C10 alkylene group, a C1-C10 halogenated alkylene group, a C6-C20 arylene group, or a C6-C20 halogenated arylene group, where the alkylene group, the halogenated alkylene group, the arylene group, and the halogenated arylene group each may have a substituent or a hetero atom in the structure;
$Y^{81}$ and $Y^{82}$ are each individually O, S, $NY^{84}$, a hydrocarbon group, or a fluorinated hydrocarbon group; and
$Y^{84}$ is H, a C1-C10 alkyl group, a C1-C10 halogenated alkyl group, a C6-C20 aryl group, or a C6-C20 halogenated aryl group, where the alkyl group, the halogenated alkyl group, the aryl group, and the halogenated aryl group each may have a substituent or a hetero atom in the structure, and when there is multiple $Y^{84}$s, the $Y^{84}$s may be bonded to each other to form a ring.

6. The electrolytic solution according to claim 1, further comprising at least one compound containing a multiple bond between a heteroatom other than an oxygen atom and an adjacent atom in a molecule selected from the group consisting of compounds represented by formula (9-1) to formula (9-3):

$$L^{91}\text{---}[(Z^{91}\text{=\!=}M^{91}\text{=\!=}[X^{91}]_{m91}]_{n91} \quad \text{formula (9-1)}$$

$$L^{91}\text{---}[M^{91}\text{≡}X^{91}]_{n91} \quad \text{formula (9-2)}$$

$$L^{91}\text{---}[M^{91}\text{=\!=}X^{91}]_{n91} \quad \text{formula (9-3)}$$

wherein
- $X^{91}$ is O or N, $M^{91}$ is C, P, S, or N, and $Z^{91}$ is N or may be absent, but $L^{91}\text{-}C\text{=}O$, where N is absent, $M^{91}$ is C, and $X^{91}$ is 0, is excluded;
- $L^{91}$ is a halogen atom or an oxygen atom, or R, OR, ORR', ORR'O, SR, NR, SiR, or OSiR that may contain a halogen atom;
- R and R' are each a C1-C10 alkyl group, a C1-C10 alkylene group, a C1-C10 alkene group, a C1-C10 alkyne group, a C1-C10 haloalkyl group, a C1-C10 haloalkylene group, a C1-C10 haloalkene group, a C1-C10 haloalkyne group, or a C1-C10 cycloalkyl group;
- R and R' may form a ring together;
- $n^{91}$ is an integer of 1 to 3; and
- $m^{91}$ is or 2.

7. The electrolytic solution according to claim 1, further comprising a compound containing structure represented by any of —CN, —N=C=O, $$\text{---}\underset{\underset{\text{O}}{\|}}{\text{S}}\text{---}, \quad \text{---}\underset{\underset{\text{O}}{\|}}{\overset{\overset{\text{O}}{\|}}{\text{S}}}\text{---}, \quad \text{---}\underset{|}{\overset{\overset{\text{O}}{\|}}{\text{P}}}\text{---}, \quad \text{and} \quad \text{---}\underset{|}{\text{N}}\text{=}\underset{|}{\text{P}}\text{---}.$$

8. The electrolytic solution according to claim 1, further comprising at least one compound containing a multiple bond between a hetero atom other than an oxygen atom and an adjacent atom in a molecule selected from the group consisting of:

a compound (10) represented by formula (10):

$$\text{NC}\text{---}R^{101}\text{---}(CN)_{n101}$$

wherein $R^{101}$ is a monovalent to trivalent hydrocarbon group or a monovalent to trivalent halogenated hydrocarbon group; and $n^{101}$ is an integer of 0 to 2;

a compound (11) represented by formula (11):

$$\text{OCN}\text{---}R^{111}\text{---}(NCO)_{n101}$$

wherein $R^{111}$ is a monovalent or divalent hydrocarbon group or a monovalent or divalent halogenated hydrocarbon group; and $n^{111}$ is 0 or 1;

a compound (12) represented by formula (12):

$$R^{121}\text{---}\underset{\underset{\text{O}}{\|}}{\overset{\overset{\text{O}}{\|}}{\text{S}}}\text{---}R^{122}$$

wherein $R^{121}$ and $R^{122}$ may be the same as or different from each other, and are each a halogen atom, a monovalent or divalent hydrocarbon group, or a monovalent or divalent halogenated hydrocarbon group; and $R^{121}$ and $R^{122}$ may be bonded to each other to form a ring;

a compound (13) represented by formula (13):

$$R^{131}\text{---}\underset{\underset{\text{O}}{\|}}{\overset{\overset{\text{O}}{\|}}{\text{S}}}\text{---}R^{132}$$

wherein $R^{131}$ and $R^{132}$ may be the same as or different from each other, and are each a halogen atom, a monovalent or divalent hydrocarbon group, or a monovalent or divalent halogenated hydrocarbon group; and $R^{131}$ and $R^{132}$ may be bonded to each other to form a ring;

a compound (14) represented by formula (14):

$$\underset{R^{141}}{\overset{\overset{\text{O}}{\|}}{\text{O=S}}}\text{---Z---}\underset{R^{142}}{\overset{\overset{\text{O}}{\|}}{\text{S=O}}}$$

wherein $R^{141}$ and $R^{142}$ may be the same as or different from each other, and are each a halogen atom, a monovalent or divalent hydrocarbon group, or a monovalent or divalent halogenated hydrocarbon group; $R^{141}$ and $R^{142}$ may be bonded to each other to form a ring; and Z is an oxygen atom or a C1-C10 alkylene group, a compound (15) represented by formula (15):

$$R^{151}\text{---}\underset{\underset{R^{153}}{|}}{\overset{\overset{\text{O}}{\|}}{\text{P}}}\text{---}R^{152}$$

wherein $R^{151}$ to $R^{153}$ may be the same as or different from each other, and are each an organic group;

a compound (16) represented by formula (16):

(cyclic phosphazene structure with $R^{161}$, $R^{162}$, $R^{163}$, $R^{165}$, $R^{165}$, $R^{166}$)

wherein $R^{161}$ to $R^{166}$ may be the same as or different from each other, and are each a halogen atom or an organic group; and a compound (17) represented by formula (17)

(cyclic phosphazene structure with $R^{171}$, $R^{172}$, $R^{173}$, $R^{174}$, $R^{175}$, $R^{176}$, $R^{177}$, $R^{178}$)

wherein $R^{171}$ to $R^{178}$ may be the same as or different from each other, and are each a halogen atom or an organic group.

9. An electrochemical device comprising the electrolytic solution according to claim 1.
10. A lithium ion secondary battery comprising: the electrolytic solution according to claim 1.
11. A module comprising the electrochemical device according to claim 9.
12. A module comprising the lithium ion secondary battery according to claim 10.

* * * * *